United States Patent
Yang et al.

(10) Patent No.: US 12,180,281 B2
(45) Date of Patent: Dec. 31, 2024

(54) ANTI-PD-1 ANTIBODIES AND METHODS OF TREATING CANCER

(71) Applicant: Biocytogen Pharmaceuticals (Beijing) Co., Ltd., Beijing (CN)

(72) Inventors: Yi Yang, Beijing (CN); Chunyan Dong, Beijing (CN); Fang Yang, Beijing (CN); Chengyuan Lu, Beijing (CN); Yuelei Shen, Beijing (CN); Jian Ni, Beijing (CN); Yanan Guo, Beijing (CN); Yunyun Chen, Beijing (CN); Jingshu Xie, Beijing (CN)

(73) Assignee: Biocytogen Pharmaceuticals (Beijing) Co., Ltd.

( * ) Notice: Subject to any disclaimer, the term of this patent is extended or adjusted under 35 U.S.C. 154(b) by 95 days.

(21) Appl. No.: 17/725,133

(22) Filed: Apr. 20, 2022

(65) Prior Publication Data

US 2022/0324978 A1  Oct. 13, 2022

Related U.S. Application Data

(60) Division of application No. 17/324,751, filed on May 19, 2021, now Pat. No. 11,352,429, which is a (Continued)

(30) Foreign Application Priority Data

Nov. 19, 2018  (WO) ................ PCT/CN2018/116211

(51) Int. Cl.
*A61K 39/395* (2006.01)
*A61K 47/68* (2017.01)
(Continued)

(52) U.S. Cl.
CPC ...... *C07K 16/2818* (2013.01); *A61K 47/6849* (2017.08); *A61K 2039/505* (2013.01);
(Continued)

(58) Field of Classification Search
None
See application file for complete search history.

(56) References Cited

U.S. PATENT DOCUMENTS 4,522,811 A   6/1985  Eppstein et al.
4,603,112 A   7/1986  Paoletti et al.
(Continued)

FOREIGN PATENT DOCUMENTS

CN  108314734  7/2018
CN  108368170  8/2018
(Continued)

OTHER PUBLICATIONS

NIH Nat'l Cancer Inst., Definition of "solid tumor", Retrieved online from: <URL:https://www.cancer.gov/publications/dictionaries/cancer-terms/def/solid-tumor>, [retrieved on Mar. 18, 2024] 2024.*
(Continued)

*Primary Examiner* — Claire Kaufman
(74) *Attorney, Agent, or Firm* — Fish & Richardson P.C.

(57) ABSTRACT

This disclosure relates to anti-PD-1 (Programmed Cell Death Protein 1) antibodies, antigen-binding fragments, and the uses thereof.

30 Claims, 25 Drawing Sheets

Specification includes a Sequence Listing.

Related U.S. Application Data continuation of application No. PCT/CN2019/119798, filed on Nov. 20, 2019.

(51) Int. Cl.
    *C07K 16/28*     (2006.01)
    *A61K 39/00*     (2006.01)
    *A61P 35/00*     (2006.01)

(52) U.S. Cl.
    CPC .......... *A61P 35/00* (2018.01); *C07K 2317/24* (2013.01); *C07K 2317/33* (2013.01); *C07K 2317/565* (2013.01); *C07K 2317/732* (2013.01); *C07K 2317/76* (2013.01); *C07K 2317/92* (2013.01)

(56) References Cited

U.S. PATENT DOCUMENTS

| | | |
|---|---|---|
| 4,676,980 A | 6/1987 | Segal et al. |
| 4,769,330 A | 9/1988 | Paoletti et al. |
| 4,777,127 A | 10/1988 | Suni et al. |
| 5,017,487 A | 5/1991 | Stunnenberg et al. |
| 7,261,890 B2 | 8/2007 | Krah, III et al. |
| 8,728,474 B2 | 5/2014 | Honjo et al. |
| 9,834,606 B2 | 12/2017 | Li et al. |
| 9,944,704 B2 | 4/2018 | Morsey et al. |
| 10,023,636 B2 | 7/2018 | Morsey et al. |
| 10,106,607 B2 | 10/2018 | Morsey et al. |
| 10,280,223 B2 | 5/2019 | Mizuno et al. |
| 10,711,061 B2 | 7/2020 | Morsey et al. |
| 10,927,172 B2 | 2/2021 | Morsey et al. |
| 11,352,429 B2 | 6/2022 | Yang et al. |
| 2016/0159905 A1 | 6/2016 | Abdiche et al. |
| 2016/0264656 A1 | 9/2016 | Lacy et al. |
| 2017/0044259 A1 | 2/2017 | Tipton et al. |
| 2017/0081409 A1 | 3/2017 | Dijk et al. |
| 2017/0158756 A1 | 6/2017 | Bergeron et al. |
| 2017/0247454 A1 | 8/2017 | Benz et al. |
| 2020/0332007 A1 | 10/2020 | Yang et al. |
| 2021/0284735 A1 | 9/2021 | Yang et al. |
| 2021/0400933 A1* | 12/2021 | Shen .................. C12N 15/8509 |
| 2022/0324977 A1* | 10/2022 | Mi ...................... C07K 16/2818 |

FOREIGN PATENT DOCUMENTS

| | | |
|---|---|---|
| CN | 108601829 | 9/2018 |
| EP | 0345242 | 12/1989 |
| GB | 2200651 | 8/1988 |
| JP | 2017-500866 | 1/2017 |
| JP | 2017-500867 | 1/2017 |
| JP | 2018-527952 | 9/2018 |
| WO | WO 1989/01973 | 3/1989 |
| WO | WO 1991/02805 | 3/1991 |
| WO | WO 1996/27011 | 9/1996 |
| WO | WO 2008/077546 | 7/2008 |
| WO | WO 2014/179664 | 11/2014 |
| WO | WO 2015/091914 | 6/2015 |
| WO | WO 2016/006241 | 1/2016 |
| WO | WO 2017/040790 | 3/2017 |
| WO | WO 2017/058115 | 4/2017 |
| WO | WO 2018/052818 | 3/2018 |

OTHER PUBLICATIONS

Koenig et al., Mutational landscape of antibody variable domains reveals a switch modulating the interdomain conformational dynamics and antigen binding, Proc. Natl. Acad. Sci. USA, 114(4):E486-495, Jan. 2017.*

Sela-Culang et al., The structural basis of antibody-antigen recognition, Front. Immunol. 4:302, 13 pages, Oct. 2013.*

Abhinandan et al., "Analysis and improvements to Kabat and structurally correct numbering of antibody variable domains," Molecular immunology, Aug. 1, 2008, 45(14):3832-3839.

Bitter et al., "[33] Expression and secretion vectors for yeast," Methods in enzymology, Jan. 1, 1987, 153:516-544.

Brennan et al., "Preparation of bispecific antibodies by chemical recombination of monoclonal immunoglobulin G1 fragments," Science, Jul. 5, 1985, 229(4708):81-83.

Chothia et al., "Conformations of immunoglobulin hypervariable regions," Nature, Dec. 1989, 342(6252):877-883.

Cohen, "Naked DNA points way to vaccines," Science, 1993, 259(5102): 1691-1692.

Creelan, "Update on immune checkpoint inhibitors in lung cancer," Cancer Control, Jan. 2014, 21(1):80-89.

Fisher-Hoch et al., "Protection of rhesus monkeys from fatal Lassa fever by vaccination with a recombinant vaccinia virus containing the Lassa virus glycoprotein gene," Proceedings of the National Academy of Sciences, Jan. 1, 1989, 86(1):317-321.

Flexner et al., "Attenuation and immunogenicity in primates of vaccinia virus recombinants expressing human interleukin-2," Vaccine, Feb. 1, 1990, 8(1):17-21.

GenBank Accession No. AAF09245.1, "immunoglobulin kappa light chain [Felis catus]," Mar. 10, 2010, 1 page.

GenBank Accession No. AAL35301.1, "immunoglobulin gamma heavy chain A [Canis lupus familiaris]," Mar. 11, 2010, 1 page.

GenBank Accession No. AAL35302.1, "immunoglobulin gamma heavy chain B [Canis lupus familiaris]," Mar. 11, 2010, 1 page.

GenBank Accession No. AAL35303.1, "immunoglobulin gamma heavy chain C [Canis lupus familiaris]," Mar. 11, 2010, 1 page.

GenBank Accession No. AAL35304.1, "immunoglobulin gamma heavy chain D [Canis lupus familiaris]," Mar. 11, 2010, 1 page.

GenBank Accession No. BAA32229.1, "IgG1 heavy chain, partial [Felis catus]," Jul. 25, 2016.

GenBank Accession No. XP_532962.3, "Predicted: ig kappa chain V-II region RPMI 6410-like [Canis lupus familiaris]," Sep. 8, 2011, 1 pages.

Ghetie et al., "Homodimerization of tumor-reactive monoclonal antibodies markedly increases their ability to induce growth arrest or apoptosis of tumor cells," Proceedings of the National Academy of Sciences, Jul. 8, 1997, 94(14):7509-7514.

Guzman et al., "Efficient and selective adenovirus-mediated gene transfer into vascular neointima," Circulation, Dec. 1993, 88(6):2838-2848.

Guzman et al., "Efficient gene transfer into myocardium by direct injection of adenovirus vectors," Circulation Research, Dec. 1993, 73(6):1202-1207.

Hirano et al., "Blockade of B7-H1 and PD-1 by monoclonal antibodies potentiates cancer therapeutic immunity," Cancer research, Feb. 1, 2005, 65(3):1089-1096.

Houdebine et al., "Antibody manufacture in transgenic animals and comparisons with other systems," Current opinion in biotechnology, Dec. 1, 2002, 13(6):625-629.

International Preliminary Report on Patentability in International Appln. No. PCT/CN2019/119798, dated Jun. 3, 2021, 7 pages.

International Search Report on Patentability in International Appln. No. PCT/CN2019/119798, dated Feb. 14, 2020, 12 pages.

Irani et al., "Molecular properties of human IgG subclasses and their implications for designing therapeutic monoclonal antibodies against infectious diseases," Molecular immunology, Oct. 1, 2015, 67(2):171-182.

Kass-Eisler et al., Quantitative determination of adenovirus-mediated gene delivery to rat cardiac myocytes in vitro and in vivo. Proceedings of the National Academy of Sciences. Dec. 15, 1993;90(24):11498-502.

Köhler et al., "Continuous cultures of fused cells secreting antibody of predefined specificity," Nature, Aug. 1975, 256(5517):495-497.

Kolls et al., "Prolonged and effective blockade of tumor necrosis factor activity through adenovirus-mediated gene transfer," Proceedings of the National Academy of Sciences, Jan. 4, 1994, 91(1): 6 pages.

Kozbor et al., "The production of monoclonal antibodies from human lymphocytes," Immunology Today, Mar. 1, 1983, 4(3):72-79.

Kwok et al., "Pembrolizumab (Keytruda)," Human vaccines & immunotherapeutics, Nov. 1, 2016, 12(11): 14 pages.

(56) References Cited

OTHER PUBLICATIONS

Maekawa et al., "A canine chimeric monoclonal antibody targeting PD-L1 and its clinical efficacy in canine oral malignant melanoma or undifferentiated sarcoma," Scientific reports, Aug. 21, 2017, 7(1):1-12.
Martin et al., "Molecular modeling of antibody combining sites," Methods in enzymology, Jan. 1, 1991, 203:121-153.
Martin, "Protein sequence and structure analysis of antibody variable domains," Antibody engineering, Springer Berlin Heidelberg, 2001, 422-439.
Morea et al., "Antibody structure, prediction and redesign," Biophysical chemistry, Oct. 1, 1997, 68(1-3):9-16.
Morea et al., "Conformations of the third hypervariable region in the VH domain of immunoglobulins," Journal of molecular biology, Jan. 16, 1998, 275(2):269-294.
Moss et al., "Vaccinia Virus Expression Vectors," Annals of the New York Academy of Sciences, 1989, 569:86-103.
Nemoto et al., "Development and characterization of monoclonal antibodies against canine PD-1 and PD-L1," Veterinary immunology and immunopathology, Apr. 1, 2018, 198: 38 pages.
Ponomarenko et al., "Antibody-protein interactions: benchmark datasets and prediction tools evaluation," BMC structural biology, Dec. 2007, 7(64):1-19.
Raedler, "Keytruda (pembrolizumab): first PD-1 inhibitor approved for previously treated unresectable or metastatic melanoma," American health & drug benefits, Mar. 2015, 8(Spec Feature):96-101.
Rosenfeld et al., "Adenovirus-mediated transfer of a recombinant alpha 1-antitrypsin gene to the lung epithelium in vivo," Science, Apr. 19, 1991, 252(5004):431-434.
Schillberg et al., "Molecular farming of recombinant antibodies in plants," Cellular and Molecular Life Sciences CMLS, Mar. 2003, 60(3):433-445.
Silva et al., "The S228P mutation prevents in vivo and in vitro IgG4 Fab-arm exchange as demonstrated using a combination of novel quantitative immunoassays and physiological matrix preparation," Journal of Biological Chemistry, Feb. 27, 2015, 290(9):5462-5469.
Singer et al., "Generation of a canine anti-EGFR (ErbB-1) antibody for passive immunotherapy in dog cancer patients," Molecular cancer therapeutics, Jul. 1, 2014, 13(7):1777-1790.
Topalian et al., "Safety, activity, and immune correlates of anti-PD-1 antibody in cancer," New England Journal of Medicine, Jun. 28, 2012, 366(26):2443-2454.
Ulmer et al., "Heterologous protection against influenza by injection of DNA encoding a viral protein," Science, Mar. 19, 1993, 259(5102):1745-1749.
Vidarsson et al., "IgG subclasses and allotypes: from structure to effector functions," Frontiers in immunology, Oct. 20, 2014, 5(520):1-17.
Wolff et al., "Monoclonal antibody homodimers: enhanced antitumor activity in nude mice," Cancer Research, Jun. 1, 1993, 53(11):2560-2565.
Wu et al., "An analysis of the sequences of the variable regions of Bence Jones proteins and myeloma light chains and their implications for antibody complementarity," Journal of Experimental Medicine, Aug. 1, 1970, 132(2):211-250.
Zhao et al., "Enhancing tumor targeting and apoptosis using noncovalent antibody homodimers, Journal of Immunotherapy," Sep. 1, 2002, 25(5):396-404.
Partial Supplementary European Search Report in European Appln. No. 19886570.1, dated Jul. 13, 2022, 15 pages.
Extended European Search Report in European Appln. No. 19886570.1, dated Oct. 17, 2022, 13 pages.
Karlsson et al., "Kinetic and Concentration Analysis Using BIA Technology," Methods, Jun. 1994, 6(2):99-110.

\* cited by examiner

Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 13-1B9 | SFWMN | 1 | RVDPYDSETHYNQKFKD | 2 | QFGFSWLAY | 3 | KSSQSLLYSSNQKNYLA | 4 | WASTRES | 5 | QQYYSNPYT | 6 |
| 12-4A7 | NFGMS | 7 | TISSGSSYSYYSDSVKG | 8 | GESRFAY | 9 | RSNKSLLYEDGQTYLN | 10 | LMSTRAS | 11 | QQLIEYPLT | 12 |
| 12-1D8 | NFGMS | 13 | TLSSGSSYTYYSDSVKG | 14 | GESRFAY | 15 | RSSKSLLYKDGKTYLN | 16 | LMSTRAS | 17 | QQLIEYPLT | 18 |

FIG. 16

Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 13-1B9 | GYTFTSFWMN | 19 | DPYDSE | 20 | QFGFSWLAY | 21 | KSSQSLLYSSNQKNYLA | 22 | WASTRES | 23 | QQYSNPYT | 24 |
| 12-4A7 | GFPFSNFGMS | 25 | SSGSSY | 26 | GESRFAY | 27 | RSNKSLLYEDGQTYLN | 28 | LMSTRAS | 29 | QQLIEYPLT | 30 |
| 12-1D8 | GFTFNNFGMS | 31 | SSGSSY | 32 | GESRFAY | 33 | RSSKSLLYKDGKTYLN | 34 | LMSTRAS | 35 | QQLIEYPLT | 36 |

| Protein | Amino acid sequence | SEQ ID NO: |
|---|---|---|
| Human PD-1 (hPD-1) NP_005009.2 | MQIPQAPWPVVWAVLQLGWRPGWFLDSPDRPWNPPTFSPALLVVTEGDNATFTCSFSNTSESFVLNWYRM SPSNQTDKLAAFPEDRSQPGQDCRFRVTQLPNGRDFHMSVVRARRNDSGTYLCGAISLAPKAQIKESLRA ELRVTERRAEVPTAHPSPSPRPAGQFQTLVVGVVGGLLGSLVLLVWVLAVICSRAARGTIGARRTGQPLK EDPSAVPVFSVDYGELDFQWREKTPEPPVPCVPEQTEYATIVFPSGMGTSSPARRGSADGPRSAQPLRPE DGHCSWPL | 37 |
| Mouse PD-1 (mPD-1) NP_032824.1 | MWVRQVPWSFTWAVLQLSWQSGWLLEVPNGPWRSLTFYPAWLTVSEGANATFTCSLSNWSEDLMLNWNRL SPSNQTEKQAAFCNGLSQPVQDARFQIIQLPNRHDFHMNILDTRRNDSGIYLCGAISLHPKAKIEESPGA ELVVTERILETSTRYPSPSPKPEGRFQGMVIGIMSALVGIPVLLLLAWALAVFCSTSMSEARGAGSKDDT LKEEPSAAPVPSVAYEELDFQGREKTPELPTACVHTEYATIVFTEGLGASAMGRRGSADGLQGPRPPRHE DGHCSWPL | 38 |
| Monkey PD-1 (rmPD-1) NP_001107830.1 | MQIPQAPWPVVWAVLQLGWRPGWFLESPDRPWNPPTFSPALLLVTEGDNATFTCSFSNASESFVLNWYRM SPSNQTDKLAAFPEDRSQPGRDCRFRVTQLPNGRDFHMSVVRARRNDSGTYLCGAISLAPKAQIKESLRA ELRVTERRAEVPTAHPSPSPRPAGQFQALVVGVVGGLIGSLVLLVWVLAVICSRAAQTIEARRTGQPLK EDPSAVPVFSVDYGELDFQWREKTPEPPAPCVPEQTEYATIVFPSGLGTSSPARRGSADGPRSPRLRPE DGHCSWPL | 39 |
| Chimeric PD-1 (chidPD-1) (Caninized PD-1) | MWVRQVPWSFTWAVLQLSWQSGWLLEVPNGPWSPLTFSPAQLTVQEGENATFTCSLADIPDSFVLNWYRL SPRNQTDKLAAFQEDRIEPGRDRRFRVTRLPNGRDFHMSIVAARLNDSGIYLCGAIYLPNTQINESPRA ELVVTERILETSTRYPSPSPKEGRFQGMVIGIMSALVGIPVLLLLAWALAVFCSTSMSEARGAGSKDDT LKEEPSAAPVPSVAYEELDFQGREKTPELPTACVHTEYATIVFTEGLGASAMGRRGSADGLQGPRPPRHE DGHCSWPL | 40 |
| Canine PD-1 (dPD-1) NP_001301026.1 | 1   MGSRRGPWPL VWAVLQLGWW PGWLLDSPDR PWSPLTFSPA QLTVQEGENA TFTCSLADIP 61  DSFVLNWYRL SPRNQTDKLA AFQEDRIEPG RDRRFRVTRL PNGRDFHMSI VAARLNDSGI 121 YLCGAIYLPP NTQINESPRA ELSVTERTLE PPTQSPSPPP RLSGQLQGLV IGVTSVLVGV 181 LLLLLLTWVL AAVFPRATRG ACVCGSEDEP LKEGPDAAPV FTLDYGELDF QWREKTPEPP 241 APCAPEQTEY ATIVFGPRPA SPGRRASASS LQGAQPPSPE DGPGLWPP | 41 |
| Panda PD-1 (pPD-1) XP_019659246.1 | 1   MGAPRAPWPL VWAVLQLGWW PGWLLDSPER PWSPLTFSPA QLAVHEGENA TFTCSLSSVP 61  ESFVLNWYRM SPRNQTDKLA AFQEDRIQPG PDRRFHVTRL PNGRDFHMSI VATQLSDSGT 121 YLCGAIYLPP NTQINESPRA ELITVKERILE PPTESPSPPP RITNQLQGLV IGITSVLVGV 181 PLLLLLTWVL AAAFPRATRG TCACGSEDAP LVSFLPFAAP GWPRSSPVPE FEQRDTRPWE 241 GAWSTGPALA LLMWPHVRTRA SVPLPVCHPE TTDASLLLSL KKEGPSAAPV FTVDYGELDF 301 QWREKTPEPS APCAPEQTEY ATIVFPSRPG SPGRRASAHS PQGPQPLSPE DGPCPWPL | 61 |
| Feline PD-1 (cPD-1) NP_001138982.1 | 1   MGTPRAPWPL VWAVLQLGWW PGWLLDSPYR PWSPLTFSPA QLTVLEGENA TFVCHLPDVP 61  ESFVLNWYRV SPRNQTDKLA AFQENHTEPG KDRRFRVTRL PSGQDFHTTI LAAQLNDSGI 121 YLCGAIYLPP NTQIYESPRA ELTVKERVLE PPTESPSPPP RLTGQGQGLV VGVTSVLVGV 181 LLLLLLTWVL AAAFPRATRG ACACGSEDEP LKEGPSAAPV FTVDYGELDF QWREKTPEPP 241 APCAPEQTEY ATIVFPSRPG SPGPLPLRPE DGPCPWPL | 62 |

FIG. 19

| Humanized antibody variable domains | Description | AMINO ACID SEQUENCE | SEQ ID NO: |
|---|---|---|---|
| 1D8 Caninized heavy chain variable domain (H1) | CanVHv1(canonized percentage 88.5%; top hit to Canidae) | EVQLVESGGDLVKPVGSLRLSCVASGFTFNNFGMSWVRQAPGKGLQWVATLSSGSSYTYYSDSVKGRFTISRDNAKNTLYLQMNSLRAEDTAMYYCTRGESRFAYWGQGTLVTVSA | 42 |
| 1D8 Caninized heavy chain variable domain (H2) | CanVHv2(canonized percentage 87.5%; top hit to Canidae) | EVQLVESGGDLVKPVGSLRLSCVASGFTFNNFGMSWVRQAPGKGLEWVATLSSGSSYTYYSDSVKGRFTISRDNAKNTLYLQMNSLRAEDTAMYYCTRGESRFAYWGQGTLVTVSA | 43 |
| 1D8 Caninized heavy chain variable domain (H3) | CanVHv3(canonized percentage 84.4%; non top hit to Canidae) | EVQLVESGGDLVKPVGSLRLSCAASGFTFNNFGMSWVRQAPDKRLEWVATLSSGSSYTYYSDSVKGRFTISRDNAKNTLYLQMNSLRAEDTAMYYCTRGESRFAYWGQGTLVTVSA | 44 |
| 1D8 Caninized light chain variable domain (K1) | CanVLv1(canonized percentage 82.7%; non top hit to Canidae) | GVVITQDpLSlaVTpGElVtISCRSSKSLLYKDGKTYLNWylQkPGQtPrLLIYLMSTRASGVSDRFSGSGSTDFTLKISRVeAEDVGVYYCQQLIEYPLTFGAGTKvELK | 45 |
| 1D8 Caninized light chain variable domain (K2) | CanVLv2(canonized percentage 81.6%;non top hit to Canidae) | GVVITQDPLSLAVTPGELVTISCRSSKSLLYKDGKTYLNWFLQKPGQTPRLLIYLMSTRASGVSDRFSGSGSTDFTLKISRVEAEDVGVYYCQQLIEYPLTFGAGTKVELK | 46 |
| 1D8 Caninized light chain variable domain (K3) | CanVLv3(canonized percentage 79.6%; non top hit to Canidae) | GVVITQDELSLAVTPGELVTISCRSSKSLLYKDGKTYLNWFLQKPGQTPQLLIYLMSTRASGVSDRFSGSGSTDFTLKISRVEAEDVGVYYCQQLIEYPLTFGAGTKVELK | 47 |
| 1D8 Caninized light chain variable domain (K4) | CanVLv4(canonized percentage 77.6%;non top hit to Canidae) | GVVITQDPLSLAVTPGQSPQLLIYLMSTRASGVSDRFSGSGSTDFTLEISRVKAEDVGVYYCQQLIEYPLTFGAGTKVELK | 48 |

FIG. 20

| Humanized antibody variable domains | Description | AMINO ACID SEQUENCE | SEQ ID NO: |
|---|---|---|---|
| 1B9 Caninized heavy chain variable domain (H1) | CanVHv1(canonized percentage 81.4%; top hit to Canidae) | EVQLVQSGAEVKKPGASVKVSCKTSGYTFTSFWMNWV RLAPGAGLDWIGRVDPYDSETHYNQKFKDRVILTVDT STSTAYMELSSLRAGDIAVYYCATQFGFSWLAYWGQG TLVTVSA | 49 |
| 1B9 Caninized heavy chain variable domain (H2) | CanVHv2(canonized percentage 78.4%; top hit to Canidae) | EVQLVQSGAEVKKPGASVKVSCCKASGYTFTSFWMNWV RLAPGAGLEWIGRVDPYDSETHYNQKFKDRAILTVDT STSTAYMELSSLRAGDIAVYYCATQFGFSWLAYWGQG TLVTVSA | 50 |
| 1B9 Caninized heavy chain variable domain (H3) | CanVHv3(canonized percentage 76.3%; top hit to Canidae) | EVQLVQSGAEVKKPGASVKVSCKASGYTFTSFWMNWV KLAPGQGLEWIGRVDPYDSETHYNQKFKDRAILTVDT STSTAYMELSSLRAGDIAVYYCATQFGFSWLAYWGQG TLVTVSA | 51 |
| 1B9 Caninized light chain variable domain (K1) | CanVLv1(canonized percentage 89.1%; top hit to Canidae) | EIVMTQSPGSLAGSAGESVSINCKSSQSLLYSSNQKN YLAWYQQKPGESPKLLIYWASTRESGVPDRFSGSGSG TDFTLTINNLQAEDVGVYYCQQYYSNPYTFGQGTKLE IK | 52 |
| 1B9 Caninized light chain variable domain (K2) | CanVLv2(canonized percentage 86.1%;non top hit to Canidae) | DIVMTQSPGSLAVSAGEKVSINCKSSQSLLYSSNQKN YLAWYQQKPGESPKLLIYWASTRESGVPDRFSGSGSG TDFTLTINNVQAEDVGVYYCQQYYSNPYTFGQGTKLE IK | 53 |
| 1B9 Caninized light chain variable domain (K3) | CanVLv3(canonized percentage 83.2%; non top hit to Canidae) | DIVMTQSPGSLAVSAGEKVSINCKSSQSLLYSSNQKN YLAWYQQKPGQSPKLLIYWASTRESGVPDRFSGSGSG TDFTLTINNVKAEDVGVYYCQQYYSNPYTFGQGTKLE IK | 54 |

12-4A7 ("4A7") Heavy chain variable region (SEQ ID NO:55)
EVQLVESGGDLVKPGGSLKLSCVASGFPFSNFGMSWVRQTPDKRLEWVATISSGSSYSYYSDSVKGRFTISRDNAKNTLFLQMNSLKSEDTAIFYCARGESRFAYWGQGTLVTVSA

12-4A7 ("4A7") Light chain variable region (SEQ ID NO: 56)
DVVITQDELSNPVTSGESVSISCRSNKSLLYEDGQTYLNWFLQRPGQSPQLLIYLMSTRASGVSDRFSGSGSGTDFTLEISEVRAEDVGVYYCQQLIEYPLTFGAGTKLELK

12-1D8 ("1D8") Heavy chain variable region (SEQ ID NO: 57)
EVQLVESGGDLVKPGGSLKLSCAASGFTFNNFGMSWVRQNPDKRLEWVATLSSGSSYTYYSDSVKGRFTISRDNAKNTLYLQMNSLKSEDTAMYYCTRGESRFAYWGQGTLVTVSA

12-1D8 ("1D8") Light chain variable region (SEQ ID NO: 58)
GVVITQDELSNPVTSGESVSISCRSSKSLLYKDGKTYLNWFLQRPGQSPQLLIYLMSTRASGVSDRFSGSGSGTDFTLEISRVKAEDVGVYYCQQLIEYPLTFGAGTKLELK

13-1B9 ("1B9") Heavy chain variable region (SEQ ID NO:59)
QVQLQQPGAELVRPGASVKLSCKASGYTFTSFWMNWVKLRPEQGLEWIGRVDPYDSETHYNQKFKDKAILTVDKSSSTAYMQLSSLTSEDSAVYYCATQFGFSWLAYWGQGTLVTVSA

13-1B9 ("1B9") Light chain variable region (SEQ ID NO: 60)
DIVMSQSPSSLAVSVGEKVTLSCKSSQSLLYSSNQKNYLAWYQQKPGQSPKLLIYWASTRESGVPDRFTGSGSGTDFTLTISSVKAEDLAVYYCQQYYSNPYTFGGGTKLEIK

SEQ ID NO: 63 Immunoglobulin gamma heavy chain A [Canis lupus familiaris]
GenBank: AAL35301.1

```
  1 mesvfcwvfl vviilkgvgge vqlvesggdl vkpggslrls cvasgftfss yymhwirqap
 61 gkglqrvahi rgdgrtthya damkgrftis rdnakntlyl qmnsltvedt aiyycvkdiy
121 ygvgdywggq tlvtvssast tapsvfplap scgstsgstv alaclvsgyf pepvtvswns
181 gsltsgvhtf psvlqssglh slssmvtvps srwpsetftc nvvhpasntk vdkpvfnecr
241 ctdtppcpvp eplggpsvli fppkpkdilr itrtpevtcv vldlgredpe vqiswfvdgk
301 evhtaktqsr eqfngtyrv vsvlpiehqd wltgkefkcr vnhidlpspi ertiskargr
361 ahkpsvyvlp pspkelsssd tvsitclikd fyppdidvew qsngqqeper khrmtppqld
421 edgsyflysk lsvdksrwqq gdpftcavmh etlqnhytdl slshspgk
```

SEQ ID NO: 64 Immunoglobulin gamma heavy chain B [Canis lupus familiaris]
GenBank: AAL35302.1

```
  1 mesvlfwvfl vtilkgvgge vrlvesggtl vkpggslkls cvasgftfrr ysmdwvrqap
 61 gkslqwvagi ngdgtgtsys qtvkgrftis rdnakntlyl qinslraeds avyycaksws
121 rngdldywgq gtlvtvssas ttapsvfpla pscgstsgst valaclvsgy fpepvtvswn
181 sgsltsgvht fpsvlqssgl yslssmvtvp ssrwpsetft cnvahpaskt kvdkpvpkre
241 ngrvprppdc pkcpapemlg gpsvfifppk pkdtlliart pevtcvvvdl dpedpevqis
301 wfvdgkqmqt aktqpreeqf ngtyrvvsvl pighqdwlkg kqftckvnnk alpspierti
361 skargqahqp svyvlppsre elskntvslt clikdffppd idvewqsngq qepeskyrtt
421 ppqldedgsy flysklsvdk srwqrgdtfi cavmhealhn hytqeslshs pgk
```

SEQ ID NO: 65 Ig kappa chain V-II region RPMI 6410-like [Canis lupus familiaris]
NCBI Reference Sequence: XP_532962.3

```
  1 mrfpsqligl lmlwipgsgg divmtqtpps lsvsprepas iscrasqsll hsngntylnw
 61 frqkpgqspe gliykvsnrf tgvsdrfsgs gsgtdftlri srveaddtgv yycggtqlp
121 ptpslwltfg qgtkveikrn daqpavylfq pspdqlhtgs asvvcllnsf ypkdinvkwk
181 vdgviqdtgi qesvteqdkd styslsstlt mssteylshe lysceithks lpstliksfq
241 rsecqrvd
```

FIG. 22 (Continued)

SEQ ID NO: 66 IgG1 heavy chain, partial [Felis catus]
GenBank: BAA32229.1

```
  1 asttapsvfp lapscgttsg atvalaclvl gyfpepvtvs wnsgaltsgv htfpavlqas
 61 glyslssmvt vpssrwlsdt ftcnvahpps ntkvdktvrk tdhppgpkpc dcpkcpppem
121 lggpsififp pkpkdtlsis rtpevtclvv dlgpddsdvq itwfvdntqv ytaktspree
181 qfnstyrvvs vlpilhqdwl kgkefkckvn skslpspier tiskakgqph epqvyvlppa
241 qeelsrnkvs vtcliksfhp pdiaveweit gqepepennyr ttppqldsdg tyfvysklsv
301 drshwqrgnt ytcsvsheal hshhtqkslt qspgk
```

SEQ ID NO: 67 Immunoglobulin kappa light chain [Felis catus]
GenBank: AAF09245.1

```
  1 mrfpaqllgl imlwipgssg divmtqtpls lsvtpgepas iscrasqsll ysdgntylnw
 61 ylqkpgqspr rliylvsnrd sgvpdrfsgs gsgtdftlri srveaddvgv yycgqglqhp
121 ltfgpgtkle ikrsdaqpsv flfqpsldel htgsasivci lndfypkevn vkwkvdgvvq
181 nkgiqestte qnskdstysl sstltmsste yqshekfsce vthkslastl vksfnrsecq
241 re
```

SEQ ID NO: 68   Immunoglobulin gamma heavy chain C [Canis lupus familiaris]
(GenBank: AAL35303.1)

```
  1 mesvlywvfl vailkgvqgd vqlvesggdl vkpggslrls cvasgftfss camswvrqsp
 61 gkgpqwvati rydgsdiyya davkgrfsis rdnakntvyl qmnslraedt avyycakapp
121 ydsyhygmdy wgpgtslfvs sasttapsvf plapscgsqs gstvalaclv sgyipepvtv
181 swnsvsltsg vhtfpsvlqs sglyslssmv tvpssrwpse tftcnvahpa tntkvdkpva
241 kececkcncn ncpcpgcgll ggpsvfifpp kpkdilvtar tptvtcvvvd ldpenpevqi
301 swfvdskqvq tantqpreeq sngtyrvvsv lpighqdwls gkqfkckvnn kalpspieei
361 isktpgqahq pnvyvlppsr demskntvtl tclvkdffpp eidvewqsng qqepeskyrm
421 tppqldedgs yflysklsvd ksrwqrgdtf icavmheaIh nhytqislsh spgk
```

FIG. 22 (Continued)

SEQ ID NO: 69 Immunoglobulin gamma heavy chain D [Canis lupus familiaris]
(GenBank: AAL35304.1)

```
  1 mesvlcwvfl vsilkgvqge vqlvesggdl vkpggslrls cvasgftfsd ygmswvrqsp
 61 gkglqwvaav snrgdtyyad avkgrftisr dnakntlylq msslkaedta iyhcvtgvwp
121 rhyygmdhwg ngtslfvssa sttapsvfpl apscgstsgs tvalaclvsg yfpepvtvsw
181 nsgsltsgvh tfpsvlqssg lyslsstvtv pssrwpsetf tcnvvhpasn tkvdkpvpke
241 stckcispcp vpeslggpsv fifppkpkdi lritrtpeit cvvldlgred pevqiswfvd
301 gkevhtaktq preqqfnsty rvvsvlpieh qdwltgkefk crvnhiglps piertiskar
361 gqahqpsvyv lppspkelss sdtvtltcli kdffppeidv ewqsngqpep eskyhttapq
421 ldedgsyfly sklsvdksrw qqgdtftcav mhealqnhyt dlslshspgk
```

SEQ ID NO: 70   Amino acid sequence of canine light chain constant region
RNDAQPAVYLFQPSPDQLHTGSASVVCLLNSFYPKDINVKMKVDGVIQDTGIQESVTEQDKDSTYSLSSTLTMSSTEYLSHELYSCEITHKSLPSTLI
KSFQRSECQRVD SEQ ID NO: 71   Amino acid sequence of canine light chain constant region
TDAQPAVYLFQPSPDQLHTGSASVVCLLNSFYPKDINVKMKVDGVIQDTGIQESVTEQDKDSTYSLSSTLTMSSTEYLSHELYSCEITHKSLPSTLIK
SFQRSECQRVD SEQ ID NO: 72   Caninized heavy chain of 1B9
MEWSWVFLFLLSVIAGVQSEVQLVQSGAEVKKPGASVKVSCKTSGYTFTSFWMNWVRLAPGAGLDWIGRVDPYDSETHYNQKFKDRVILTVDTSTSTA
YMELSSLRAGDIAVYYCATQFGFSWNLAYWGQGTLVTVSAASTTAPSVFPLAPSCGSTSGSTVALACLVSGYFPEPVTVSWNSGSLTSGVHTFPSVLQS
SGLYSLSSTVTVPSSRWPSETFTCNVVHPASNTKVDKPVPKESTCKCISPCPVPESLGGPSVFIFPPKPKDILRITRTPEITCVVLDLGREDPEVQIS
WFVDGKEVHTAKTQPREQQFNSTYRVVSVLPIEHQDWLTGKEFKCRVNHIGLPSPIERTISKARGQAHQPSVYVLPPSPKELSSSDTVTLTCLIKDFF
PPEIDVEWQSNGQPEPESKYHTTAPQLDEDGSYFLYSKLSVDKSRWQQGDTFTCAVMHEALQNHYTDLSLSHSPGK SEQ ID NO: 73   Caninized light chain of 1B9
MSVLTQVLALLLWLTGARCEIVMTQSPGSLAGSAGESVSINCKSSQSLLYSSNQKNYLAWYQQKPGESPKLLIYWASTRESGVPDRFSGSGSGTDFT
LTINNLQAEDVGVYYCQQYYSNPYTFGQTKLEIKRTDAQPAVYLFQPSPDQLHTGSASVVCLLNSFYPKDINVKMKVDGVIQDTGIQESVTEQDKDS
TYSLSSTLTMSSTEYLSHELYSCEITHKSLPSTLIKSFQRSECQRVD

SEQUENCE LISTING

```
<160> NUMBER OF SEQ ID NOS: 73

<210> SEQ ID NO 1
<211> LENGTH: 5
<212> TYPE: PRT
<213> ORGANISM: Artificial Sequence
<220> FEATURE:
<223> OTHER INFORMATION: CDR sequence

<400> SEQUENCE: 1

Ser Phe Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR sequence

<400> SEQUENCE: 2

Arg Val Asp Pro Tyr Asp Ser Glu Thr His Tyr Asn Gln Lys Phe Lys
1               5                   10                  15
Asp

<210> SEQ ID NO 3
<211> LENGTH: 9
<212> TYPE: PRT
<213> ORGANISM: Artificial Sequence
<220> FEATURE:
<223> OTHER INFORMATION: CDR sequence

<400> SEQUENCE: 3

Gln Phe Gly Phe Ser Trp Leu Ala Tyr
1               5
```

```
<210> SEQ ID NO 4
<211> LENGTH: 17
<212> TYPE: PRT
<213> ORGANISM: Artificial Sequence
<220> FEATURE:
<223> OTHER INFORMATION: CDR sequence

<400> SEQUENCE: 4

Lys Ser Ser Gln Ser Leu Leu Tyr Ser Ser Asn Gln Lys Asn Tyr Leu
1               5                   10                  15
Ala

<210> SEQ ID NO 5
<211> LENGTH: 7
<212> TYPE: PRT
<213> ORGANISM: Artificial Sequence
<220> FEATURE:
<223> OTHER INFORMATION: CDR sequence

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR sequence

<400> SEQUENCE: 6

Gln Gln Tyr Tyr Ser Asn Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR sequence

<400> SEQUENCE: 7

Asn Phe Gly Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: CDR sequence

<400> SEQUENCE: 8

Thr Ile Ser Ser Gly Ser Ser Tyr Ser Tyr Tyr Ser Asp Ser Val Lys
1               5                   10                  15
Gly

<210> SEQ ID NO 9
<211> LENGTH: 7
<212> TYPE: PRT
<213> ORGANISM: Artificial Sequence
<220> FEATURE:
<223> OTHER INFORMATION: CDR sequence

<400> SEQUENCE: 9

Gly Glu Ser Arg Phe Ala Tyr
```

```
1               5

<210> SEQ ID NO 10
<211> LENGTH: 16
<212> TYPE: PRT
<213> ORGANISM: Artificial Sequence
<220> FEATURE:
<223> OTHER INFORMATION: CDR sequence

<400> SEQUENCE: 10

Arg Ser Asn Lys Ser Leu Leu Tyr Glu Asp Gly Gln Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: CDR sequence

<400> SEQUENCE: 11

Leu Met Ser Thr Arg Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: CDR sequence

<400> SEQUENCE: 12

Gln Gln Leu Ile Glu Tyr Pro Leu Thr
1               5

<210> SEQ ID NO 13
<211> LENGTH: 5
<212> TYPE: PRT
<213> ORGANISM: Artificial Sequence
<220> FEATURE:
<223> OTHER INFORMATION: CDR sequence

<400> SEQUENCE: 13

Asn Phe Gly Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: CDR sequence

<400> SEQUENCE: 14

Thr Leu Ser Ser Gly Ser Ser Tyr Thr Tyr Tyr Ser Asp Ser Val Lys
1               5                   10                  15

Gly

<210> SEQ ID NO 15
<211> LENGTH: 7
<212> TYPE: PRT
<213> ORGANISM: Artificial Sequence
<220> FEATURE:
<223> OTHER INFORMATION: CDR sequence

<400> SEQUENCE: 15
```

Gly Glu Ser Arg Phe Ala Tyr
1               5

<210> SEQ ID NO 16
<211> LENGTH: 16
<212> TYPE: PRT
<213> ORGANISM: Artificial Sequence
<220> FEATURE:
<223> OTHER INFORMATION: CDR sequence

<400> SEQUENCE: 16

Arg Ser Ser Lys Ser Leu Leu Tyr Lys Asp Gly Lys Thr Tyr Leu Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDR sequence

<400> SEQUENCE: 17

Leu Met Ser Thr Arg Ala Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR sequence

<400> SEQUENCE: 18

Gln Gln Leu Ile Glu Tyr Pro Leu Thr
1               5

<210> SEQ ID NO 19
<211> LENGTH: 10
<212> TYPE: PRT
<213> ORGANISM: Artificial Sequence
<220> FEATURE:
<223> OTHER INFORMATION: CDR sequence

<400> SEQUENCE: 19

Gly Tyr Thr Phe Thr Ser Phe Trp Met Asn
1               5                   10

<210> SEQ ID NO 20
<211> LENGTH: 6
<212> TYPE: PRT
<213> ORGANISM: Artificial Sequence
<220> FEATURE:
<223> OTHER INFORMATION: CDR sequence

<400> SEQUENCE: 20

Asp Pro Tyr Asp Ser Glu
1               5

<210> SEQ ID NO 21
<211> LENGTH: 9
<212> TYPE: PRT
<213> ORGANISM: Artificial Sequence
<220> FEATURE:
<223> OTHER INFORMATION: CDR sequence

<400> SEQUENCE: 21

Gln Phe Gly Phe Ser Trp Leu Ala Tyr

```
<210> SEQ ID NO 22
<211> LENGTH: 17
<212> TYPE: PRT
<213> ORGANISM: Artificial Sequence
<220> FEATURE:
<223> OTHER INFORMATION: CDR sequence

<400> SEQUENCE: 22

Lys Ser Ser Gln Ser Leu Leu Tyr Ser Ser Asn Gln Lys Asn Tyr Leu
1               5                   10                  15
Ala

<210> SEQ ID NO 23
<211> LENGTH: 7
<212> TYPE: PRT
<213> ORGANISM: Artificial Sequence
<220> FEATURE:
<223> OTHER INFORMATION: CDR sequence

<400> SEQUENCE: 23

Trp Ala Ser Thr Arg Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: CDR sequence

<400> SEQUENCE: 24

Gln Gln Tyr Tyr Ser Asn Pro Tyr Thr
1               5

<210> SEQ ID NO 25
<211> LENGTH: 10
<212> TYPE: PRT
<213> ORGANISM: Artificial Sequence
<220> FEATURE:
<223> OTHER INFORMATION: CDR sequence

<400> SEQUENCE: 25

Gly Phe Pro Phe Ser Asn Phe Gly Met Ser
1               5                   10

<210> SEQ ID NO 26
<211> LENGTH: 6
<212> TYPE: PRT
<213> ORGANISM: Artificial Sequence
<220> FEATURE:
<223> OTHER INFORMATION: CDR sequence

<400> SEQUENCE: 26

Ser Ser Gly Ser Ser Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: CDR sequence

<400> SEQUENCE: 27
```

```
Gly Glu Ser Arg Phe Ala Tyr
1               5

<210> SEQ ID NO 28
<211> LENGTH: 16
<212> TYPE: PRT
<213> ORGANISM: Artificial Sequence
<220> FEATURE:
<223> OTHER INFORMATION: CDR sequence

<400> SEQUENCE: 28

Arg Ser Asn Lys Ser Leu Leu Tyr Glu Asp Gly Gln Thr Tyr Leu Asn
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: CDR sequence

<400> SEQUENCE: 29

Leu Met Ser Thr Arg Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDR sequence

<400> SEQUENCE: 30

Gln Gln Leu Ile Glu Tyr Pro Leu Thr
1               5

<210> SEQ ID NO 31
<211> LENGTH: 10
<212> TYPE: PRT
<213> ORGANISM: Artificial Sequence
<220> FEATURE:
<223> OTHER INFORMATION: CDR sequence

<400> SEQUENCE: 31

Gly Phe Thr Phe Asn Asn Phe Gly Met Ser
1               5                   10

<210> SEQ ID NO 32
<211> LENGTH: 6
<212> TYPE: PRT
<213> ORGANISM: Artificial Sequence
<220> FEATURE:
<223> OTHER INFORMATION: CDR sequence

<400> SEQUENCE: 32

Ser Ser Gly Ser Ser Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: CDR sequence

<400> SEQUENCE: 33

Gly Glu Ser Arg Phe Ala Tyr
```

-continued

```
<210> SEQ ID NO 34
<211> LENGTH: 16
<212> TYPE: PRT
<213> ORGANISM: Artificial Sequence
<220> FEATURE:
<223> OTHER INFORMATION: CDR sequence

<400> SEQUENCE: 34

Arg Ser Ser Lys Ser Leu Leu Tyr Lys Asp Gly Lys Thr Tyr Leu Asn
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: CDR sequence

<400> SEQUENCE: 35

Leu Met Ser Thr Arg Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: CDR sequence

<400> SEQUENCE: 36

Gln Gln Leu Ile Glu Tyr Pro Leu Thr
1               5

<210> SEQ ID NO 37
<211> LENGTH: 288
<212> TYPE: PRT
<213> ORGANISM: Human

<400> SEQUENCE: 37

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160
```

```
Arg Pro Ala Gly Gln Phe Gln Thr Leu Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```

<210> SEQ ID NO 38
<211> LENGTH: 288
<212> TYPE: PRT
<213> ORGANISM: Mouse

<400> SEQUENCE: 38

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255
```

Leu Gly Ala Ser Ala Met Gly Arg Arg Gly Ser Ala Asp Gly Leu Gln
            260                 265                 270

Gly Pro Arg Pro Arg His Glu Asp Gly His Cys Ser Trp Pro Leu
        275                 280                 285

<210> SEQ ID NO 39
<211> LENGTH: 288
<212> TYPE: PRT
<213> ORGANISM: Monkey

<400> SEQUENCE: 39

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Pro Pro Thr Phe Ser Pro Ala Leu Leu Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Arg Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285

<210> SEQ ID NO 40
<211> LENGTH: 288
<212> TYPE: PRT
<213> ORGANISM: Artificial Sequence
<220> FEATURE:
<223> OTHER INFORMATION: Chimeric PD-1

<400> SEQUENCE: 40

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Ser Pro Leu Thr Phe Ser Pro Ala Gln Leu Thr Val Gln Glu Gly Glu
            35                  40                  45

Asn Ala Thr Phe Thr Cys Ser Leu Ala Asp Ile Pro Asp Ser Phe Val
            50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Thr Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
            115                 120                 125

Pro Pro Asn Thr Gln Ile Asn Glu Ser Pro Arg Ala Glu Leu Val Val
            130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
            210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Arg His Glu Asp Gly His Cys Ser Trp Pro Leu
            275                 280                 285

<210> SEQ ID NO 41
<211> LENGTH: 288
<212> TYPE: PRT
<213> ORGANISM: Dog

<400> SEQUENCE: 41

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30

Ser Pro Leu Thr Phe Ser Pro Ala Gln Leu Thr Val Gln Glu Gly Glu
            35                  40                  45

Asn Ala Thr Phe Thr Cys Ser Leu Ala Asp Ile Pro Asp Ser Phe Val
            50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95
```

Val Thr Arg Leu Pro Asn Gly Arg Asp Phe His Met Ser Ile Val Ala
        100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
        130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
            180                 185                 190

Val Phe Pro Arg Ala Thr Arg Gly Ala Cys Val Cys Gly Ser Glu Asp
        195                 200                 205

Glu Pro Leu Lys Glu Gly Pro Asp Ala Ala Pro Val Phe Thr Leu Asp
        210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Pro
        275                 280                 285

<210> SEQ ID NO 42
<211> LENGTH: 116
<212> TYPE: PRT
<213> ORGANISM: Artificial Sequence
<220> FEATURE:
<223> OTHER INFORMATION: Caninized heavy chain variable region

<400> SEQUENCE: 42

Glu Val Gln Leu Val Glu Ser Gly Gly Asp Leu Val Lys Pro Val Gly
1               5                   10                  15

Ser Leu Arg Leu Ser Cys Val Ala Ser Gly Phe Thr Phe Asn Asn Phe
            20                  25                  30

Gly Met Ser Trp Val Arg Gln Ala Pro Gly Lys Gly Leu Gln Trp Val
        35                  40                  45

Ala Thr Leu Ser Ser Gly Ser Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Thr Arg Gly Glu Ser Arg Phe Ala Tyr Trp Gly Gln Gly Thr Leu Val
            100                 105                 110

Thr Val Ser Ala
        115

<210> SEQ ID NO 43
<211> LENGTH: 116
<212> TYPE: PRT
<213> ORGANISM: Artificial Sequence
<220> FEATURE:
<223> OTHER INFORMATION: Caninized heavy chain variable region

```
<400> SEQUENCE: 43

Glu Val Gln Leu Val Glu Ser Gly Gly Asp Leu Val Lys Pro Val Gly
1               5                   10                  15

Ser Leu Arg Leu Ser Cys Val Ala Ser Gly Phe Thr Phe Asn Asn Phe
            20                  25                  30

Gly Met Ser Trp Val Arg Gln Ala Pro Gly Lys Gly Leu Glu Trp Val
        35                  40                  45

Ala Thr Leu Ser Ser Gly Ser Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Thr Arg Gly Glu Ser Arg Phe Ala Tyr Trp Gly Gln Gly Thr Leu Val
            100                 105                 110

Thr Val Ser Ala
        115

<210> SEQ ID NO 44
<211> LENGTH: 116
<212> TYPE: PRT
<213> ORGANISM: Artificial Sequence
<220> FEATURE:
<223> OTHER INFORMATION: Caninized heavy chain variable region

<400> SEQUENCE: 44

Glu Val Gln Leu Val Glu Ser Gly Gly Asp Leu Val Lys Pro Val Gly
1               5                   10                  15

Ser Leu Arg Leu Ser Cys Ala Ala Ser Gly Phe Thr Phe Asn Asn Phe
            20                  25                  30

Gly Met Ser Trp Val Arg Gln Ala Pro Asp Lys Arg Leu Glu Trp Val
        35                  40                  45

Ala Thr Leu Ser Ser Gly Ser Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Thr Arg Gly Glu Ser Arg Phe Ala Tyr Trp Gly Gln Gly Thr Leu Val
            100                 105                 110

Thr Val Ser Ala
        115

<210> SEQ ID NO 45
<211> LENGTH: 112
<212> TYPE: PRT
<213> ORGANISM: Artificial Sequence
<220> FEATURE:
<223> OTHER INFORMATION: Caninized light chain variable region

<400> SEQUENCE: 45

Gly Val Val Ile Thr Gln Asp Pro Leu Ser Leu Ala Val Thr Pro Gly
1               5                   10                  15

Glu Leu Val Thr Ile Ser Cys Arg Ser Ser Lys Ser Leu Leu Tyr Lys
            20                  25                  30

Asp Gly Lys Thr Tyr Leu Asn Trp Tyr Leu Gln Lys Pro Gly Gln Thr
        35                  40                  45
```

```
Pro Arg Leu Leu Ile Tyr Leu Met Ser Thr Arg Ala Ser Gly Val Ser
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Ile Glu Tyr Pro Leu Thr Phe Gly Ala Gly Thr Lys Val Glu Leu Lys
            100                 105                 110
```

<210> SEQ ID NO 46
<211> LENGTH: 112
<212> TYPE: PRT
<213> ORGANISM: Artificial Sequence
<220> FEATURE:
<223> OTHER INFORMATION: Caninized light chain variable region

<400> SEQUENCE: 46

```
Gly Val Val Ile Thr Gln Asp Pro Leu Ser Leu Ala Val Thr Pro Gly
 1               5                  10                  15

Glu Leu Val Thr Ile Ser Cys Arg Ser Ser Lys Ser Leu Leu Tyr Lys
                 20                  25                  30

Asp Gly Lys Thr Tyr Leu Asn Trp Phe Leu Gln Lys Pro Gly Gln Thr
             35                  40                  45

Pro Arg Leu Leu Ile Tyr Leu Met Ser Thr Arg Ala Ser Gly Val Ser
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Ile Glu Tyr Pro Leu Thr Phe Gly Ala Gly Thr Lys Val Glu Leu Lys
            100                 105                 110
```

<210> SEQ ID NO 47
<211> LENGTH: 112
<212> TYPE: PRT
<213> ORGANISM: Artificial Sequence
<220> FEATURE:
<223> OTHER INFORMATION: Caninized light chain variable region

<400> SEQUENCE: 47

```
Gly Val Val Ile Thr Gln Asp Glu Leu Ser Leu Ala Val Thr Pro Gly
 1               5                  10                  15

Glu Leu Val Thr Ile Ser Cys Arg Ser Ser Lys Ser Leu Leu Tyr Lys
                 20                  25                  30

Asp Gly Lys Thr Tyr Leu Asn Trp Phe Leu Gln Lys Pro Gly Gln Thr
             35                  40                  45

Pro Gln Leu Leu Ile Tyr Leu Met Ser Thr Arg Ala Ser Gly Val Ser
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Ile Glu Tyr Pro Leu Thr Phe Gly Ala Gly Thr Lys Val Glu Leu Lys
            100                 105                 110
```

<210> SEQ ID NO 48
<211> LENGTH: 112
<212> TYPE: PRT
<213> ORGANISM: Artificial Sequence
<220> FEATURE:
<223> OTHER INFORMATION: Caninized light chain variable region

<400> SEQUENCE: 48

```
Gly Val Val Ile Thr Gln Asp Pro Leu Ser Leu Ala Val Thr Pro Gly
1               5                   10                  15

Glu Leu Val Thr Ile Ser Cys Arg Ser Ser Lys Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Ile Glu Tyr Pro Leu Thr Phe Gly Ala Gly Thr Lys Val Glu Leu Lys
            100                 105                 110
```

<210> SEQ ID NO 49
<211> LENGTH: 118
<212> TYPE: PRT
<213> ORGANISM: Artificial Sequence
<220> FEATURE:
<223> OTHER INFORMATION: Caninized heavy chain variable region

<400> SEQUENCE: 49

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Phe
            20                  25                  30

Trp Met Asn Trp Val Arg Leu Ala Pro Gly Ala Gly Leu Asp Trp Ile
        35                  40                  45

Gly Arg Val Asp Pro Tyr Asp Ser Glu Thr His Tyr Asn Gln Lys Phe
    50                  55                  60

Lys Asp Arg Val Ile Leu Thr Val Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Thr Gln Phe Gly Phe Ser Trp Leu Ala Tyr Trp Gly Gln Gly Thr
            100                 105                 110

Leu Val Thr Val Ser Ala
        115
```

<210> SEQ ID NO 50
<211> LENGTH: 118
<212> TYPE: PRT
<213> ORGANISM: Artificial Sequence
<220> FEATURE:
<223> OTHER INFORMATION: Caninized heavy chain variable region

<400> SEQUENCE: 50

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met Asn Trp Val Arg Leu Ala Pro Gly Ala Gly Leu Glu Trp Ile
        35                  40                  45
```

Gly Arg Val Asp Pro Tyr Asp Ser Glu Thr His Tyr Asn Gln Lys Phe
        50                  55                  60

Lys Asp Arg Ala Ile Leu Thr Val Asp Thr Ser Thr Ser Thr Ala Tyr
 65                  70                  75                  80

Met Glu Leu Ser Ser Leu Arg Ala Gly Asp Ile Ala Val Tyr Tyr Cys
                 85                  90                  95

Ala Thr Gln Phe Gly Phe Ser Trp Leu Ala Tyr Trp Gly Gln Gly Thr
                100                 105                 110

Leu Val Thr Val Ser Ala
        115

<210> SEQ ID NO 51
<211> LENGTH: 118
<212> TYPE: PRT
<213> ORGANISM: Artificial Sequence
<220> FEATURE:
<223> OTHER INFORMATION: Caninized heavy chain variable region

<400> SEQUENCE: 51

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Phe
                20                  25                  30

Trp Met Asn Trp Val Lys Leu Ala Pro Gly Gln Gly Leu Glu Trp Ile
            35                  40                  45

Gly Arg Val Asp Pro Tyr Asp Ser Glu Thr His Tyr Asn Gln Lys Phe
        50                  55                  60

Lys Asp Arg Ala Ile Leu Thr Val Asp Thr Ser Thr Ser Thr Ala Tyr
 65                  70                  75                  80

Met Glu Leu Ser Ser Leu Arg Ala Gly Asp Ile Ala Val Tyr Tyr Cys
                 85                  90                  95

Ala Thr Gln Phe Gly Phe Ser Trp Leu Ala Tyr Trp Gly Gln Gly Thr
                100                 105                 110

Leu Val Thr Val Ser Ala
        115

<210> SEQ ID NO 52
<211> LENGTH: 113
<212> TYPE: PRT
<213> ORGANISM: Artificial Sequence
<220> FEATURE:
<223> OTHER INFORMATION: Caninized light chain variable region

<400> SEQUENCE: 52

Glu Ile Val Met Thr Gln Ser Pro Gly Ser Leu Ala Gly Ser Ala Gly
 1               5                  10                  15

Glu Ser Val Ser Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Glu
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Asn Asn Leu Gln Ala Glu Asp Val Gly Val Tyr Tyr Cys Gln Gln
                 85                  90                  95

Tyr Tyr Ser Asn Pro Tyr Thr Phe Gly Gln Gly Thr Lys Leu Glu Ile
                100                 105                 110

Lys

<210> SEQ ID NO 53
<211> LENGTH: 113
<212> TYPE: PRT
<213> ORGANISM: Artificial Sequence
<220> FEATURE:
<223> OTHER INFORMATION: Caninized light chain variable region

<400> SEQUENCE: 53

Asp Ile Val Met Thr Gln Ser Pro Gly Ser Leu Ala Val Ser Ala Gly
1               5                   10                  15

Glu Ser Val Ser Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Glu
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Asn Val Gln Ala Glu Asp Val Gly Val Tyr Tyr Cys Gln Gln
                85                  90                  95

Tyr Tyr Ser Asn Pro Tyr Thr Phe Gly Gln Gly Thr Lys Leu Glu Ile
            100                 105                 110

Lys

<210> SEQ ID NO 54
<211> LENGTH: 113
<212> TYPE: PRT
<213> ORGANISM: Artificial Sequence
<220> FEATURE:
<223> OTHER INFORMATION: Caninized light chain variable region

<400> SEQUENCE: 54

Asp Ile Val Met Thr Gln Ser Pro Gly Ser Leu Ala Val Ser Ala Gly
1               5                   10                  15

Glu Lys Val Ser Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Asn Val Lys Ala Glu Asp Val Gly Val Tyr Tyr Cys Gln Gln
                85                  90                  95

Tyr Tyr Ser Asn Pro Tyr Thr Phe Gly Gln Gly Thr Lys Leu Glu Ile
            100                 105                 110

Lys

<210> SEQ ID NO 55
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 55

Glu Val Gln Leu Val Glu Ser Gly Gly Asp Leu Val Lys Pro Gly Gly
1               5                   10                  15

Ser Leu Lys Leu Ser Cys Val Ala Ser Gly Phe Pro Phe Ser Asn Phe
            20                  25                  30

Gly Met Ser Trp Val Arg Gln Thr Pro Asp Lys Arg Leu Glu Trp Val
            35                  40                  45

Ala Thr Ile Ser Ser Gly Ser Ser Tyr Ser Tyr Tyr Ser Asp Ser Val
        50                  55                  60

Lys Gly Arg Phe Thr Ile Ser Arg Asp Asn Ala Lys Asn Thr Leu Phe
65                  70                  75                  80

Leu Gln Met Asn Ser Leu Lys Ser Glu Asp Thr Ala Ile Phe Tyr Cys
                85                  90                  95

Ala Arg Gly Glu Ser Arg Phe Ala Tyr Trp Gly Gln Gly Thr Leu Val
            100                 105                 110

Thr Val Ser Ala
        115

<210> SEQ ID NO 56
<211> LENGTH: 112
<212> TYPE: PRT
<213> ORGANISM: Artificial Sequence
<220> FEATURE:
<223> OTHER INFORMATION: Light chain variable region

<400> SEQUENCE: 56

Asp Val Val Ile Thr Gln Asp Glu Leu Ser Asn Pro Val Thr Ser Gly
1               5                   10                  15

Glu Ser Val Ser Ile Ser Cys Arg Ser Asn Lys Ser Leu Leu Tyr Glu
            20                  25                  30

Asp Gly Gln Thr Tyr Leu Asn Trp Phe Leu Gln Arg Pro Gly Gln Ser
            35                  40                  45

Pro Gln Leu Leu Ile Tyr Leu Met Ser Thr Arg Ala Ser Gly Val Ser
        50                  55                  60

Asp Arg Phe Ser Gly Ser Gly Ser Gly Thr Asp Phe Thr Leu Glu Ile
65                  70                  75                  80

Ser Glu Val Arg Ala Glu Asp Val Gly Val Tyr Tyr Cys Gln Gln Leu
                85                  90                  95

Ile Glu Tyr Pro Leu Thr Phe Gly Ala Gly Thr Lys Leu Glu Leu Lys
            100                 105                 110

<210> SEQ ID NO 57
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 57

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Asn Phe
            20                  25                  30

Gly Met Ser Trp Val Arg Gln Asn Pro Asp Lys Arg Leu Glu Trp Val
            35                  40                  45

Ala Thr Leu Ser Ser Gly Ser Ser Tyr Thr Tyr Tyr Ser Asp Ser Val
        50                  55                  60

Lys Gly Arg Phe Thr Ile Ser Arg Asp Asn Ala Lys Asn Thr Leu Tyr
65                  70                  75                  80

```
Leu Gln Met Asn Ser Leu Lys Ser Glu Asp Thr Ala Met Tyr Tyr Cys
                85                  90                  95

Thr Arg Gly Glu Ser Arg Phe Ala Tyr Trp Gly Gln Gly Thr Leu Val
            100                 105                 110

Thr Val Ser Ala
        115

<210> SEQ ID NO 58
<211> LENGTH: 112
<212> TYPE: PRT
<213> ORGANISM: Artificial Sequence
<220> FEATURE:
<223> OTHER INFORMATION: Light chain variable region

<400> SEQUENCE: 58

Gly Val Val Ile Thr Gln Asp Glu Leu Ser Asn Pro Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Ile Glu Tyr Pro Leu Thr Phe Gly Ala Gly Thr Lys Leu Glu Leu Lys
            100                 105                 110

<210> SEQ ID NO 59
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 59

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Met Asn Trp Val Lys Leu Arg Pro Glu Gln Gly Leu Glu Trp Ile
        35                  40                  45

Gly Arg Val Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Gln Phe Gly Phe Ser Trp Leu Ala Tyr Trp Gly Gln Gly Thr
            100                 105                 110

Leu Val Thr Val Ser Ala
        115

<210> SEQ ID NO 60
<211> LENGTH: 113
<212> TYPE: PRT
```

<213> ORGANISM: Artificial Sequence
<220> FEATURE:
<223> OTHER INFORMATION: Light chain variable region

<400> SEQUENCE: 60

Asp Ile Val Met Ser Gln Ser Pro Ser Leu Ala Val Ser Val Gly
1               5                   10                  15

Glu Lys Val Thr Leu Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Asn Pro Tyr Thr Phe Gly Gly Thr Lys Leu Glu Ile
            100                 105                 110

Lys

<210> SEQ ID NO 61
<211> LENGTH: 358
<212> TYPE: PRT
<213> ORGANISM: Panda

<400> SEQUENCE: 61

Met Gly Ala Pro Arg Ala Pro Trp Pro Leu Val Trp Ala Val Leu Gln
1               5                   10                  15

Leu Gly Trp Trp Pro Gly Trp Leu Leu Asp Ser Pro Glu Arg Pro Trp
            20                  25                  30

Ser Pro Leu Thr Phe Ser Pro Ala Gln Leu Ala Val His Glu Gly Glu
        35                  40                  45

Asn Ala Thr Phe Thr Cys Ser Leu Ser Ser Val Pro Glu Ser Phe Val
    50                  55                  60

Leu Asn Trp Tyr Arg Met Ser Pro Arg Asn Gln Thr Asp Lys Leu Ala
65                  70                  75                  80

Ala Phe Gln Glu Asp Arg Ile Gln Pro Gly Pro Asp Arg Arg Phe His
                85                  90                  95

Val Thr Arg Leu Pro Asn Gly Arg Asp Phe His Met Ser Ile Val Ala
            100                 105                 110

Thr Gln Leu Ser Asp Ser Gly Thr Tyr Leu Cys Gly Ala Ile Tyr Leu
        115                 120                 125

Pro Pro Asn Thr Gln Ile Asn Glu Ser Pro Arg Ala Glu Leu Thr Val
    130                 135                 140

Lys Glu Arg Ile Leu Glu Pro Pro Thr Glu Ser Pro Ser Pro Pro
145                 150                 155                 160

Arg Ile Thr Asn Gln Leu Gln Gly Leu Val Ile Gly Ile Thr Ser Val
            165                 170                 175

Leu Val Gly Val Pro Leu Leu Leu Val Thr Trp Val Leu Ala Ala
        180                 185                 190

Ala Phe Pro Arg Ala Thr Arg Gly Thr Cys Ala Cys Gly Ser Glu Asp
    195                 200                 205

Ala Pro Leu Val Ser Phe Leu Pro Phe Ala Ala Pro Gly Trp Pro Arg
    210                 215                 220

Ser Ser Pro Val Pro Glu Phe Glu Gln Arg Asp Thr Arg Pro Trp Glu
225                 230                 235                 240

Gly Ala Trp Ser Thr Gly Pro Ala Leu Ala Leu Leu Trp Pro His Val
            245                 250                 255

Arg Thr Arg Ala Ser Val Pro Leu Pro Val Cys His Pro Glu Thr Thr
            260                 265                 270

Asp Ala Ser Leu Leu Leu Ser Leu Lys Lys Glu Gly Pro Ser Ala Ala
            275                 280                 285

Pro Val Phe Thr Val Asp Tyr Gly Glu Leu Asp Phe Gln Trp Arg Glu
            290                 295                 300

Lys Thr Pro Glu Pro Ser Ala Pro Cys Ala Pro Glu Gln Thr Glu Tyr
305                 310                 315                 320

Ala Thr Ile Val Phe Pro Ser Arg Pro Gly Ser Pro Gly Arg Arg Ala
            325                 330                 335

Ser Ala His Ser Pro Gln Gly Pro Gln Pro Leu Ser Pro Glu Asp Gly
            340                 345                 350

Pro Cys Pro Trp Pro Leu
            355

<210> SEQ ID NO 62
<211> LENGTH: 278
<212> TYPE: PRT
<213> ORGANISM: Feline

<400> SEQUENCE: 62

Met Gly Thr Pro Arg Ala Pro Trp Pro Leu Val Trp Ala Val Leu Gln
1               5                   10                  15

Leu Gly Trp Trp Pro Gly Trp Leu Leu Asp Ser Pro Tyr Arg Pro Trp
            20                  25                  30

Ser Pro Leu Thr Phe Ser Pro Ala Gln Leu Thr Val Leu Glu Gly Glu
            35                  40                  45

Asn Ala Thr Phe Val Cys His Leu Pro Asp Val Pro Glu Ser Phe Val
        50                  55                  60

Leu Asn Trp Tyr Arg Val Ser Pro Arg Asn Gln Thr Asp Lys Leu Ala
65              70                  75                  80

Ala Phe Gln Glu Asn His Thr Glu Pro Gly Lys Asp Arg Arg Phe Arg
            85                  90                  95

Val Thr Arg Leu Pro Ser Gly Gln Asp Phe His Thr Ile Leu Ala
            100                 105                 110

Ala Gln Leu Asn Asp Ser Gly Ile Tyr Leu Cys Gly Ala Ile Tyr Leu
            115                 120                 125

Pro Pro Asn Thr Gln Ile Tyr Glu Ser Pro Arg Ala Glu Leu Thr Val
            130                 135                 140

Lys Glu Arg Val Leu Glu Pro Pro Thr Glu Ser Pro Ser Pro Pro Pro
145                 150                 155                 160

Arg Leu Thr Gly Gln Gly Gln Gly Leu Val Val Gly Val Thr Ser Val
            165                 170                 175

Leu Val Gly Val Leu Leu Leu Leu Leu Thr Trp Val Leu Ala Ala
            180                 185                 190

Ala Phe Pro Arg Ala Thr Arg Gly Ala Cys Ala Cys Gly Ser Glu Asp
            195                 200                 205

Glu Pro Leu Lys Glu Gly Pro Ser Ala Ala Pro Val Phe Thr Val Asp
            210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
            245                 250                 255

Ser Arg Pro Gly Ser Pro Gly Pro Leu Pro Leu Arg Pro Glu Asp Gly
            260                 265                 270

Pro Cys Pro Trp Pro Leu
        275

<210> SEQ ID NO 63
<211> LENGTH: 468
<212> TYPE: PRT
<213> ORGANISM: Canis lupus familiaris

<400> SEQUENCE: 63

Met Glu Ser Val Phe Cys Trp Val Phe Leu Val Val Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Ser Tyr Tyr Met His Trp Ile Arg Gln Ala Pro Gly Lys Gly Leu
    50                  55                  60

Gln Arg Val Ala His Ile Arg Gly Asp Gly Arg Thr Thr His Tyr Ala
65                  70                  75                  80

Asp Ala Met Lys Gly Arg Phe Thr Ile Ser Arg Asp Asn Ala Lys Asn
                85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
        115                 120                 125

Gln Gly Thr Leu Val Thr Val Ser Ser Ala Ser Thr Thr Ala Pro Ser
130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

Ser Trp Asn Ser Gly Ser Leu Thr Ser Gly Val His Thr Phe Pro Ser
            180                 185                 190

Val Leu Gln Ser Ser Gly Leu His Ser Leu Ser Ser Met Val Thr Val
        195                 200                 205

Pro Ser Ser Arg Trp Pro Ser Glu Thr Phe Thr Cys Asn Val Val His
    210                 215                 220

Pro Ala Ser Asn Thr Lys Val Asp Lys Pro Val Phe Asn Glu Cys Arg
225                 230                 235                 240

Cys Thr Asp Thr Pro Pro Cys Pro Val Pro Glu Pro Leu Gly Gly Pro
                245                 250                 255

Ser Val Leu Ile Phe Pro Pro Lys Pro Lys Asp Ile Leu Arg Ile Thr
            260                 265                 270

Arg Thr Pro Glu Val Thr Cys Val Val Leu Asp Leu Gly Arg Glu Asp
        275                 280                 285

Pro Glu Val Gln Ile Ser Trp Phe Val Asp Gly Lys Glu Val His Thr
    290                 295                 300

Ala Lys Thr Gln Ser Arg Glu Gln Gln Phe Asn Gly Thr Tyr Arg Val
305                 310                 315                 320

Val Ser Val Leu Pro Ile Glu His Gln Asp Trp Leu Thr Gly Lys Glu

```
                325                 330                 335
Phe Lys Cys Arg Val Asn His Ile Asp Leu Pro Ser Pro Ile Glu Arg
            340                 345                 350
Thr Ile Ser Lys Ala Arg Gly Arg Ala His Lys Pro Ser Val Tyr Val
        355                 360                 365
Leu Pro Pro Ser Pro Lys Glu Leu Ser Ser Ser Asp Thr Val Ser Ile
    370                 375                 380
Thr Cys Leu Ile Lys Asp Phe Tyr Pro Pro Asp Ile Asp Val Glu Trp
385                 390                 395                 400
Gln Ser Asn Gly Gln Gln Glu Pro Glu Arg Lys His Arg Met Thr Pro
            405                 410                 415
Pro Gln Leu Asp Glu Asp Gly Ser Tyr Phe Leu Tyr Ser Lys Leu Ser
        420                 425                 430
Val Asp Lys Ser Arg Trp Gln Gln Gly Asp Pro Phe Thr Cys Ala Val
    435                 440                 445
Met His Glu Thr Leu Gln Asn His Tyr Thr Asp Leu Ser Leu Ser His
450                 455                 460
Ser Pro Gly Lys
465

<210> SEQ ID NO 64
<211> LENGTH: 473
<212> TYPE: PRT
<213> ORGANISM: Canis lupus familiaris

<400> SEQUENCE: 64

Met Glu Ser Val Leu Phe Trp Val Phe Leu Val Thr Ile Leu Lys Gly
1               5                   10                  15
Val Gln Gly Glu Val Arg Leu Val Glu Ser Gly Gly Thr Leu Val Lys
            20                  25                  30
Pro Gly Gly Ser Leu Lys Leu Ser Cys Val Ala Ser Gly Phe Thr Phe
        35                  40                  45
Arg Arg Tyr Ser Met Asp Trp Val Arg Gln Ala Pro Gly Lys Ser Leu
    50                  55                  60
Gln Trp Val Ala Gly Ile Asn Gly Asp Gly Thr Gly Ser Tyr Ser
65                  70                  75                  80
Gln Thr Val Lys Gly Arg Phe Thr Ile Ser Arg Asp Asn Ala Lys Asn
            85                  90                  95
Thr Leu Tyr Leu Gln Ile Asn Ser Leu Arg Ala Glu Asp Ser Ala Val
        100                 105                 110
Tyr Tyr Cys Ala Lys Ser Trp Ser Arg Asn Gly Asp Leu Asp Tyr Trp
    115                 120                 125
Gly Gln Gly Thr Leu Val Thr Val Ser Ser Ala Ser Thr Thr Ala Pro
130                 135                 140
Ser Val Phe Pro Leu Ala Pro Ser Cys Gly Ser Thr Ser Gly Ser Thr
145                 150                 155                 160
Val Ala Leu Ala Cys Leu Val Ser Gly Tyr Phe Pro Glu Pro Val Thr
            165                 170                 175
Val Ser Trp Asn Ser Gly Ser Leu Thr Ser Gly Val His Thr Phe Pro
        180                 185                 190
Ser Val Leu Gln Ser Ser Gly Leu Tyr Ser Leu Ser Ser Met Val Thr
    195                 200                 205
Val Pro Ser Ser Arg Trp Pro Ser Glu Thr Phe Thr Cys Asn Val Ala
210                 215                 220
```

```
His Pro Ala Ser Lys Thr Lys Val Asp Lys Pro Val Pro Lys Arg Glu
225                 230                 235                 240

Asn Gly Arg Val Pro Arg Pro Asp Cys Pro Lys Cys Pro Ala Pro
            245                 250                 255

Glu Met Leu Gly Gly Pro Ser Val Phe Ile Phe Pro Pro Lys Pro Lys
            260                 265                 270

Asp Thr Leu Leu Ile Ala Arg Thr Pro Glu Val Thr Cys Val Val Val
        275                 280                 285

Asp Leu Asp Pro Glu Asp Pro Glu Val Gln Ile Ser Trp Phe Val Asp
    290                 295                 300

Gly Lys Gln Met Gln Thr Ala Lys Thr Gln Pro Arg Glu Glu Gln Phe
305                 310                 315                 320

Asn Gly Thr Tyr Arg Val Val Ser Val Leu Pro Ile Gly His Gln Asp
                325                 330                 335

Trp Leu Lys Gly Lys Gln Phe Thr Cys Lys Val Asn Asn Lys Ala Leu
            340                 345                 350

Pro Ser Pro Ile Glu Arg Thr Ile Ser Lys Ala Arg Gly Gln Ala His
        355                 360                 365

Gln Pro Ser Val Tyr Val Leu Pro Pro Ser Arg Glu Glu Leu Ser Lys
    370                 375                 380

Asn Thr Val Ser Leu Thr Cys Leu Ile Lys Asp Phe Phe Pro Pro Asp
385                 390                 395                 400

Ile Asp Val Glu Trp Gln Ser Asn Gly Gln Gln Glu Pro Glu Ser Lys
                405                 410                 415

Tyr Arg Thr Thr Pro Pro Gln Leu Asp Glu Asp Gly Ser Tyr Phe Leu
            420                 425                 430

Tyr Ser Lys Leu Ser Val Asp Lys Ser Arg Trp Gln Arg Gly Asp Thr
        435                 440                 445

Phe Ile Cys Ala Val Met His Glu Ala Leu His Asn His Tyr Thr Gln
    450                 455                 460

Glu Ser Leu Ser His Ser Pro Gly Lys
465                 470

<210> SEQ ID NO 65
<211> LENGTH: 248
<212> TYPE: PRT
<213> ORGANISM: Canis lupus familiaris

<400> SEQUENCE: 65

Met Arg Phe Pro Ser Gln Leu Leu Gly Leu Leu Met Leu Trp Ile Pro
1               5                   10                  15

Gly Ser Gly Gly Asp Ile Val Met Thr Gln Thr Pro Pro Ser Leu Ser
            20                  25                  30

Val Ser Pro Arg Glu Pro Ala Ser Ile Ser Cys Arg Ala Ser Gln Ser
        35                  40                  45

Leu Leu His Ser Asn Gly Asn Thr Tyr Leu Asn Trp Phe Arg Gln Lys
    50                  55                  60

Pro Gly Gln Ser Pro Glu Gly Leu Ile Tyr Lys Val Ser Asn Arg Phe
65                  70                  75                  80

Thr Gly Val Ser Asp Arg Phe Ser Gly Ser Gly Ser Gly Thr Asp Phe
                85                  90                  95

Thr Leu Arg Ile Ser Arg Val Glu Ala Asp Asp Thr Gly Val Tyr Tyr
            100                 105                 110

Cys Gly Gln Gly Thr Gln Leu Pro Pro Thr Pro Ser Leu Trp Leu Thr
        115                 120                 125
```

Phe Gly Gln Gly Thr Lys Val Glu Ile Lys Arg Asn Asp Ala Gln Pro
            130                 135                 140

Ala Val Tyr Leu Phe Gln Pro Ser Pro Asp Gln Leu His Thr Gly Ser
145                 150                 155                 160

Ala Ser Val Val Cys Leu Leu Asn Ser Phe Tyr Pro Lys Asp Ile Asn
                165                 170                 175

Val Lys Trp Lys Val Asp Gly Val Ile Gln Asp Thr Gly Ile Gln Glu
            180                 185                 190

Ser Val Thr Glu Gln Asp Lys Asp Ser Thr Tyr Ser Leu Ser Ser Thr
            195                 200                 205

Leu Thr Met Ser Ser Thr Glu Tyr Leu Ser His Glu Leu Tyr Ser Cys
210                 215                 220

Glu Ile Thr His Lys Ser Leu Pro Ser Thr Leu Ile Lys Ser Phe Gln
225                 230                 235                 240

Arg Ser Glu Cys Gln Arg Val Asp
            245

<210> SEQ ID NO 66
<211> LENGTH: 335
<212> TYPE: PRT
<213> ORGANISM: Felis catus

<400> SEQUENCE: 66

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys

```
                    245                 250                 255
Ser Phe His Pro Pro Asp Ile Ala Val Glu Trp Glu Ile Thr Gly Gln
                260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
        290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 67
<211> LENGTH: 242
<212> TYPE: PRT
<213> ORGANISM: Felis catus

<400> SEQUENCE: 67

Met Arg Phe Pro Ala Gln Leu Leu Gly Leu Ile Met Leu Trp Ile Pro
1               5                   10                  15

Gly Ser Ser Gly Asp Ile Val Met Thr Gln Thr Pro Leu Ser Leu Ser
            20                  25                  30

Val Thr Pro Gly Glu Pro Ala Ser Ile Ser Cys Arg Ala Ser Gln Ser
        35                  40                  45

Leu Leu Tyr Ser Asp Gly Asn Thr Tyr Leu Asn Trp Tyr Leu Gln Lys
    50                  55                  60

Pro Gly Gln Ser Pro Arg Arg Leu Ile Tyr Leu Val Ser Asn Arg Asp
65                  70                  75                  80

Ser Gly Val Pro Asp Arg Phe Ser Gly Ser Gly Ser Gly Thr Asp Phe
                85                  90                  95

Thr Leu Arg Ile Ser Arg Val Glu Ala Asp Asp Val Gly Val Tyr Tyr
            100                 105                 110

Cys Gly Gln Gly Leu Gln His Pro Leu Thr Phe Gly Pro Gly Thr Lys
        115                 120                 125

Leu Glu Ile Lys Arg Ser Asp Ala Gln Pro Ser Val Phe Leu Phe Gln
    130                 135                 140

Pro Ser Leu Asp Glu Leu His Thr Gly Ser Ala Ser Ile Val Cys Ile
145                 150                 155                 160

Leu Asn Asp Phe Tyr Pro Lys Glu Val Asn Val Lys Trp Lys Val Asp
                165                 170                 175

Gly Val Val Gln Asn Lys Gly Ile Gln Glu Ser Thr Thr Glu Gln Asn
            180                 185                 190

Ser Lys Asp Ser Thr Tyr Ser Leu Ser Ser Thr Leu Thr Met Ser Ser
        195                 200                 205

Thr Glu Tyr Gln Ser His Glu Lys Phe Ser Cys Glu Val Thr His Lys
    210                 215                 220

Ser Leu Ala Ser Thr Leu Val Lys Ser Phe Asn Arg Ser Glu Cys Gln
225                 230                 235                 240

Arg Glu

<210> SEQ ID NO 68
<211> LENGTH: 474
<212> TYPE: PRT
<213> ORGANISM: Canis lupus familiaris

<400> SEQUENCE: 68
```

Met Glu Ser Val Leu Tyr Trp Val Phe Leu Val Ala Ile Leu Lys Gly
1               5                   10                  15

Val Gln Gly Asp Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
            35                  40                  45

Ser Ser Cys Ala Met Ser Trp Val Arg Gln Ser Pro Gly Lys Gly Pro
    50                  55                  60

Gln Trp Val Ala Thr Ile Arg Tyr Asp Gly Ser Asp Ile Tyr Tyr Ala
65                  70                  75                  80

Asp Ala Val Lys Gly Arg Phe Ser Ile Ser Arg Asp Asn Ala Lys Asn
                85                  90                  95

Thr Val Tyr Leu Gln Met Asn Ser Leu Arg Ala Glu Asp Thr Ala Val
                100                 105                 110

Tyr Tyr Cys Ala Lys Ala Pro Tyr Asp Ser Tyr His Tyr Gly Met
                115                 120                 125

Asp Tyr Trp Gly Pro Gly Thr Ser Leu Phe Val Ser Ser Ala Ser Thr
    130                 135                 140

Thr Ala Pro Ser Val Phe Pro Leu Ala Pro Ser Cys Gly Ser Gln Ser
145                 150                 155                 160

Gly Ser Thr Val Ala Leu Ala Cys Leu Val Ser Gly Tyr Ile Pro Glu
                165                 170                 175

Pro Val Thr Val Ser Trp Asn Ser Val Ser Leu Thr Ser Gly Val His
                180                 185                 190

Thr Phe Pro Ser Val Leu Gln Ser Ser Gly Leu Tyr Ser Leu Ser Ser
                195                 200                 205

Met Val Thr Val Pro Ser Ser Arg Trp Pro Ser Glu Thr Phe Thr Cys
                210                 215                 220

Asn Val Ala His Pro Ala Thr Asn Thr Lys Val Asp Lys Pro Val Ala
225                 230                 235                 240

Lys Glu Cys Glu Cys Lys Cys Asn Cys Asn Asn Cys Pro Cys Pro Gly
                245                 250                 255

Cys Gly Leu Leu Gly Gly Pro Ser Val Phe Ile Phe Pro Pro Lys Pro
                260                 265                 270

Lys Asp Ile Leu Val Thr Ala Arg Thr Pro Thr Val Thr Cys Val Val
                275                 280                 285

Val Asp Leu Asp Pro Glu Asn Pro Glu Val Gln Ile Ser Trp Phe Val
                290                 295                 300

Asp Ser Lys Gln Val Gln Thr Ala Asn Thr Gln Pro Arg Glu Glu Gln
305                 310                 315                 320

Ser Asn Gly Thr Tyr Arg Val Val Ser Val Leu Pro Ile Gly His Gln
                325                 330                 335

Asp Trp Leu Ser Gly Lys Gln Phe Lys Cys Lys Val Asn Asn Lys Ala
                340                 345                 350

Leu Pro Ser Pro Ile Glu Glu Ile Ile Ser Lys Thr Pro Gly Gln Ala
                355                 360                 365

His Gln Pro Asn Val Tyr Val Leu Pro Pro Ser Arg Asp Glu Met Ser
                370                 375                 380

Lys Asn Thr Val Thr Leu Thr Cys Leu Val Lys Asp Phe Phe Pro Pro
385                 390                 395                 400

Glu Ile Asp Val Glu Trp Gln Ser Asn Gly Gln Gln Glu Pro Glu Ser
                405                 410                 415

Lys Tyr Arg Met Thr Pro Pro Gln Leu Asp Glu Asp Gly Ser Tyr Phe
                420                 425                 430

Leu Tyr Ser Lys Leu Ser Val Asp Lys Ser Arg Trp Gln Arg Gly Asp
            435                 440                 445

Thr Phe Ile Cys Ala Val Met His Glu Ala Leu His Asn His Tyr Thr
        450                 455                 460

Gln Ile Ser Leu Ser His Ser Pro Gly Lys
465             470

<210> SEQ ID NO 69
<211> LENGTH: 470
<212> TYPE: PRT
<213> ORGANISM: Canis lupus familiaris

<400> SEQUENCE: 69

Met Glu Ser Val Leu Cys Trp Val Phe Leu Val Ser Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Asp Tyr Gly Met Ser Trp Val Arg Gln Ser Pro Gly Lys Gly Leu
    50                  55                  60

Gln Trp Val Ala Ala Val Ser Asn Arg Gly Asp Thr Tyr Tyr Ala Asp
65                  70                  75                  80

Ala Val Lys Gly Arg Phe Thr Ile Ser Arg Asp Asn Ala Lys Asn Thr
                85                  90                  95

Leu Tyr Leu Gln Met Ser Ser Leu Lys Ala Glu Asp Thr Ala Ile Tyr
            100                 105                 110

His Cys Val Thr Gly Val Trp Pro Arg His Tyr Tyr Gly Met Asp His
        115                 120                 125

Trp Gly Asn Gly Thr Ser Leu Phe Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu Tyr Ser Leu Ser Ser Thr Val
        195                 200                 205

Thr Val Pro Ser Ser Arg Trp Pro Ser Glu Thr Phe Thr Cys Asn Val
    210                 215                 220

Val His Pro Ala Ser Asn Thr Lys Val Asp Lys Pro Val Pro Lys Glu
225                 230                 235                 240

Ser Thr Cys Lys Cys Ile Ser Pro Cys Pro Val Pro Glu Ser Leu Gly
                245                 250                 255

Gly Pro Ser Val Phe Ile Phe Pro Pro Lys Pro Lys Asp Ile Leu Arg
            260                 265                 270

Ile Thr Arg Thr Pro Glu Ile Thr Cys Val Val Leu Asp Leu Gly Arg
        275                 280                 285

Glu Asp Pro Glu Val Gln Ile Ser Trp Phe Val Asp Gly Lys Glu Val
    290                 295                 300

His Thr Ala Lys Thr Gln Pro Arg Glu Gln Gln Phe Asn Ser Thr Tyr
305                 310                 315                 320

Arg Val Val Ser Val Leu Pro Ile Glu His Gln Asp Trp Leu Thr Gly
                325                 330                 335

Lys Glu Phe Lys Cys Arg Val Asn His Ile Gly Leu Pro Ser Pro Ile
            340                 345                 350

Glu Arg Thr Ile Ser Lys Ala Arg Gly Gln Ala His Gln Pro Ser Val
        355                 360                 365

Tyr Val Leu Pro Pro Ser Pro Lys Glu Leu Ser Ser Ser Asp Thr Val
    370                 375                 380

Thr Leu Thr Cys Leu Ile Lys Asp Phe Phe Pro Glu Ile Asp Val
385                 390                 395                 400

Glu Trp Gln Ser Asn Gly Gln Pro Glu Pro Glu Ser Lys Tyr His Thr
                405                 410                 415

Thr Ala Pro Gln Leu Asp Glu Asp Gly Ser Tyr Phe Leu Tyr Ser Lys
            420                 425                 430

Leu Ser Val Asp Lys Ser Arg Trp Gln Gln Gly Asp Thr Phe Thr Cys
        435                 440                 445

Ala Val Met His Glu Ala Leu Gln Asn His Tyr Thr Asp Leu Ser Leu
    450                 455                 460

Ser His Ser Pro Gly Lys
465                 470

<210> SEQ ID NO 70
<211> LENGTH: 110
<212> TYPE: PRT
<213> ORGANISM: Canis lupus familiaris

<400> SEQUENCE: 70

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp
            100                 105                 110

<210> SEQ ID NO 71
<211> LENGTH: 109
<212> TYPE: PRT
<213> ORGANISM: Canis lupus familiaris

<400> SEQUENCE: 71

Thr Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
            20                  25                  30

Pro Lys Asp Ile Asn Val Lys Trp Lys Val Asp Gly Val Ile Gln Asp
        35                  40                  45

Thr Gly Ile Gln Glu Ser Val Thr Glu Gln Asp Lys Asp Ser Thr Tyr
    50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
            85                  90                  95

Ile Lys Ser Phe Gln Arg Ser Glu Cys Gln Arg Val Asp
        100                 105

<210> SEQ ID NO 72
<211> LENGTH: 468
<212> TYPE: PRT
<213> ORGANISM: Artificial Sequence
<220> FEATURE:
<223> OTHER INFORMATION: Caninized heavy chain of 1B9

<400> SEQUENCE: 72

Met Glu Trp Ser Trp Val Phe Leu Phe Leu Leu Ser Val Ile Ala Gly
1               5                   10                  15

Val Gln Ser Glu Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Ser Phe Trp Met Asn Trp Val Arg Leu Ala Pro Gly Ala Gly Leu
    50                  55                  60

Asp Trp Ile Gly Arg Val Asp Pro Tyr Asp Ser Glu Thr His Tyr Asn
65                  70                  75                  80

Gln Lys Phe Lys Asp Arg Val Ile Leu Thr Val Asp Thr Ser Thr Ser
            85                  90                  95

Thr Ala Tyr Met Glu Leu Ser Ser Leu Arg Ala Gly Asp Ile Ala Val
        100                 105                 110

Tyr Tyr Cys Ala Thr Gln Phe Gly Phe Ser Trp Leu Ala Tyr Trp Gly
    115                 120                 125

Gln Gly Thr Leu Val Thr Val Ser Ala Ala Ser Thr Thr Ala Pro Ser
130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
            165                 170                 175

Ser Trp Asn Ser Gly Ser Leu Thr Ser Gly Val His Thr Phe Pro Ser
        180                 185                 190

Val Leu Gln Ser Ser Gly Leu Tyr Ser Leu Ser Ser Thr Val Thr Val
    195                 200                 205

Pro Ser Ser Arg Trp Pro Ser Glu Thr Phe Thr Cys Asn Val Val His
210                 215                 220

Pro Ala Ser Asn Thr Lys Val Asp Lys Pro Val Pro Lys Glu Ser Thr
225                 230                 235                 240

Cys Lys Cys Ile Ser Pro Cys Pro Val Pro Glu Ser Leu Gly Gly Pro
            245                 250                 255

Ser Val Phe Ile Phe Pro Pro Lys Pro Lys Asp Ile Leu Arg Ile Thr
        260                 265                 270

Arg Thr Pro Glu Ile Thr Cys Val Val Leu Asp Leu Gly Arg Glu Asp
    275                 280                 285

Pro Glu Val Gln Ile Ser Trp Phe Val Asp Gly Lys Glu Val His Thr
290                 295                 300

Ala Lys Thr Gln Pro Arg Glu Gln Gln Phe Asn Ser Thr Tyr Arg Val
305                 310                 315                 320

```
Val Ser Val Leu Pro Ile Glu His Gln Asp Trp Leu Thr Gly Lys Glu
            325                 330                 335

Phe Lys Cys Arg Val Asn His Ile Gly Leu Pro Ser Pro Ile Glu Arg
            340                 345                 350

Thr Ile Ser Lys Ala Arg Gly Gln Ala His Gln Pro Ser Val Tyr Val
            355                 360                 365

Leu Pro Pro Ser Pro Lys Glu Leu Ser Ser Asp Thr Val Thr Leu
            370                 375             380

Thr Cys Leu Ile Lys Asp Phe Phe Pro Glu Ile Asp Val Glu Trp
385                 390                 395                 400

Gln Ser Asn Gly Gln Pro Glu Pro Glu Ser Lys Tyr His Thr Thr Ala
            405                 410                 415

Pro Gln Leu Asp Glu Asp Gly Ser Tyr Phe Leu Tyr Ser Lys Leu Ser
            420                 425                 430

Val Asp Lys Ser Arg Trp Gln Gln Gly Asp Thr Phe Thr Cys Ala Val
            435                 440                 445

Met His Glu Ala Leu Gln Asn His Tyr Thr Asp Leu Ser Leu Ser His
            450                 455                 460

Ser Pro Gly Lys
465

<210> SEQ ID NO 73
<211> LENGTH: 243
<212> TYPE: PRT
<213> ORGANISM: Artificial Sequence
<220> FEATURE:
<223> OTHER INFORMATION: Caninized light chain of 1B9

<400> SEQUENCE: 73

Met Ser Val Leu Thr Gln Val Leu Ala Leu Leu Leu Leu Trp Leu Thr
1               5                   10                  15

Gly Ala Arg Cys Glu Ile Val Met Thr Gln Ser Pro Gly Ser Leu Ala
            20                  25                  30

Gly Ser Ala Gly Glu Ser Val Ser Ile Asn Cys Lys Ser Ser Gln Ser
            35                  40                  45

Leu Leu Tyr Ser Ser Asn Gln Lys Asn Tyr Leu Ala Trp Tyr Gln Gln
    50                  55                  60

Lys Pro Gly Glu Ser Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Asn Asn Leu Gln Ala Glu Asp Val Gly Val Tyr
            100                 105                 110

Tyr Cys Gln Gln Tyr Tyr Ser Asn Pro Tyr Thr Phe Gly Gln Gly Thr
            115                 120                 125

Lys Leu Glu Ile Lys Arg Thr Asp Ala Gln Pro Ala Val Tyr Leu Phe
            130                 135                 140

Gln Pro Ser Pro Asp Gln Leu His Thr Gly Ser Ala Ser Val Val Cys
145                 150                 155                 160

Leu Leu Asn Ser Phe Tyr Pro Lys Asp Ile Asn Val Lys Trp Lys Val
            165                 170                 175

Asp Gly Val Ile Gln Asp Thr Gly Ile Gln Glu Ser Val Thr Glu Gln
            180                 185                 190

Asp Lys Asp Ser Thr Tyr Ser Leu Ser Ser Thr Leu Thr Met Ser Ser
            195                 200                 205
```

```
Thr Glu Tyr Leu Ser His Glu Leu Tyr Ser Cys Glu Ile Thr His Lys
    210                 215                 220

Ser Leu Pro Ser Thr Leu Ile Lys Ser Phe Gln Arg Ser Glu Cys Gln
225                 230                 235                 240

Arg Val Asp
```

ANTI-PD-1 ANTIBODIES AND METHODS OF TREATING CANCER

CROSS-REFERENCE TO RELATED APPLICATIONS

This application is a divisional of U.S. application Ser. No. 17/324,751, filed on May 19, 2021, which is a continuation of International Application No. PCT/CN2019/119798, filed on Nov. 20, 2019, which claims the benefit of International Application No. PCT/CN2018/116211, filed on Nov. 19, 2018 under 35 U.S.C. § 365(b). The entire contents of the foregoing applications are incorporated herein by reference.

STATEMENT REGARDING SEQUENCE LISTING

The Sequence Listing associated with this application is provided in text form in lieu of a paper copy, and is hereby incorporated by reference into the specification. The name of the text file containing the Sequence Listing is 44835-0089002_ST25.txt. The text file is 78,458 bytes, and was created and submitted electronically via EFS-Web on Apr. 20, 2024.

TECHNICAL FIELD

This disclosure relates to anti-PD-1 (Programmed Cell Death Protein 1) antibodies and uses thereof.

BACKGROUND

Recent clinical and commercial success of anticancer antibodies has created great interest in antibody-based therapeutics in human. Clinical trials for human cancer that target PD-1 have achieved excellent results and drawn attention as a next-generation cancer therapy.

The number of cancer cases of domestic animals has also been rapidly increased in these days due to the increased longevity of pets and improved diagnosis in veterinary clinic. Cancer therapies for domestic animals, as well as those for humans, have progressed and surgical, radiation, and chemical therapies have been increasingly performed on these domestic animals. However, the development of antibody-based therapeutics for veterinary use is slow. There is a need for the next-generation cancer therapy in veterinary care.

SUMMARY

This disclosure relates to anti-PD-1 antibodies, antigen-binding fragment thereof, and the uses thereof.

In one aspect, the disclosure provides an antibody or antigen-binding fragment thereof that binds to PD-1 (Programmed Cell Death Protein 1) comprising:
  a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and
  a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence,
  wherein the selected VH CDRs 1, 2, and 3 amino acid sequences and the selected VL CDRs, 1, 2, and 3 amino acid sequences are one of the following:
  (1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;
  (2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;
  (3) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively.

In some embodiments, the CDRs are in Kabat numbering. In some embodiments, the CDRs are in Chothia numbering.

In some embodiments, the antibody or antigen-binding fragment specifically binds to canine PD-1. In some embodiments, the antibody or antigen-binding fragment binds to PD-1 of *Ailuropoda melanoleuca* (giant panda) or *Felis catus* (domestic cat).

In some embodiments, the antibody or antigen-binding fragment is a caninized antibody or antigen-binding fragment thereof. In some embodiments, the antibody or antigen-binding fragment is a felinized antibody or antigen-binding fragment thereof.

In one aspect, the disclosure provides a nucleic acid comprising a polynucleotide encoding a polypeptide comprising:
  (1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 52, 53, 54, or 60, binds to PD-1;
  (2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 49, 50, 51, or 59, binds to PD-1;
  (3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 56, binds to PD-1;
  (4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 55, binds to PD-1;

(5) an immunoglobulin heavy chain or a fragment thereof comprising a heavy chain variable region (VH) comprising CDRs 1, 2, and 3 comprising the amino acid sequences set forth in SEQ ID NOs: 13, 14, 15, respectively, and wherein the VH, when paired with a light chain variable region (VL) comprising the amino acid sequence set forth in SEQ ID NO: 45, 46, 47, 48 or 58 binds to PD-1;

(6) an immunoglobulin light chain or a fragment thereof comprising a VL comprising CDRs 1, 2, and 3 comprising the amino acid sequences set forth in SEQ ID NOs: 16, 17, 18, respectively, and wherein the VL, when paired with a VH comprising the amino acid sequence set forth in SEQ ID NO: 42, 43, 44 or 57 binds to PD-1.

In some embodiments, the CDRs are in Kabat numbering. In some embodiments, the CDRs are in Chothia numbering.

In some embodiments, the VH when paired with a VL specifically binds to canine PD-1, or the VL when paired with a VH specifically binds to canine PD-1.

In some embodiments, the immunoglobulin heavy chain or the fragment thereof is a caninized immunoglobulin heavy chain or a fragment thereof, and the immunoglobulin light chain or the fragment thereof is a caninized immunoglobulin light chain or a fragment thereof. In some embodiments, the immunoglobulin heavy chain or the fragment thereof is a felinized immunoglobulin heavy chain or a fragment thereof, and the immunoglobulin light chain or the fragment thereof is a felinized immunoglobulin light chain or a fragment thereof.

In some embodiments, the antibody or antigen-binding fragment binds to PD-1 of *Ailuropoda melanoleuca* (giant panda) or *Felis catus* (domestic cat).

In some embodiments, the nucleic acid is cDNA.

In one aspect, the disclosure also provides a vector comprising one or more of the nucleic acids as described herein, and/or a vector comprising two of the nucleic acids as described herein. In some embodiments, the vector encodes the VL region and the VH region that together bind to PD-1.

In another aspect, the disclosure provides a pair of vectors, wherein each vector comprises one of the nucleic acids as described herein, wherein together the pair of vectors encodes the VL region and the VH region that together bind to PD-1.

The disclosure also provides a cell comprising the vector as described herein, or the pair of vectors as described herein. In some embodiments, the cell is a CHO cell.

In some embodiments, the cell has one or more of the nucleic acids as described herein, or two of the nucleic acids as described herein. In some embodiments, the two nucleic acids together encode the VL region and the VH region that together bind to PD-1.

In one aspect, the disclosure also provides a method of producing an antibody or an antigen-binding fragment thereof. The method involve (a) culturing the cell as described herein under conditions sufficient for the cell to produce the antibody or the antigen-binding fragment; and (b) collecting the antibody or the antigen-binding fragment produced by the cell.

In one aspect, the disclosure provides an antibody or antigen-binding fragment thereof that binds to PD-1 comprising a heavy chain variable region (VH) comprising an amino acid sequence that is at least 90% identical to a selected VH sequence, and a light chain variable region (VL) comprising an amino acid sequence that is at least 90% identical to a selected VL sequence, wherein the selected VH sequence and the selected VL sequence are one of the following:

(1) the selected VH sequence is SEQ ID NOs: 49, 50, 51, or 59, and the selected VL sequence is SEQ ID NOs: 52, 53, 54, or 60;

(2) the selected VH sequence is SEQ ID NOs: 42, 43, 44, or 57, and the selected VL sequence is SEQ ID NOs: 45, 46, 47, 48, or 58;

(3) the selected VH sequence is SEQ ID NO: 55, and the selected VL sequence is SEQ ID NO: 56.

In some embodiments, the VH comprises the sequence of SEQ ID NO: 49 and the VL comprises the sequence of SEQ ID NO: 53. In some embodiments, the VH comprises the sequence of SEQ ID NO: 43 and the VL comprises the sequence of SEQ ID NO: 45.

In some embodiments, the antibody or antigen-binding fragment specifically binds to canine PD-1. In some embodiments, the antibody or antigen-binding fragment binds to PD-1 of *Ailuropoda melanoleuca* (giant panda) or *Felis catus* (domestic cat). In some embodiments, the antibody or antigen-binding fragment is a caninized antibody or antigen-binding fragment thereof. In some embodiments, the antibody or antigen-binding fragment is a felinized antibody or antigen-binding fragment thereof.

In one aspect, the disclosure provides an antibody-drug conjugate comprising the antibody or antigen-binding fragment thereof as described herein covalently bound to a therapeutic agent. In some embodiments, the therapeutic agent is a cytotoxic or cytostatic agent.

In one aspect, the disclosure provides a method of treating a subject having cancer, the method comprising administering a therapeutically effective amount of a composition comprising the antibody or antigen-binding fragment thereof as described herein, or the antibody-drug conjugate as described herein, to the subject.

In some embodiments, the subject has a solid tumor. In some embodiments, the cancer is unresectable melanoma or metastatic melanoma. In some embodiments, the cancer is non-small cell lung cancer (NSCLC), squamous cell carcinoma of the head and neck (SCCHN), head and neck cancer, renal cell carcinoma (RCC), melanoma, bladder cancer, gastric cancer, urothelial cancer, Merkel-cell carcinoma, triple-negative breast cancer (TNBC), or colorectal carcinoma.

In one aspect, the disclosure provides a method of decreasing the rate of tumor growth. The method involves contacting a tumor cell with an effective amount of a composition comprising an antibody or antigen-binding fragment thereof as described herein, or the antibody-drug conjugate as described herein.

In one aspect, the disclosure provides a method of killing a tumor cell. The method involves contacting a tumor cell with an effective amount of a composition comprising the antibody or antigen-binding fragment thereof as described herein, or the antibody-drug conjugate as described herein.

In one aspect, the disclosure provides a pharmaceutical composition comprising the antibody or antigen-binding fragment thereof as described herein, and a pharmaceutically acceptable carrier.

In another aspect, the disclosure provides a pharmaceutical composition comprising the antibody drug conjugate as described herein, and a pharmaceutically acceptable carrier.

In at least some aspects or embodiments, the antibody is a canine IgG antibody (e.g., a canine IgG1, IgG2, IgG3, or IgG4 antibody). In at least some aspects or embodiments, the antibody is a feline IgG antibody.

In at least some aspects or embodiments, the antibody or antigen-binding fragment is a single-chain variable fragment (scFV).

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

As used herein, the term "antibody" refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include, e.g., monoclonal antibodies, polyclonal antibodies, multi-specific antibodies (e.g., bi-specific antibodies), single-chain antibodies, chimeric antibodies, human antibodies, mouse antibodies, canine antibodies, feline antibodies, caninized antibodies, and felinized antibodies, etc. In some embodiments, an antibody can contain an Fc region of a canine antibody, a feline antibody, a mouse antibody, or a human antibody. The term antibody also includes derivatives, e.g., bi-specific antibodies, single-chain antibodies, diabodies, linear antibodies, and multi-specific antibodies formed from antibody fragments.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')$_2$, and Fv fragments.

The monoclonal antibodies herein specifically include "chimeric" antibodies. As used herein, the term "chimeric antibody" refers to an antibody (immunoglobulin) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, e.g., by genetic engineering, from antibody variable and constant region genes belonging to different species. For example, the variable segments of the genes from a mouse monoclonal antibody can be joined to canine constant segments. FIG. 2 shows a schematic representation of the general structure of one embodiment of a mouse:canine IgG. In this embodiment, the antigen binding site is derived from mouse while the Fc portion is canine.

As used herein, the term "human antibody" refers to an antibody that is encoded by an endogenous nucleic acid (e.g., rearranged human immunoglobulin heavy or light chain locus) present in a human.

As used herein, the term "canine antibody" refers to an antibody that is encoded by an endogenous nucleic acid (e.g., rearranged canine immunoglobulin heavy or light chain locus) present in a canine mammal (e.g., domestic dog). The antibody can be a naturally-occurring or recombinantly produced immunoglobulin composed of amino acid sequences representative of natural antibodies isolated from canines of various breeds. Canine antibodies are antibodies having variable and constant regions derived from canine germline immunoglobulin sequences. In some cases, the canine antibodies can include amino acid residues not encoded by canine germline immunoglobulin sequences (e.g., mutations introduced by random or site-specific mutagenesis in vitro or by somatic mutation in vivo). However, the term "canine antibody" is not intended to include antibodies in which CDR sequences derived from the germline of another mammalian species, such as a mouse, have been grafted onto canine framework sequences.

As used herein, the term "feline antibody" refers to an antibody that is encoded by an endogenous nucleic acid (e.g., rearranged feline immunoglobulin heavy or light chain locus) present in a feline mammal (e.g., domestic cat). The antibody can be a naturally-occurring or recombinantly produced immunoglobulin composed of amino acid sequences representative of natural antibodies isolated from felines of various breeds. Feline antibodies are antibodies having variable and constant regions derived from feline germline immunoglobulin sequences. The feline antibodies of the disclosure can include amino acid residues not encoded by feline germline immunoglobulin sequences. However, the term "feline antibody" is not intended to include antibodies in which CDR sequences derived from the germline of another mammalian species, such as a mouse, have been grafted onto feline framework sequences.

As used herein, the term "caninized antibody" refers to an antibody which contains minimal sequence derived from a non-canine (e.g., mouse, human) immunoglobulin and contains sequences derived from a canine immunoglobulin. In non-limiting examples, caninized antibodies are canine immunoglobulin sequences (recipient antibody) in which hypervariable region residues of the recipient are replaced by hypervariable region residues from a non-canine species (donor antibody) such as mouse having the desired specificity, affinity, and capacity. In some instances, framework region (FR) residues of the canine immunoglobulin sequences are replaced by corresponding non-canine residues. Furthermore, in some embodiments, caninized antibodies can include residues that are not found in the recipient antibody or in the donor antibody. These modifications are made to further refine antibody performance. In some embodiments, the caninized antibody includes substantially all of at least one, and typically two, variable domains, in which all or substantially all of the hypervariable regions correspond to those of a non-canine immunoglobulin sequence and all or substantially all of the FRs are those of a canine immunoglobulin sequence. The caninized antibody optionally also will comprise a complete, or at least a portion of an immunoglobulin constant region (Fc), typically that of a canine immunoglobulin sequence. FIG. 2 shows one embodiment showing speciation or caninization of a mouse IgG. In some embodiments, mouse CDRs are grafted onto canine frameworks. Caninized antibodies can be produced using molecular biology methods known in the art. Strategies for caninization of antibodies include, but are not limited to, the strategies disclosed in US20160264656; and U.S. Pat. No. 7,261,890B2; which are incorporated herein by reference in the entirety.

As used herein, the term "felinized antibody" refers to an antibody which contains minimal sequence derived from a non-feline (e.g., mouse, human) immunoglobulin and contains sequences derived from a feline immunoglobulin. In non-limiting examples, felinized antibodies are feline immunoglobulin sequences (recipient antibody) in which hypervariable region residues of the recipient are replaced by hypervariable region residues from a non-feline species (donor antibody) such as mouse having the desired specificity, affinity, and capacity. In some instances, framework region (FR) residues of the feline immunoglobulin sequences are replaced by corresponding non-feline residues. Furthermore, in some embodiments, felinized antibodies can include residues that are not found in the recipient antibody or in the donor antibody. These modifications are made to further refine antibody performance. In some embodiments, the felinized antibody can include substantially all of at least one, and typically two, variable domains, in which all or substantially all of the hypervariable regions correspond to those of a non-feline immunoglobulin sequence and all or substantially all of the FRs are those of a feline immunoglobulin sequence. The felinized antibody optionally also will comprise a complete, or at least a portion of an immunoglobulin constant region (Fc), typically that of a feline immunoglobulin sequence. Felinized antibodies can be produced using molecular biology methods known in the art.

A "parent" antibody herein is one that is encoded by an amino acid sequence used for the preparation of the variant antibody (e.g., chimeric antibody, caninized antibody or felinized antibody). In some embodiments, the parent antibody has a canine framework region and, if present, has canine antibody constant region(s). For example, the parent antibody can be a caninized or canine antibody. As another example, the parent antibody can be a felinized or feline antibody. In some other examples, the parent antibody is a murine monoclonal antibody or a panda antibody.

The term "caninization" is defined as a method for transferring non-canine antigen-binding amino acids from a donor antibody to a canine antibody acceptor framework to generate protein therapeutic treatments useful in canine mammals.

The term "felinization" is defined as a method for transferring non-feline antigen-binding amino acids from a donor antibody to a feline antibody acceptor framework to generate protein therapeutic treatments useful in feline mammals.

In some embodiments, the antibody can contain minimal sequence derived from an immunoglobulin of one spices (e.g., mouse, human, dog, or cat) and contains sequences derived from an immunoglobulin of *Ailuropoda melanoleuca* (giant panda). In non-limiting examples, the hypervariable (e.g., CDR) region residues of the recipient antibody are from a non-panda antibody (e.g., a donor antibody), e.g., a mouse, rat, or rabbit antibody, having the desired specificity, affinity, and capacity. In some embodiments, the Fv framework residues of the immunoglobulin have amino acid resides that are derived from the immunoglobulin of *Ailuropoda melanoleuca* (giant panda). In some embodiments, the antibody contains substantially all of at least one, and typically two, variable domains, in which all or substantially all of the hypervariable loops (CDRs) correspond to those of a non-panda (e.g., mouse) immunoglobulin and all or substantially all of the framework regions are those of a immunoglobulin of giant panda. The antibody can also contain at least a portion of an immunoglobulin constant region (Fc), typically, that of an immunoglobulin of giant panda.

In some embodiments, the antibody is collected from a mammal or produced in a cell culture (e.g., hybridoma cells). In some embodiments, the antibody is produced in a non-human cell (e.g., a mouse or hamster cell line). In some embodiments, the antibody is produced in a bacterial or yeast cell. In some embodiments, the antibody is produced in a transgenic non-human animal (e.g., a bovine, a rat, or a mouse) containing an unrearranged or rearranged immunoglobulin locus (e.g., heavy or light chain immunoglobulin locus).

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multimeric antibody" refers to an antibody that contains four or more (e.g., six, eight, or ten) immunoglobulin variable domains. In some embodiments, the multimeric antibody is able to crosslink one target molecule (e.g., PD-1) to at least one second target molecule (e.g., CTLA-4) on the surface of a mammalian cell (e.g., a canine T-cell, a feline T-cell).

As used herein, the terms "subject" and "patient" are used interchangeably throughout the specification and describe an animal, human or non-human, to whom treatment according to the methods of the present invention is provided. Veterinary and non-veterinary applications are contemplated by the present invention. In some embodiments, the subject is a mammal (e.g., a non-human mammal). The subjects can include but are not limited to mice, rats, hamsters, guinea-pigs, rabbits, ferrets, cats, dogs, giant panda, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule (e.g., PD-1) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a PD-1 molecule may be referred to as a PD-1-specific antibody or an anti-PD-1 antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 16 lists CDR sequences of mouse anti-dPD-1 antibodies (13-1B9, 12-4A7, 12-1D8) and CDR sequences of related anti-dPD-1 antibodies thereof as defined by Kabat numbering.

FIG. 17 lists CDR sequences of mouse anti-dPD-1 antibodies (13-1B9, 12-4A7, 12-1D8) and CDR sequences of related anti-dPD-1 antibodies thereof as defined by Chothia numbering.

FIG. 18 lists amino acid sequences of human PD-1 (hPD-1), canine PD-1 (dPD-1), mouse PD-1 (mPD-1), monkey PD-1 (rmPD-1), chimeric PD-1 (chidPD-1), panda PD-1 (pPD-1), and feline PD-1 (cPD-1).

FIG. 19 lists amino acid sequences of heavy chain variable regions and light chain variable regions of caninized anti-dPD-1 antibodies based on 1D8.

FIG. 20 lists amino acid sequences of heavy chain variable regions and light chain variable regions of caninized anti-dPD-1 antibodies based on 1B9.

FIG. 21 lists the amino acid sequence of the heavy chain variable regions and light chain variable regions of mouse anti-dPD-1 antibodies 13-1B9, 12-4A7, and 12-1D8.

FIG. 22 lists the amino acid sequence of the constant regions of canine antibodies and feline antibodies.

STATEMENT REGARDING SEQUENCE LISTING

Figure 1A:
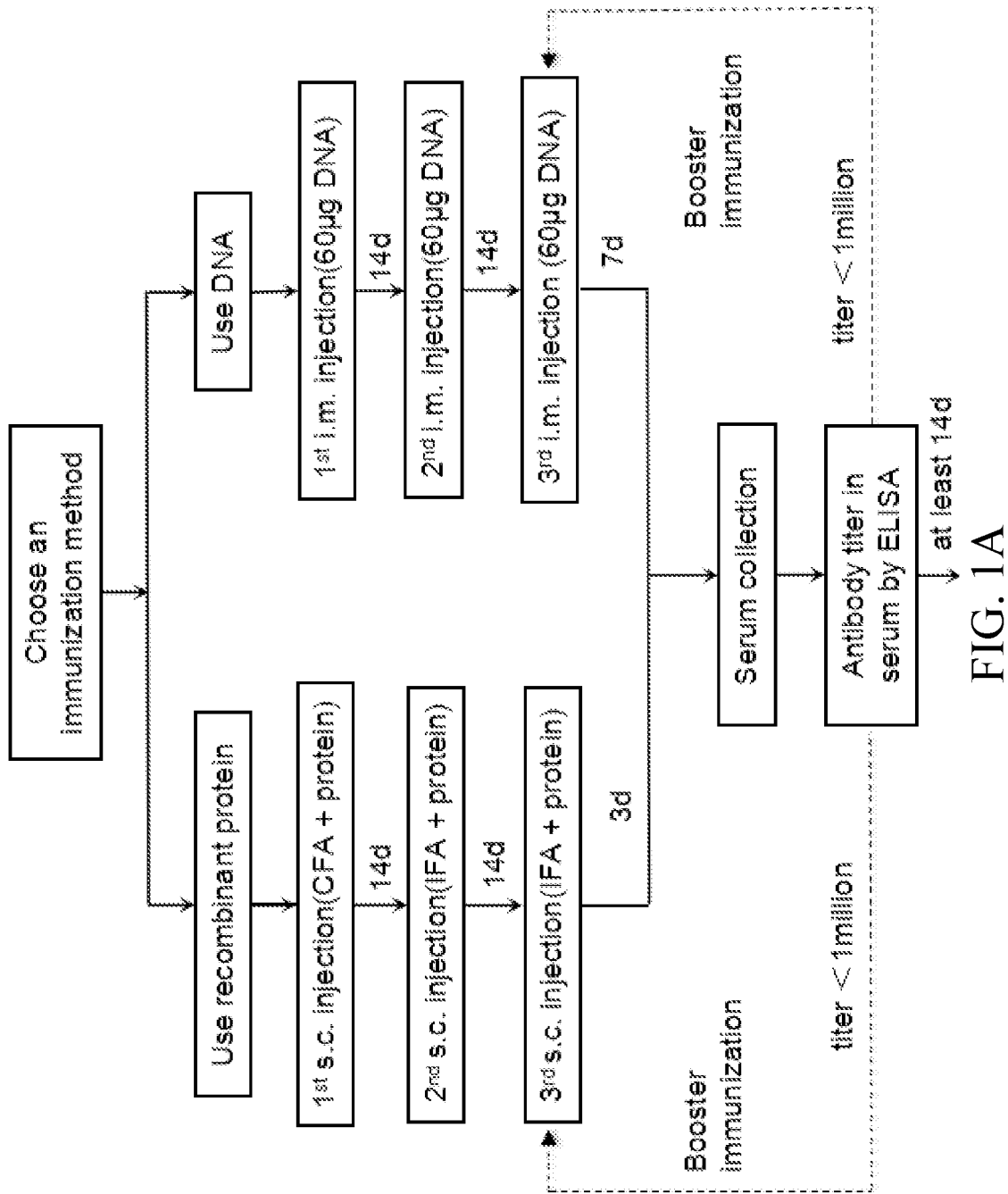
FIG. 1A is a flow chart showing the first part of an exemplary protocol of making anti-dPD-1 antibodies.

The Sequence Listing associated with this application is provided in text form in lieu of a paper copy, and is hereby incorporated by reference into the specification. The name of the text file containing the Sequence Listing is 44835-0089002_ST25.txt. The text file is 78,458 bytes, and was submitted electronically via EFS-Web.

DETAILED DESCRIPTION

The present disclosure provides examples of antibodies, antigen-binding fragment thereof, that bind to PD-1 (Programmed Cell Death Protein 1; also known as CD279).

PD-1 and Cancer

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

PD-1 (programmed death-1) is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells).

PD-1 is mainly expressed on the surfaces of T cells and primary B cells; two ligands of PD-1 (PD-L1 and PD-L2) are widely expressed in antigen-presenting cells (APCs). The interaction of PD-1 with its ligands plays an important role in the negative regulation of the immune response. Inhibition the binding between PD-1 and its ligand can make the tumor cells exposed to the killing effect of the immune system, and thus can reach the effect of killing tumor tissues and treating cancers.

PD-L1 is expressed on the neoplastic cells of many different cancers. By binding to PD-1 on T-cells leading to its inhibition, PD-L1 expression is a major mechanism by which tumor cells can evade immune attack. PD-L1 overexpression may conceptually be due to 2 mechanisms, intrinsic and adaptive. Intrinsic expression of PD-L1 on cancer cells is related to cellular/genetic aberrations in these neoplastic cells. Activation of cellular signaling including the AKT and STAT pathways results in increased PD-L1 expression. In primary mediastinal B-cell lymphomas, gene fusion of the MHC class II transactivator (CIITA) with PD-L1 or PD-L2 occurs, resulting in overexpression of these proteins. Amplification of chromosome 9p23-24, where PD-L1 and PD-L2 are located, leads to increased expression of both proteins in classical Hodgkin lymphoma. Adaptive mechanisms are related to induction of PD-L1 expression in the tumor microenvironment. PD-L1 can be induced on neoplastic cells in response to interferon γ. In microsatellite instability colon cancer, PD-L1 is mainly expressed on myeloid cells in the tumors, which then suppress cytotoxic T-cell function.

The use of PD-1 blockade to enhance anti-tumor immunity originated from observations in chronic infection models, where preventing PD-1 interactions reversed T-cell exhaustion. Similarly, blockade of PD-1 prevents T-cell PD-1/tumor cell PD-L1 or T-cell PD-1/tumor cell PD-L2 interaction, leading to restoration of T-cell mediated anti-tumor immunity.

A detailed description of PD-1, and the use of anti-PD-1 antibodies to treat cancers are described, e.g., in Topalian et al. "Safety, activity, and immune correlates of anti-PD-1 antibody in cancer." New England Journal of Medicine 366.26 (2012): 2443-2454; Hirano, Fumiya, et al. "Blockade of B7-H1 and PD-1 by monoclonal antibodies potentiates cancer therapeutic immunity." Cancer research 65.3 (2005): 1089-1096; Raedler, Lisa A. "Keytruda (pembrolizumab): first PD-1 inhibitor approved for previously treated unresectable or metastatic melanoma." American health & drug benefits 8. Spec Feature (2015): 96; Kwok, Gerry, et al. "Pembrolizumab (Keytruda)." (2016): 2777-2789; US 20170247454; U.S. Pat. Nos. 9,834,606 B and 8,728,474; each of which is incorporated by reference in its entirety.

The present disclosure provides several anti-PD-1 antibodies (e.g., caninized anti-dPD-1 antibodies), antigen-binding fragments thereof, and methods of using these anti-PD-1 antibodies and antigen-binding fragments to inhibit tumor growth and to treat cancers in various mammals, including canine animals (e.g., dogs), feline animals (e.g., cats), and/or Ursidae (e.g., giant panda).

Antibodies and Antigen Binding Fragments

The present disclosure provides anti-PD-1 antibodies and antigen-binding fragments thereof. In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain.

An antibody can comprise two identical copies of a light chain and two identical copies of a heavy chain. The heavy chains, which each contain one variable domain (or variable region, $V_H$) and multiple constant domains (or constant regions), bind to one another via disulfide bonding within their constant domains to form the "stem" of the antibody. The light chains, which each contain one variable domain (or variable region, $V_L$) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, camelid, dog, cat, or giant panda). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to increase potency. Thus, in one aspect, the disclosure further provides cells (e.g., T cells) that express the chimeric antigen receptors as described herein.

In some embodiments, the scFV has one heavy chain variable domain, and one light chain variable domain.

Anti-PD-1 Antibodies and Antigen-Binding Fragments

The disclosure provides antibodies and antigen-binding fragments thereof that specifically bind to PD-1 (e.g., canine PD-1). The antibodies and antigen-binding fragments described herein are capable of binding to PD-1 and can promote PD-1 signaling pathway thus increase immune response. The disclosure provides e.g., mouse anti-PD-1 antibodies 13-1B9 ("1B9"), 12-4A7 ("4A7"), and 12-1D8 ("1D8"), the chimeric antibodies thereof, and the caninized antibodies thereof (e.g., antibodies as shown in Table 1).

The CDR sequences for 1B9, and 1B9 derived antibodies (e.g., caninized antibodies and felinized antibodies) include CDRs of the heavy chain variable domain, SEQ ID NOs: 1-3, and CDRs of the light chain variable domain, SEQ ID NOs: 4-6 as defined by Kabat numbering. The CDRs can also be defined by Chothia system. Under the Chothia numbering, the CDR sequences of the heavy chain variable domain are set forth in SEQ ID NOs: 19-21 and CDR sequences of the light chain variable domain are set forth in SEQ ID NOs: 22-24.

Similarly, the CDR sequences for 4A7, and 4A7 derived antibodies include CDRs of the heavy chain variable domain, SEQ ID NOs: 7-9, and CDRs of the light chain variable domain, SEQ ID NOs: 10-12, as defined by Kabat numbering. Under Chothia numbering, the CDR sequences of the heavy chain variable domain are set forth in SEQ ID NOs: 25-27, and CDRs of the light chain variable domain are set forth in SEQ ID NOs: 28-30.

The CDR sequences for 1D8, and 1D8 derived antibodies include CDRs of the heavy chain variable domain, SEQ ID NOs: 13-15, and CDRs of the light chain variable domain, SEQ ID NOs: 16-18, as defined by Kabat numbering. Under Chothia numbering, the CDR sequences of the heavy chain variable domain are set forth in SEQ ID NOs: 31-33, and CDRs of the light chain variable domain are set forth in SEQ ID NOs: 34-36.

The amino acid sequences for heavy chain variable regions and light variable regions of the caninized antibodies are also provided. As there are different ways to caninize a mouse antibody (e.g., a sequence can be modified with different amino acid substitutions), the heavy chain and the light chain of an antibody can have more than one version of caninized sequences. The amino acid sequences for the heavy chain variable regions of caninized 1B9 antibody are set forth in SEQ ID NOs: 49-51. The amino acid sequences for the light chain variable regions of caninized 1B9 antibody are set forth in SEQ ID NOs: 52-54. Any of these heavy chain variable region sequences (SEQ ID NO: 49-51) can be paired with any of these light chain variable region sequences (SEQ ID NO: 52-54).

Similarly, the amino acid sequences for the heavy chain variable region of caninized 1D8 antibody are set forth in SEQ ID NOs: 42-44. The amino acid sequences for the light chain variable region of caninized 1D8 antibody are set forth in SEQ ID NOs: 45-48. Any of these heavy chain variable region sequences (SEQ ID NO: 42-44) can be paired with any of these light chain variable region sequences (SEQ ID NO: 45-48).

Caninization percentage means the percentage identity of the heavy chain or light chain variable region sequence as compared to a canine antibody sequences in International Immunogenetics Information System (IMGT) database. A top hit means that the heavy chain or light chain variable region sequence is closer to a particular species than to other species. In some embodiments, caninization percentage is greater than 80%, 81%, 82%, 83%, 84%, 85%, 86%, 87%, 88%, 89%, 90%, 91%, 92%, 93%, 94%, or 95%. A high caninization percentage often has various advantages, e.g., more safe and more effective in dogs, more likely to be tolerated, and/or less likely to have side effects.

Furthermore, in some embodiments, the antibodies or antigen-binding fragments thereof described herein can also contain one, two, or three heavy chain variable region CDRs selected from the group of SEQ ID NOs: 1-3, SEQ ID NOs: 7-9, SEQ ID NOs: 13-15, SEQ ID NOs: 19-21, SEQ ID NOs: 25-27, and SEQ ID NOs: 31-33; and/or one, two, or three light chain variable region CDRs selected from the group of SEQ ID NOs: 4-6, SEQ ID NOs: 10-12, SEQ ID NOs: 16-18, SEQ ID NOs: 22-24, SEQ ID NOs 28-30, and SEQ ID NOs: 34-36.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 16 (Kabat CDR) and FIG. 17 (Chothia CDR).

In some embodiments, the antibody or an antigen-binding fragment described herein can contain a heavy chain variable domain containing one, two, or three of the CDRs of SEQ ID NO: 1 with zero, one or two amino acid insertions, deletions, or substitutions; SEQ ID NO: 2 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 7 with zero, one or two amino acid insertions, deletions, or substitutions; SEQ ID NO: 8 with zero, one or two amino acid insertions, deletions, or substitutions; SEQ ID NO: 9 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 13 with zero, one or two amino acid insertions, deletions, or substitutions; SEQ ID NO: 14 with zero, one or two amino acid insertions, deletions, or substitutions; SEQ ID NO: 15 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 19 with zero, one or two amino acid insertions, deletions, or substitutions; SEQ ID NO: 20 with zero, one or two amino acid insertions, deletions, or substitutions; SEQ ID NO: 21 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 25 with zero, one or two amino acid insertions, deletions, or substitutions; SEQ ID NO: 26 with zero, one or two amino acid insertions, deletions, or substitutions; SEQ ID NO: 27 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 31 with zero, one or two amino acid insertions, deletions, or substitutions; SEQ ID NO: 32 with zero, one or two amino acid insertions, deletions, or substitutions; SEQ ID NO: 33 with zero, one or two amino acid insertions, deletions, or substitutions.

In some embodiments, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 5 with zero, one or two amino acid insertions, deletions, or substitutions; SEQ ID NO: 6 with zero, one or two amino acid insertions, deletions, or substitutions.

In some embodiments, the antibody or an antigen-binding fragment described herein can contain a light chain variable domain containing one, two, or three of the CDRs of SEQ ID NO: 10 with zero, one or two amino acid insertions, deletions, or substitutions; SEQ ID NO: 11 with zero, one or two amino acid insertions, deletions, or substitutions; SEQ ID NO: 12 with zero, one or two amino acid insertions, deletions, or substitutions.

In some embodiments, the antibody or an antigen-binding fragment described herein can contain a light chain variable domain containing one, two, or three of the CDRs of SEQ ID NO: 16 with zero, one or two amino acid insertions, deletions, or substitutions; SEQ ID NO: 17 with zero, one or two amino acid insertions, deletions, or substitutions; SEQ ID NO: 18 with zero, one or two amino acid insertions, deletions, or substitutions.

In some embodiments, the antibody or an antigen-binding fragment described herein can contain a light chain variable domain containing one, two, or three of the CDRs of SEQ ID NO: 22 with zero, one or two amino acid insertions, deletions, or substitutions; SEQ ID NO: 23 with zero, one or two amino acid insertions, deletions, or substitutions; SEQ ID NO: 24 with zero, one or two amino acid insertions, deletions, or substitutions.

In some embodiments, the antibody or an antigen-binding fragment described herein can contain a light chain variable domain containing one, two, or three of the CDRs of SEQ ID NO: 28 with zero, one or two amino acid insertions, deletions, or substitutions; SEQ ID NO: 29 with zero, one or two amino acid insertions, deletions, or substitutions; SEQ ID NO: 30 with zero, one or two amino acid insertions, deletions, or substitutions.

In some embodiments, the antibody or an antigen-binding fragment described herein can contain a light chain variable domain containing one, two, or three of the CDRs of SEQ ID NO: 34 with zero, one or two amino acid insertions, deletions, or substitutions; SEQ ID NO: 35 with zero, one or two amino acid insertions, deletions, or substitutions; SEQ ID NO: 36 with zero, one or two amino acid insertions, deletions, or substitutions.

The insertions, deletions, and substitutions can be within the CDR sequence, or at one or both terminal ends of the CDR sequence.

The disclosure also provides antibodies or antigen-binding fragments thereof that bind to PD-1 (e.g., canine PD-1). The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence is SEQ ID NOs: 49, 50, 51 or 59, and the selected VL sequence is SEQ ID NOs: 52, 53, 54, or 60. In some embodiments, the selected VH sequence is SEQ ID NOs: 42, 43, 44, or 57 and the selected VL sequence is SEQ ID NOs: 45, 46, 47, 48, or 58. In some embodiments, the selected VH sequence is SEQ ID NO: 55, and the selected VL sequence is SEQ ID NO: 56.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The disclosure also provides nucleic acid comprising a polynucleotide encoding a polypeptide comprising an immunoglobulin heavy chain or an immunoglobulin light chain. The immunoglobulin heavy chain or immunoglobulin light chain comprises CDRs as shown in FIG. 16 or FIG. 17, or have sequences as shown in FIGS. 19-21. When the polypeptides are paired with corresponding polypeptide (e.g., a corresponding heavy chain variable region or a corresponding light chain variable region), the paired polypeptides bind to PD-1 (e.g., canine PD-1).

The anti-PD-1 antibodies and antigen-binding fragments can also be antibody variants (including derivatives and conjugates) of antibodies or antibody fragments and multi-specific (e.g., bi-specific) antibodies or antibody fragments. Additional antibodies provided herein are polyclonal, monoclonal, multi-specific (multimeric, e.g., bi-specific), human antibodies, canine antibodies, feline antibodies, panda antibodies, chimeric antibodies (e.g., human-mouse chimera, canine-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG1, IgG2, IgG3, IgG4, IgA1, and IgA2), or subclass. In some embodiments, the antibody or antigen-binding fragment thereof is an IgG antibody or antigen-binding fragment thereof (e.g., canine, feline, or panda antibody).

In some embodiments, the antibody described herein is a canine or caninized IgG antibody (e.g., IgG1, IgG2, IgG3, or IgG4). For example, the antibody can have a canine IgG constant regions, including CL, CH1, CH2, and/or CH3. In some embodiments, the antibody is a feline or felinized IgG antibody. For example, the antibody can have a feline IgG constant regions, including CL, CH1, CH2, and/or CH3. In some embodiments, the antibody is a panda IgG antibody. In some cases, it can have constant regions (e.g., CL, CH1, CH2, and/or CH3) of a panda IgG antibody.

Fragments of antibodies are suitable for use in the methods provided so long as they retain the desired affinity and specificity of the full-length antibody. Thus, a fragment of an antibody that binds to PD-1 will retain an ability to bind to PD-1. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains (or regions) of antibody, wherein these domains are present in a single polypeptide chain. Generally, the scFv polypeptide further comprises a polypeptide linker between the VH and VL domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites. The fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified IgG$_1$ molecules) spontaneously form protein aggregates containing antibody homodimers and other higher-order antibody multimers.

Alternatively, antibody homodimers may be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acethylthio-acetate) can be used to form antibody multimers. An exemplary protocol for the formation of antibody homodimers is described in Ghetie et al. (*Proc.*

*Natl. Acad. Sci. U.S.A.* 94: 7509-7514, 1997). Antibody homodimers can be converted to Fab' 2 homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (Science 229:81, 1985) describes a procedure where intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as canine serum albumin). The conjugation of a stabilizing molecule can increase the half-life or extend the biological activity of an antibody or an antigen-binding fragment in vitro (e.g., in tissue culture or when stored as a pharmaceutical composition) or in vivo.

In some embodiments, the antibodies or antigen-binding fragments described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

Antibody Characteristics

The antibodies or antigen-binding fragments thereof described herein can block the binding between PD-1 and PD-L1 and/or the binding between PD-1 and PD-L2.

In some embodiments, by binding to PD-1, the antibody can inhibit PD-1 signaling pathway and upregulates the immune response. Thus, in some embodiments, the antibodies or antigen-binding fragments thereof as described herein are PD-1 antagonist. In some embodiments, the antibodies or antigen-binding fragments thereof are PD-1 agonist. In some embodiments, the antibodies or antigen-binding fragments thereof can block the binding between canine PD-1 and canine PD-L1, feline PD-1 and feline PD-L1, and/or panda PD-1 and panda PD-L1.

In some embodiments, the antibodies or antigen-binding fragments thereof as described herein can increase immune response, activity or number of T cells (e.g., CD8+ and/or CD4+ cells) by at least 10%, 20%, 30%, 40%, 50%, 60%, 70%, 80%, 90%, 100%, 2 folds, 3 folds, 5 folds, 10 folds, or 20 folds. In some embodiments, the antibodies or antigen-binding fragments thereof as described herein can decrease the activity or number of T cells by at least 10%, 20%, 30%, 40%, 50%, 60%, 70%, 80%, 90%, 100%, 2 folds, 3 folds, 5 folds, 10 folds, or 20 folds.

In some implementations, the antibody (or antigen-binding fragments thereof) specifically binds to PD-1 (e.g., canine PD-1, feline PD-1, panda PD-1, monkey PD-1, mouse PD-1, and/or chimeric PD-1) with a dissociation rate (koff) of less than $0.1\ s^{-1}$, less than $0.01\ s^{-1}$, less than $0.001\ s^{-1}$, less than $0.0001\ s^{-1}$, or less than $0.00001\ s^{-1}$. In some embodiments, the dissociation rate (koff) is greater than $0.01\ s^{-1}$, greater than $0.001\ s^{-1}$, greater than $0.0001\ s^{-1}$, greater than $0.00001\ s^{-1}$, or greater than $0.000001\ s^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD is less than $1\times10^{-6}$M, less than $1\times10^{-7}$M, less than $1\times10^{-8}$M, less than $1\times10^{-9}$M, or less than $1\times10^{-10}$ M. In some embodiments, the KD is less than 50 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1\times10^{-7}$M, greater than $1\times10^{-8}$M, greater than $1\times10^{-9}$M, greater than $1\times10^{-10}$ M, greater than $1\times10^{-11}$ M, or greater than $1\times10^{-12}$ M. In some embodiments, the antibody binds to canine PD-1 with KD less than or equal to about 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM.

General techniques for measuring the affinity of an antibody for an antigen include, e.g., ELISA, RIA, and surface plasmon resonance (SPR). In some embodiments, the antibody binds to canine PD-1 (SEQ ID NO: 41), feline PD-1 (SEQ ID NO: 62), panda PD-1 (SEQ ID NO: 31), human PD-1 (SEQ ID NO: 37), monkey PD-1 (e.g., rhesus macaque PD-1, SEQ ID NO: 39), chimeric PD-1 (SEQ ID NO: 40), and/or mouse PD-1 (SEQ ID NO: 38). In some embodiments, the antibody does not bind to canine PD-1 (SEQ ID NO: 41), feline PD-1 (SEQ ID NO: 62), panda PD-1 (SEQ ID NO: 31), human PD-1 (SEQ ID NO: 37), monkey PD-1

(e.g., rhesus macaque PD-1, SEQ ID NO: 39), chimeric PD-1 (SEQ ID NO: 40), and/or mouse PD-1 (SEQ ID NO: 38).

In some embodiments, the EC50 for the binding activity with canine PD-1, feline PD-1, or panda PD-1 is less than 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM. In some embodiments, the EC50 for the binding activity with canine PD-1, feline PD-1, or panda PD-1 is greater than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM. As used herein, the term "EC50" refers to the concentration for inducing half maximal effective response. At the EC50 concentration, an agent (e.g., a drug, antibody or toxicant) induces a response halfway between the baseline and maximum after a specified exposure time. "EC50" for the binding activity refers to the concentration of an agent (e.g., a drug, antibody or toxicant) which provides a binding activity halfway between the baseline and maximum binding activity.

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

As IgG can be described as a multi-domain protein, the melting curve sometimes shows two transitions, with a first denaturation temperature, Tm D1, and a second denaturation temperature Tm D2. The presence of these two peaks often indicate the denaturation of the Fc domains (Tm D1) and Fab domains (Tm D2), respectively. When there are two peaks, Tm usually refers to Tm D2. Thus, in some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI(\%)=[1-(Ti-T0)/(Vi-V0)]\times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the antibodies or antigen-binding fragments thereof as described herein are PD-1 antagonist. In some embodiments, the antibodies or antigen binding fragments decrease PD-1 signal transduction in a target cell that expresses PD-1.

In some embodiments, the antibodies or antigen binding fragments enhance CD4+ effector T cell function, for example, by increasing CD4+ effector T cell proliferation and/or increasing gamma interferon production by the CD4+ effector T cell (e.g., as compared to proliferation and/or cytokine production prior to treatment with the antibodies or antigen binding fragments). In some embodiments, the cytokine is gamma interferon. In some embodiments, the antibodies or antigen binding fragments increase number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with antibodies or antigen binding fragments. In some embodiments, the antibodies or antigen binding fragments increase number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment.

In some embodiments, the antibodies or antigen binding fragments increase number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment. In some embodiments, the antibodies or antigen binding fragments increase number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-PD-1 antibody (e.g., anti-canine PD-1 antibody).

In some embodiments, the antibodies or antigen binding fragments enhance memory T cell function, for example by increasing memory T cell proliferation and/or increasing cytokine (e.g., gamma interferon) production by the memory cell.

In some embodiments, the antibodies or antigen binding fragments inhibit Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the antibodies or antigen binding fragments reduce the number of intratumoral (infiltrating) Treg (e.g., total number of Treg or e.g., percentage of Fox3p+ cells in CD4+ cells).

In some embodiments, the antibodies or antigen binding fragments are depleting anti-PD-1 antibody (e.g., depletes cells that express canine PD-1). In some embodiments, the antibodies or antigen binding fragments deplete cells that express PD-1 (e.g., canine PD-1) in vitro. In some embodiments, the PD-1 expressing cells are CD4+ effector T cells, or Treg cells. In some embodiments, depleting is by ADCC and/or phagocytosis.

In some embodiments, the antibodies or antigen binding fragments have a functional Fc region. In some embodiments, effector function of a functional Fc region is antibody-dependent cell-mediated cytotoxicity (ADCC). In some embodiments, effector function of a functional Fc region is phagocytosis. In some embodiments, effector function of a functional Fc region is ADCC and phagocytosis. In some embodiments, the Fc region is of canine IgG (e.g., IgG1, IgG2, IgG3, or IgG4).

In some embodiments, the antibodies or antigen binding fragments do not induce apoptosis in PD-1-expressing cells (e.g., Treg).

In some embodiments, the antibodies or antigen binding fragments do not have a functional Fc region. For example, the antibodies or antigen binding fragments are Fab, Fab', F(ab')2, and Fv fragments.

Methods of Making Anti-PD-1 Antibodies

An isolated fragment of PD-1 (e.g., canine PD-1, feline PD-1, or panda PD-1) can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of PD-1 and encompasses an epitope of the protein such that an antibody raised against the peptide forms a specific immune complex with the protein. As described above, the full length sequence of canine PD-1 is known in the art (SEQ ID NO: 41).

An immunogen typically is used to prepare antibodies by immunizing a suitable subject (e.g., a mouse, or a transgenic animal). An appropriate immunogenic preparation can contain, for example, a recombinantly-expressed or a chemically-synthesized polypeptide (e.g., a fragment of canine PD-1). The preparation can further include an adjuvant, such as Freund's complete or incomplete adjuvant, or a similar immunostimulatory agent.

Polyclonal antibodies can be prepared as described above by immunizing a suitable subject with a PD-1 polypeptide, or an antigenic peptide thereof (e.g., part of PD-1) as an immunogen. The antibody titer in the immunized subject can be monitored over time by standard techniques, such as with an enzyme-linked immunosorbent assay (ELISA) using the immobilized PD-1 polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a canine, feline, caninized, felinized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., PD-1. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, dogs, cats, pandas, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human, canine, or feline antibodies.

The present disclosure also further provides cells and cell lines expressing antibodies described herein. Representative host cells include e.g., bacterial, yeast, mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) Int. Rev. Immunol. 10(2-3):103-112). Antibodies can also be produced in transgenic animals (Houdebine (2002) Curr. Opin. Biotechnol. 13(6):625-629) and transgenic plants (Schillberg et al. (2003) Cell Mol. Life Sci. 60(3): 433-45).

Ordinarily, amino acid sequence variants of the canine, caninized, feline, felinized or chimeric anti-PD-1 antibody will contain an amino acid sequence having at least 75%, 80%, 85%, 90%, 95%, 96%, 97%, 98%, or 99% percent identity with a sequence present in the light or heavy chain of the original antibody.

Identity or homology with respect to an original sequence is usually the percentage of amino acid residues present within the candidate sequence that are identical with a sequence present within the canine, caninized, feline, felinized, or chimeric anti-PD-1 antibody or fragment, after aligning the sequences and introducing gaps, if necessary, to achieve the maximum percent sequence identity, and not considering any conservative substitutions as part of the sequence identity.

Additional modifications to the anti-PD-1 antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the anti-PD-1 antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

Speciation of Antibodies

The generation of anti-drug antibodies (ADAs) can been associated with loss of efficacy for biotherapeutic protein including monoclonal antibodies. Comprehensive evaluation of the literature has shown that speciation of monoclonal antibodies can reduce the propensity for mAbs to be immunogenic. To help mitigate risks associated with ADA formation for the mouse anti PD-1 monoclonal antibodies provided herein, a speciation strategy (e.g., caninization or felinization) can be employed. This strategy can be based on identifying the most appropriate canine or feline germline antibody sequence for CDR grafting. Following extensive analysis of all available canine germline sequences for both the heavy and light chain, germline candidates can be selected based on their homology to the mouse mAbs, and the CDRs from the mouse progenitor mAbs can be used to replace native canine or feline CDRs. The objective is to retain high affinity and cell-based activity using fully canine or feline frameworks to minimize the potential of immunogenicity in vivo. Caninized or felinized mAbs are expressed and characterized for their ability to bind canine or feline PD-1 via Western blotting.

Caninized or felinized antibodies include antibodies having variable and constant regions derived from (or having the same amino acid sequence as those derived from) canine or feline germline immunoglobulin sequences. In some cases, caninized or felinized antibodies may include amino acid residues not encoded by canine or feline germline immunoglobulin sequences (e.g., mutations introduced by random or site-specific mutagenesis in vitro or by somatic mutation in vivo), for example in the CDRs.

A caninized or felinized antibody, typically has a canine or feline framework (FR) grafted with CDRs of an antibody derived from another species (e.g., mouse). Thus, a caninized or felinized antibody has one or more amino acid sequence introduced into it from a source other than a canine or a feline mammal. These amino acid residues are often referred to as "import" residues, which are typically taken from an "import" variable domain. Caninization or felinization can be essentially performed by e.g., substituting rodent CDRs or CDR sequences for the corresponding sequences of a canine or feline antibody. These methods are described in e.g., Singer, et al. "Generation of a canine anti-EGFR (ErbB-1) antibody for passive immunotherapy in dog cancer patients." Molecular cancer therapeutics (2014); Maekawa, et al. "A canine chimeric monoclonal antibody targeting PD-L1 and its clinical efficacy in canine oral malignant melanoma or undifferentiated sarcoma." Scientific reports 7.1 (2017): 8951; US20170158756A1; each of which is incorporated by reference herein in its entirety. Accordingly, "caninized" antibodies are chimeric antibodies wherein substantially less than an intact canine V domain has been substituted by the corresponding sequence from a non-canine species, and "felinized" antibodies are chimeric antibodies wherein substantially less than an intact feline V domain has been substituted by the corresponding sequence from a non-feline species. In practice, these antibodies are typically mouse antibodies in which some CDR residues and some FR residues are substituted by residues from analogous sites in canine or feline antibodies.

Framework residues are those residues of antibody variable regions other than hypervariable or CDR residues. Framework residues may be derived from a naturally occurring canine or feline antibody, such as a canine or feline framework that is substantially similar to a framework region of the antibody described herein. Artificial framework sequences that represent a consensus among individual sequences may also be used. When selecting a framework region for caninization or felinization, sequences that are widely represented in canines or felines may be preferred over less populous sequences. Additional mutations of the framework acceptor sequences may be made to restore murine residues believed to be involved in antigen contacts and/or residues involved in the structural integrity of the antigen-binding site, or to improve antibody expression. When the residues of the framework regions in the VH and VL are derived, at least in part, from canine or feline antibody sequences, variable regions are also described as caninized or felinized (e.g., a caninized or felinized light or heavy chain variable region).

Grafting of CDRs is performed by replacing one or more CDRs of an acceptor antibody (e.g., a caninized antibody or other antibody comprising desired framework residues) with CDRs of a donor antibody (e.g., a non-canine antibody). Acceptor antibodies can be selected based on similarity of framework residues between a candidate acceptor antibody and a donor antibody. By using the same methods, CDRs can be grafted to an antibody of *Ailuropoda melanoleuca* (giant panda).

The sequence for the constant regions for canine and feline IgG are known in the art. SEQ ID NO: 63 shows the amino acid sequence for the canine immunoglobulin gamma heavy chain A (IgG1) constant region (GenBank accession no. AAL35301.1). SEQ ID NO: 64 shows the amino acid sequence for the canine immunoglobulin gamma heavy chain B (IgG2) constant region (GenBank accession no. AAL35302.1). SEQ ID NO: 68 shows the amino acid sequence for the canine immunoglobulin gamma heavy chain C (IgG3) constant region (GenBank accession no. AAL35303.1). SEQ ID NO: 69 shows the amino acid sequence for the canine immunoglobulin gamma heavy chain D (IgG4) constant region (GenBank accession no. AAL35304.1).

SEQ ID NO: 65 shows the amino acid sequence for the canine kappa chain (GenBank accession no. XP 532962.3). SEQ ID NO: 70 and 71 show the amino acid sequence for the canine IgG light chain constant regions.

SEQ ID NO: 66 is the amino acid sequence for the feline heavy chain constant region (GenBank: BAA32229.1). SEQ ID NO: 67 is the amino acid sequence for the feline kappa chain constant region (GenBank: AAF09245.1).

It is further important that antibodies be caninized or felinized with retention of high specificity and affinity for the antigen and other favorable biological properties. To achieve this goal, caninized or felinized antibodies can be prepared by a process of analysis of the parental sequences and various conceptual caninized or felinized products using three-dimensional models of the parental and caninized or felinized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

In some cases, back mutation of selected residues in the variable region is used to enhance presentation of the CDRs. Designing antibodies that minimize immunogenic reaction in a subject to non-native sequences in the antibody, while at the same time preserving antigen binding regions of the antibody sufficiently to maintain efficacy, has proven challenging. As used herein, the term "back mutation" refers to a process in which some or all of the somatically mutated amino acids of a canine or feline antibody are replaced with the corresponding germline residues from a homologous germline antibody sequence. The heavy and light chain sequences of the canine or feline antibody are aligned separately with the germline sequences to identify the sequences with the highest homology. Differences in the canine or feline antibody are returned to the germline sequence by mutating defined nucleotide positions encoding such different amino acid. The role of each amino acid thus identified as candidate for back mutation should be investigated for a direct or indirect role in antigen binding and any amino acid found after mutation to affect any desirable characteristic of the antibody should not be included in the final antibody; as an example, activity enhancing amino acids identified by the selective mutagenesis approach will not be subject to back mutation. To minimize the number of amino acid positions subject to back mutation those amino acid positions found to be different from the closest germline sequence but identical to the corresponding amino acid in a second germline sequence can remain, provided that the second germline sequence is identical and colinear to the sequence of the antibody. Back mutation of selected target framework residues to the corresponding donor residues might be required to restore and or improved affinity.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some embodiments, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine, 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces*, and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH may be used. For reviews, see Ausubel et al (1989) Current Protocols in Molecular Biology, John Wiley & Sons, New York, N.Y., and Grant et al, *Methods Enzymol*, 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

Methods of Treatment

The antibodies or antibody or antigen-binding fragments thereof of the present disclosure can be used for various therapeutic purposes. In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer.

In some embodiments, the compositions and methods disclosed herein can be used for treatment of patients at risk for a cancer. Patients with cancer can be identified with various methods known in the art.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody or an antigen binding fragment is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody or antigen binding fragment may vary, depending on, inter alia, patient history as well as other factors such as the type (and/or dosage) of antibody used.

Effective amounts and schedules for administering the antibodies, antibody-encoding polynucleotides, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, and/or compositions disclosed herein, the route of administration, the particular type of antibodies, antibody-encoding polynucleotides, antigen binding fragments, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, or pharmaceutical composition (e.g., any of the antibodies, antigen-binding fragments, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody or antigen-binding fragment and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

Methods of modifying and using the anti-PD-1 antibodies are described, e.g., in US20170247454, US 20170081409 A1, US 20170044259 A1, and US 20160159905 A1; each of which is incorporated herein by reference in its entirety.

Pharmaceutical Compositions and Routes of Administration

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies or antigen-binding fragments described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a dog, a cat, or a panda). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a subject identified as having cancer), or a subject identified as being at risk of developing the disease (e.g., a subject who has previously developed cancer but now has been cured), decreases the severity, frequency, and/or duration of one or more symptoms of a disease in a subject (e.g., a dog, a cat, or a panda). The effectiveness and dosing of any of the antibodies or antigen-binding fragments described herein can be determined by a health care professional or veterinary professional using methods known in the art, as well as by the observation of one or more symptoms of disease in a subject (e.g., a dog, a cat, or a panda). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments described herein per kilogram of the subject's weight (e.g., about 1 μg/kg to about 500 mg/kg; about 100 μg/kg to about 500 mg/kg; about 100 μg/kg to about 50 mg/kg; about 10 μg/kg to about 5 mg/kg; about 10 μg/kg to about 0.5 mg/kg; or about 1 μg/kg to about 50 μg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration. The disclosure also provides methods of manufacturing the antibodies or antigen binding fragments thereof for various uses as described herein.

EXAMPLES

The invention is further described in the following examples, which do not limit the scope of the invention described in the claims.

Example 1. Generating Mouse Anti-dPD-1 Antibodies

Figure 1B:
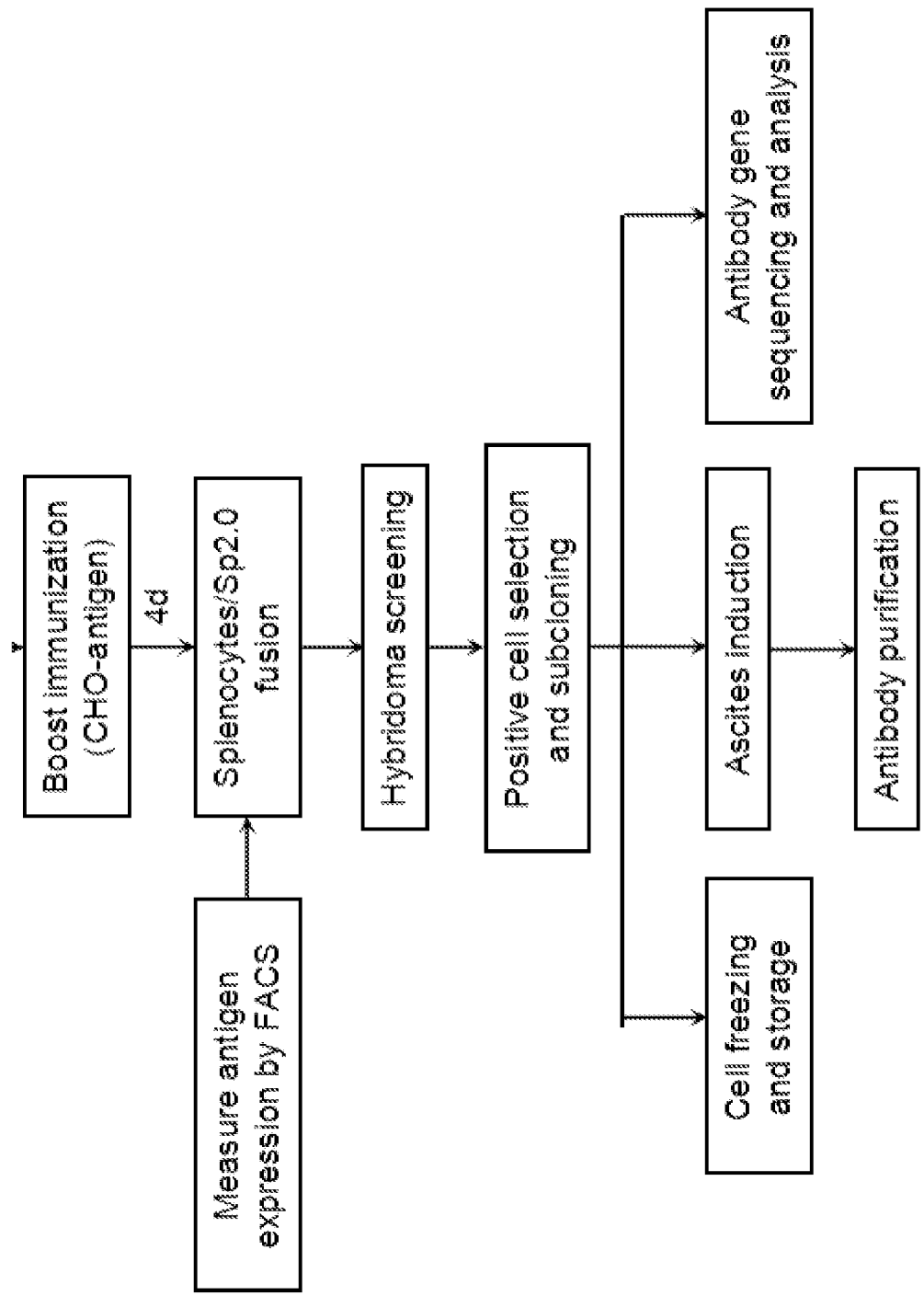
FIG. 1B is a flow chart showing the second part of an exemplary protocol of making anti-dPD-1 antibodies.
Figure 2:
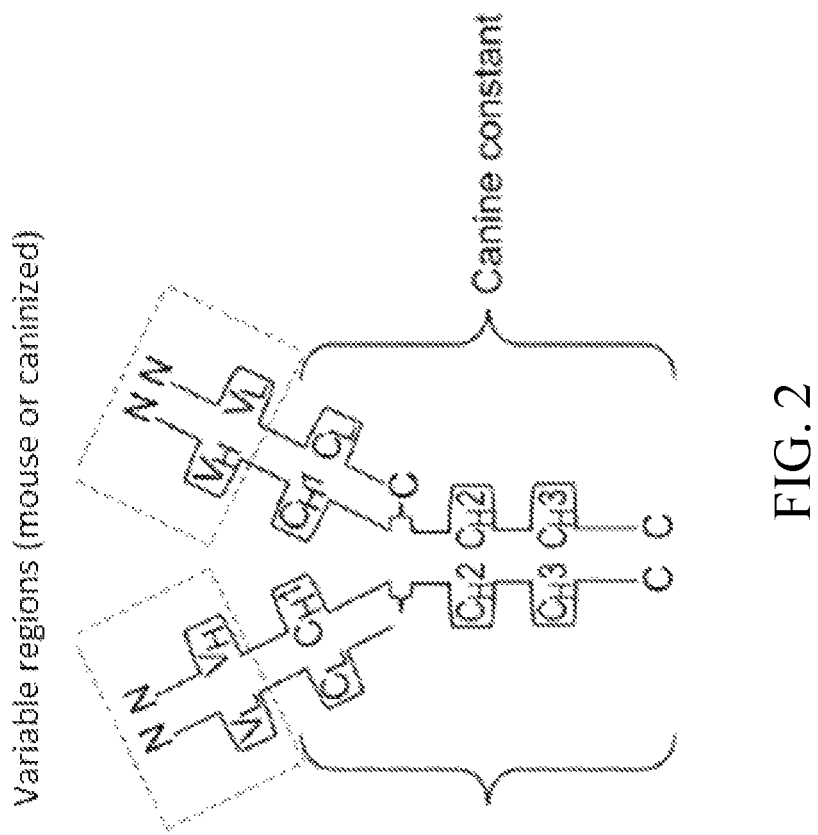
FIG. 2 is a schematic representation of the general structure of a mouse:canine chimeric IgG with mouse variable regions and canine constant regions, or a caninized IgG with caninized variable regions and canine constant regions.

To generate mouse antibodies against canine PD-1 (dPD-1; SEQ ID NO: 41), 6-8 weeks old female BALB/c mice were immunized with canine PD-1. Anti-dPD-1 antibodies were collected by the methods as described below and shown in FIG. 1A and FIG. 1B.

Immunization of Mice 6-8 weeks old female BALB/c mice were immunized with His-tagged canine PD-1 proteins at 20 μg/mouse at a concentration of 100 μg/ml. The His-tagged canine PD-1 proteins were emulsified with adjuvant and injected at four positions on the back of the mice. For the first subcutaneous (s.c.) injection, the diluted antigen was emulsified with Complete Freund's Adjuvant (CFA) in equal volume. In the following subcutaneous injections, the protein was emulsified with Incomplete Freund's Adjuvant (IFA) in equal volume. Three days after the third injection or the booster immunization, blood (serum) was collected and analyzed for antibody titer using ELISA.

In another experiment, 6-8 weeks old female BALB/c mice were immunized by injecting the expression plasmid encoding canine PD-1 into the mice. The plasmids encoding the antigen were injected into the tibialis anterior muscle (intramuscular injection; i.m. injection) of the mice by using gene guns at the concentration of 1000 μg/ul at 60 μg per mouse. At least four injections were performed with at least 14 days between two injections. Blood (serum) was collected seven days after the last immunization and the serum was tested for antibody titer by ELISA.

Procedures to enhance immunization were also performed at least fourteen days after the previous immunization (either by injecting the plasmid or by injecting the proteins). CHO cells that express PD-1 antigen on the surface were intravenously injected into the mice through tail veins. Spleen was then collected four days after the injection.

Fusion of SP2/0 Cells and Spleen Cells

Spleen tissues were grinded. Spleen cells were first selected by CD3ε Microbeads and Anti-Mouse IgM Microbeads, and then fused with SP2/0 cells. The cells were then plated in 96-well plates with hypoxanthine-aminopterin-thymidine (HAT) medium.

Primary Screening of Hybridoma

Primary screening of the hybridoma supernatant in the 96-well plates was performed using Fluorescence-Activated Cell Sorting (FACS) pursuant to standard procedures. Chinese hamster ovary (CHO) cells were added to 96-well plates ($2 \times 10^4$ cells per well) before the screening. 50 μl of supernatant and human Fc-tagged canine PD-L1 proteins was used. The antibodies that were used in experiments were 1) Fluorescein (PE)—conjugated AffiniPure F(ab)2 Fragment Goat Anti-Mouse IgG, Fc γ Fragment Specific, and 2) Fluorescein (FITC)—conjugated AffiniPure F(ab)2 Fragment Goat Anti-Human IgG, Fc γ Fragment Specific.

Sub-Cloning

Sub-cloning was performed using ClonePix2. In short, the positive wells identified during the primary screening were transferred to semisolid medium, and IgG positive clones were identified and tested. FITC anti-mouse IgG Fc antibody was used.

Ascites Fluid Antibodies $1 \times 10^6$ positive hybridoma cells were injected intraperitoneally to B-NDG® mice (Beijing Biocytogen, Beijing, China). Monoclonal antibodies were produced by growing hybridoma cells within the peritoneal cavity of the mouse. The hybridoma cells multiplied and produced ascites fluid in the abdomens of the mice. The fluid contained a high concentration of antibody which can be harvested for later use.

Purification of Antibodies

Antibodies in ascites fluid were purified using GE AKTA protein chromatography (GE Healthcare, Chicago, Illinois, United States). 13-1B9 ("1B9"), 12-4A7 ("4A7"), and 12-1D8 ("1D8") were among the mouse antibodies produced by the methods described above.

The VH, VL and CDR regions of the antibodies were determined. The heavy chain CDR1, CDR2, CDR3, and light chain CDR1, CDR2, and CDR3 amino acid sequences of 1B9 are shown in SEQ ID NOs: 1-6 (Kabat numbering) or SEQ ID NOs: 19-24 (Chothia numbering).

The heavy chain CDR1, CDR2, CDR3, and light chain CDR1, CDR2, and CDR3 amino acid sequences of 4A7 are shown in SEQ ID NOs: 7-12 (Kabat numbering) or SEQ ID NOs: 25-30 (Chothia numbering).

The heavy chain CDR1, CDR2, CDR3, and light chain CDR1, CDR2, and CDR3 amino acid sequences of 1D8 are shown in SEQ ID NOs: 13-18 (Kabat numbering) or SEQ ID NOs: 31-36 (Chothia numbering).

Chimeric Antibodies

Based on the sequences of heavy chain and light chain variable regions of 1B9, 4A7, and 1D8, chimeric anti-dPD-1 antibodies including 1B9-mHvKv-dIgG4, 4A7-mHvKv-IgG4, and 1D8-mHvKv-IgG4 were generated. These chimeric antibodies have the heavy chain variable domain and the light chain variable domain from the corresponding mouse anti-dPD-1 antibodies, with the constant domains from canine IgG4 antibody (including, e.g., the CL, CH1, CH2, and CH3 domains). The sequences for constant domains for canine IgG4 heavy chain is shown in SEQ ID NO: 69. The sequences for constant domain of canine IgG light chain is shown in SEQ ID NO: 70.

Example 2. Caninization of the Mice Antibodies

The starting point for caninization was the mouse antibodies (e.g., 1B9 and 1D8). The amino acid sequences for the heavy chain variable region and the light chain variable region of these mouse antibodies were determined.

Three caninized heavy chain variable region variants (SEQ ID NOs: 49-51) and three caninized light chain variable region variants (SEQ ID NOs: 52-54) for 1B9 were constructed, containing different modifications or substitutions.

Three caninized heavy chain variable region variants (SEQ ID NOs: 42-44) and four caninized light chain variable region variants (SEQ ID NOs: 45-48) for 1D8 were constructed, containing different modifications or substitutions.

These caninized heavy chain variable region variants can be combined with any of the light chain variable region variants based on the same mouse antibody. For example, 1B9-H1 (SEQ ID NO: 49) can be combined with any caninized light chain variable region variant based on the same mouse antibody 1B9 (e.g., 1B9-K3 (SEQ ID NO: 54)), and the antibody is labeled accordingly (e.g., 1B9-H1K3).

The caninized antibodies can have canine IgG antibody constant domains (including, e.g., the CL, CH1, CH2, and CH3 domains). For example, 1B9-H1K1-IgG4 is based on the mouse antibody 1B9 and has the caninized heavy chain variable domain H1 (SEQ ID NO: 49) and caninized light chain variable domain K1 (SEQ ID NO: 52).

The name and the sequences of the chimeric anti-PD-1 antibodies and the caninized anti-PD-1 antibodies are summarized in the table below.

TABLE 1

| Type | Antibody name | VH SEQ ID NO: | VL SEQ ID NO: | Constant regions |
|---|---|---|---|---|
| Chimeric antibody based on 1B9 | 1B9-mHvKv-IgG4 | 59 | 60 | Canine IgG4 |
| Caninized antibodies based on 1B9 | 1B9-H1K1-IgG4 | 49 | 52 | Canine IgG4 |
| | 1B9-H1K2-IgG4 | 49 | 53 | Canine IgG4 |
| | 1B9-H1K3-IgG4 | 49 | 54 | Canine IgG4 |
| | 1B9-H2K1-IgG4 | 50 | 52 | Canine IgG4 |
| | 1B9-H2K2-IgG4 | 50 | 53 | Canine IgG4 |
| | 1B9-H2K3-IgG4 | 50 | 54 | Canine IgG4 |
| | 1B9-H3K1-IgG4 | 51 | 52 | Canine IgG4 |
| | 1B9-H3K2-IgG4 | 51 | 53 | Canine IgG4 |

TABLE 1-continued

| Type | Antibody name | VH SEQ ID NO: | VL SEQ ID NO: | Constant regions |
|---|---|---|---|---|
| | 1B9-H3K3-IgG4 | 51 | 54 | Canine IgG4 |
| Chimeric antibody based on 4A7 | 4A7-mHvKv-IgG4 | 55 | 56 | Canine IgG4 |
| Chimeric antibody based on 1D8 | 1D8-mHvKv-IgG4 | 57 | 58 | Canine IgG4 |
| Caninized antibodies based on 1D8 | 1D8-H1K1-IgG4 | 42 | 45 | Canine IgG4 |
| | 1D8-H1K2-IgG4 | 42 | 46 | Canine IgG4 |
| | 1D8-H1K3-IgG4 | 42 | 47 | Canine IgG4 |
| | 1D8-H1K4-IgG4 | 42 | 48 | Canine IgG4 |
| | 1D8-H2K1-IgG4 | 43 | 45 | Canine IgG4 |
| | 1D8-H2K2-IgG4 | 43 | 46 | Canine IgG4 |
| | 1D8-H2K3-IgG4 | 43 | 47 | Canine IgG4 |
| | 1D8-H2K4-IgG4 | 43 | 48 | Canine IgG4 |
| | 1D8-H3K1-IgG4 | 44 | 45 | Canine IgG4 |
| | 1D8-H3K2-IgG4 | 44 | 46 | Canine IgG4 |
| | 1D8-H3K3-IgG4 | 44 | 47 | Canine IgG4 |
| | 1D8-H3K4-IgG4 | 44 | 48 | Canine IgG4 |

Example 3. In Vitro Testing of the Mouse Anti-dPD-1 Antibodies: Blocking the Binding of Canine PD-1 (dPD-1) and Canine PD-L1 (dPD-L1)

Blocking assays were performed to determine whether the anti-dPD-1 antibodies can block the binding between dPD-1 and its ligand dPD-L1.

200 μL of canine PD-L1 Protein (Fc Tag) (250 μg/mL) (Sino Biological, Beijing; Cat #70110-D02H) was mixed with 1.94 μL of EZ-Link® Sulfo-NHS-LC-Biotin (10 mM). The mixture was then desalted by PD MiniTrap G-10 column and was stored at −20° C. for future use.

The anti-dPD-1 chimeric antibodies were collected from mouse ascites fluid and purified by chromatography. 25 μl CHO cells transiently transfected with canine PD-1 were added to each well in a plate. The purified antibodies were titrated to the desired final concentrations, and were added to each well at 25 μl per well at 4° C. and incubated for 30 minutes.

Bitoin labeled dPD-L1 was added to each well (with a final concentration of 5 μg/ml in each well). The cells, Bitoin labeled dPD-L1 and the antibodies were incubated at 4° C. for 30 minutes.

After being washed with phosphate-buffered saline (PBS) twice (1200 rpm, 5 minutes), 50 μl of PE-labeled Streptavidin (Streptavidin-PE) at 1:100 dilution was added into each well, and incubated for 30 minutes at 4° C., followed by PBS wash (1200 rpm, 5 minutes). 20 μl of PBS was added. The signals for PE was detected by flow cytometry (Intellicyt).

Figure 3:
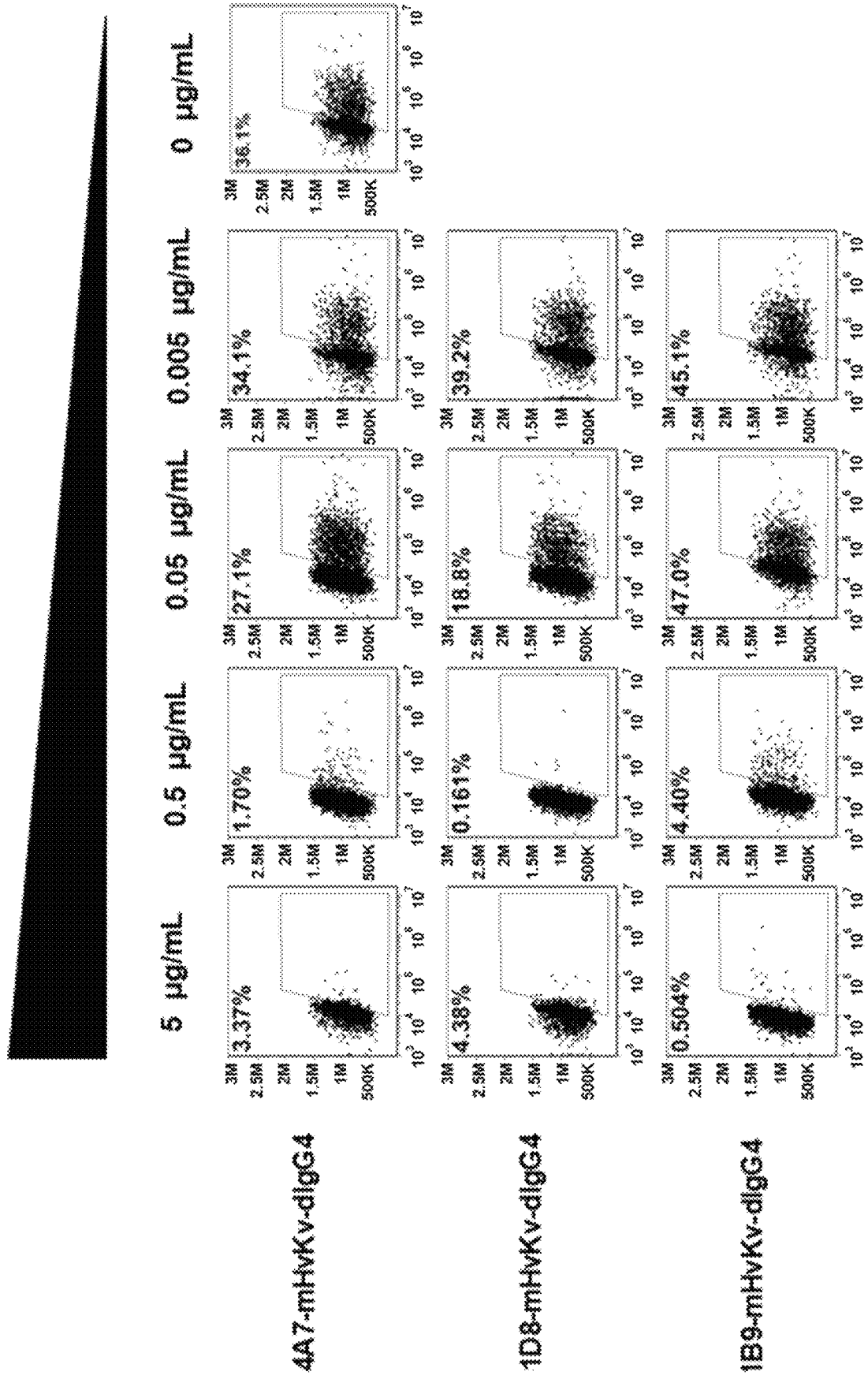
FIG. 3 is a set of flow cytometry graphs showing that the anti-dPD-1 antibodies block the binding between canine PD-1 (dPD-1) and canine PD-L1 (dPD-L1).

As shown in FIG. 3, when the concentration of the chimeric anti-dPD-1 antibodies 4A7-mHvKv-dlgG4, 1D8-mHvKv-dlgG4, and 1B9-mHvKv-dlgG4 decreased, the signal for PE increased (x axis), suggesting that the binding between canine PD-1 and canine PD-L1 was blocked by the three anti-dPD-1 antibodies.

Example 4. Cross-Reactivity of Anti-dPD-1 Antibodies Against Human, Mouse, and Dog-Mouse Chimeric PD-1, Panda PD-1 and Feline PD-1

In each experiment, the CHO cells were transfected with human PD-1 (hPD-1, SEQ ID NO: 37), mouse PD-1 (mPD- 1, SEQ ID NO: 38), chimeric (mouse and dog) PD-1 (chidPD-1, SEQ ID NO: 40), or panda PD-1 (pPD-1, SEQ ID NO: 61)

25 µl CHO cells were added to each well. 25 µl purified anti-dPD-1 chimeric antibodies (10 µg/ml) (4A7-mHvKv-dIgG4, 1D8-mHvKv-dIgG4, or 1B9-mHvKv-dIgG4) were added to each well and were incubated at 4° C. for 30 minutes.

After being washed with PBS (1200 rmp, 5 min) twice, FITC labeled anti-dog IgG Fc antibody (anti-dIgG Fc-FITC) was added into each well 1:100 dilution, followed by incubating at 4° C. for 30 minutes, and then PBS wash (1200 rmp, 5 min). The signals for FITC were determined by flow cytometry.

Figure 4:
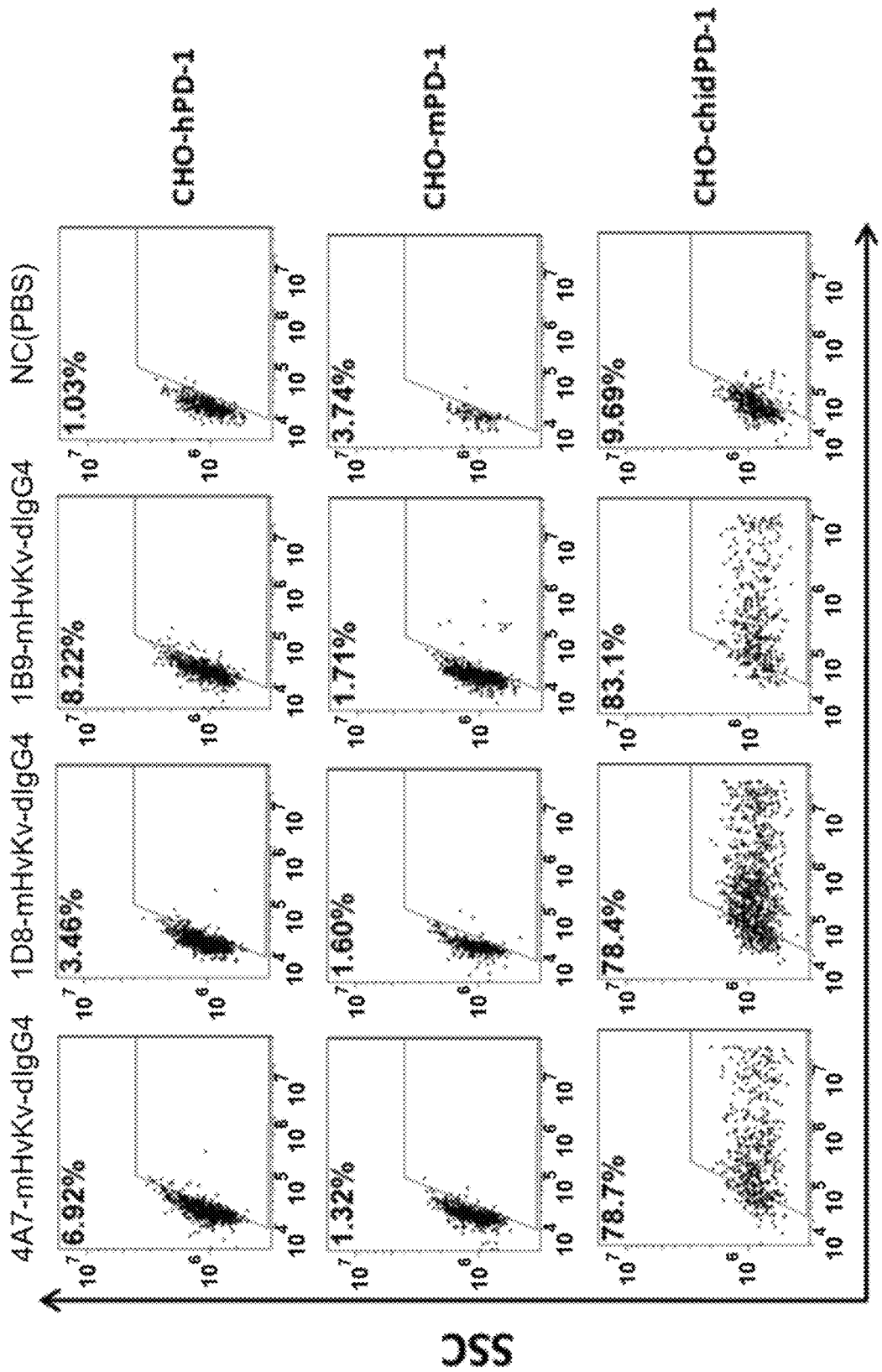
FIG. 4 is a set of graphs showing flow cytometry results of analyzing the anti-dPD-1 antibodies' cross-reactivity with human PD-1 (hPD-1), mouse PD-1 (mPD-1), and mouse-dog chimeric PD-1 (chidPD-1). NC stands for negative control.
Figure 5:
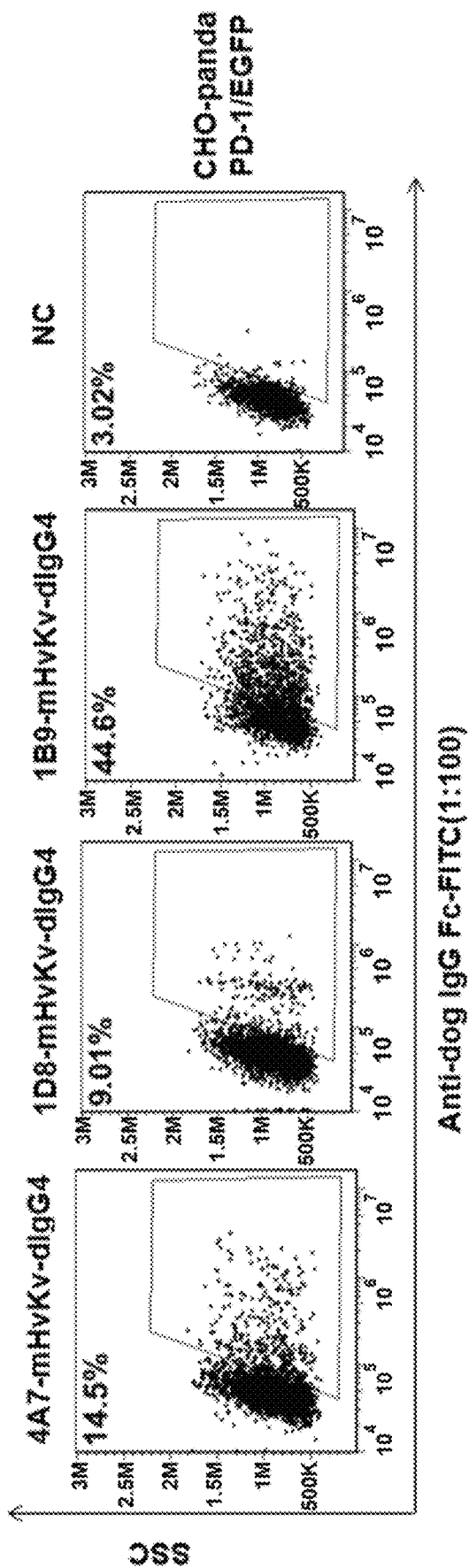
FIG. 5 is a set of graphs showing flow cytometry results of analyzing the anti-dPD-1 antibodies' cross-reactivity with panda PD-1 (pPD-1). NC stands for negative control.

As shown in FIG. 4, 4A7-mHvKv-dIgG4, 1D8-mHvKv-dIgG4, and 1B9-mHvKv-dIgG4 did not cross react with human PD-1 or mouse PD-1, but had strong binding activity with chidPD-1. With respect to panda PD-1, 4A7-mHvKv-dIgG4 and 1D8-mHvKv-dIgG4 had some cross-reactivity with pPD-1, and 1B9-mHvKv-dIgG4 had strong binding activity with pPD-1 (FIG. 5). In FIG. 4 and FIG. 5, NC stands for negative control.

Figure 6:
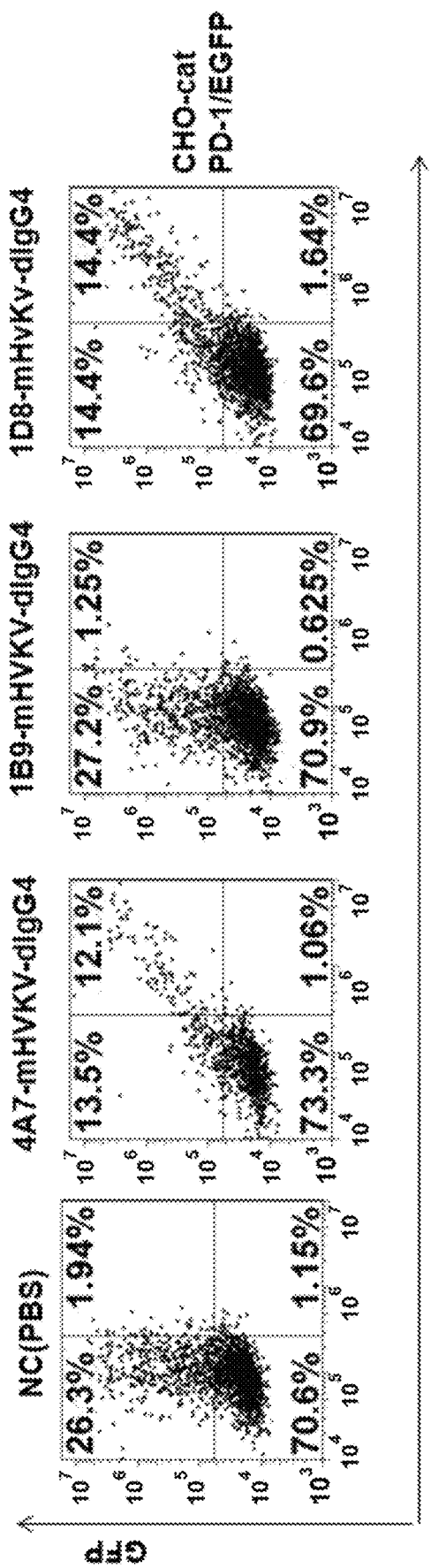
FIG. 6 is a set of graphs showing flow cytometry results of analyzing the anti-dPD-1 antibodies' cross-reactivity with feline PD-1 (cPD-1). NC stands for negative control.

The CHO cells were transfected with an expression vector that expresses feline PD-1 (cPD-1, SEQ ID NO: 62) and EGFP. 25 µl purified anti-dPD-1 chimeric antibodies (10 µg/ml) were added to each well and were incubated at 4° C. for 30 minutes. After being washed with PBS (1200 rmp, 5 min) twice, Alexa Fluor 647 labeled anti-dog IgG Fc antibody (anti-dIgG Fc-647) was added into each well 1:500 dilution, followed by incubating at 4° C. for 30 minutes, and then PBS wash (1200 rmp, 5 min). The signals for GFP and FITC were determined by flow cytometry. The results show that 1B9-mHvKv-dIgG4 did not bind to feline PD-1. However, 4A7-mHvKv-dIgG4 and 1D8-mHvKv-dIgG4 had some binding activity with feline PD-1 (FIG. 6).

Example 5. EC50 for Binding Activity Against Panda PD-1, Canine PD-1, and Feline PD-1

In each experiment, the CHO cells were transfected with panda PD-1, canine PD-1, or feline PD-1.

25 µl CHO cells were added to each well. 25 µl purified anti-dPD-1 chimeric antibodies with different concentrations were added to each well and were incubated at 4° C. for 30 minutes.

After being washed with PBS (1200 rmp, 5 min) twice, 50 µl of Alexa Fluor 647 labeled anti-dog IgG Fc antibody (anti-dIgG Fc-647) was added into each well at 1:1000 dilution, followed by incubating at 4° C. for 30 minutes, and then PBS wash (1200 rmp, 5 min). 30 µl of PBS was then added. The signals for Alexa Fluor 647 were determined by flow cytometry. And the curve for the mean of fluorescence intensity (MFI) was used to determine EC50.

Figure 7:
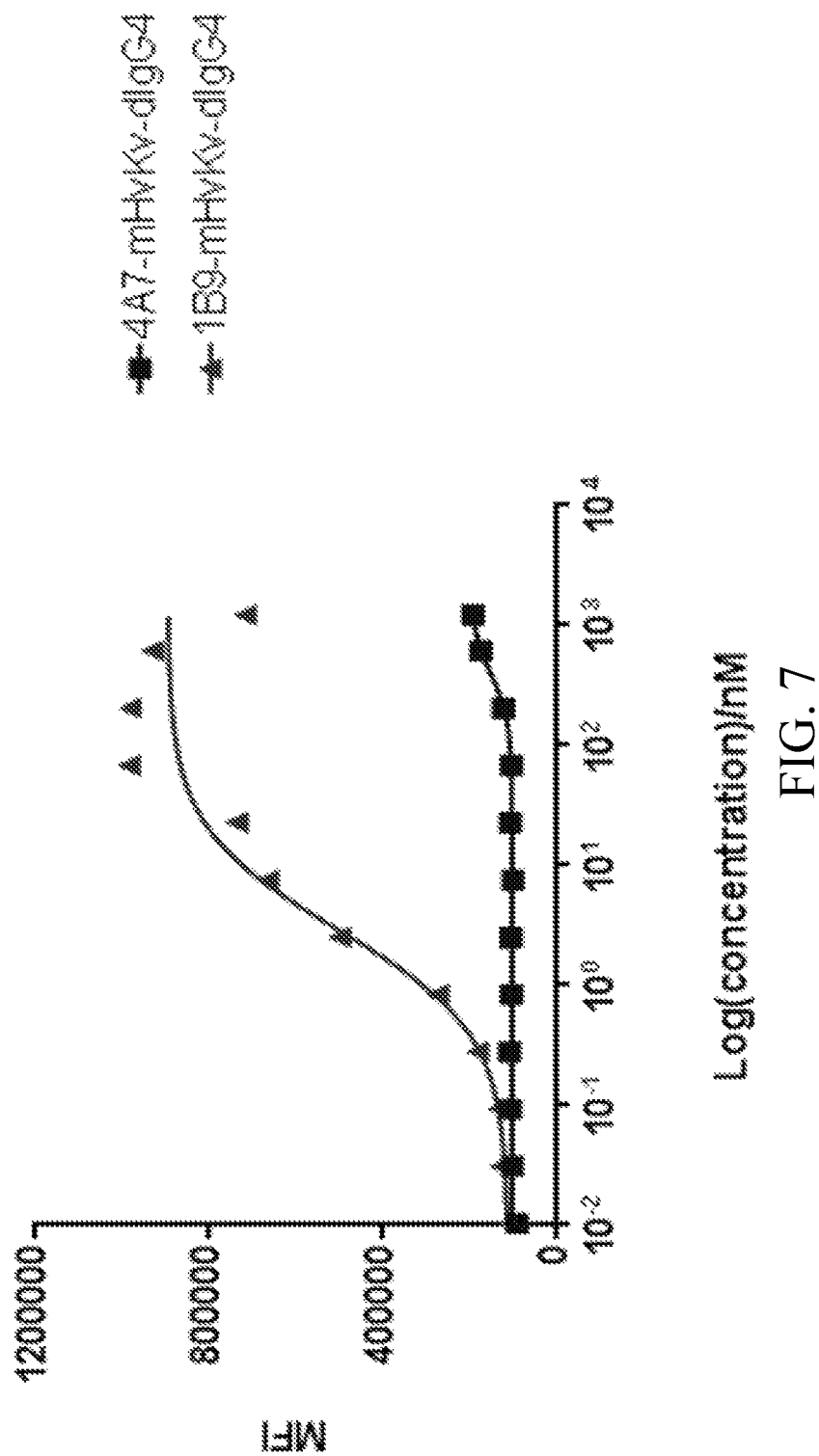
FIG. 7 shows the mean of fluorescence intensity indicating the binding activity to panda PD-1 at different concentrations of 4A7-mHvKv-dIgG4 and 1B9-mHvKv-dIgG4.

In FIG. 7, the CHO cells were transfected with panda PD-1. FIG. 7 shows the MFI at different concentrations of 4A7-mHvKv-dIgG4 and 1B9-mHvKv-dIgG4. EC50 were determined. The result shows that 1B9-mHvKv-dIgG4 has strong binding activity with panda PD-1.

TABLE 2

| Antibody | EC50 (nM) for panda PD-1 |
|---|---|
| 4A7-mHvKv-dIgG4 | 385.5 |
| 1B9-mHvKv-dIgG4 | 2.866 |

Figure 8:
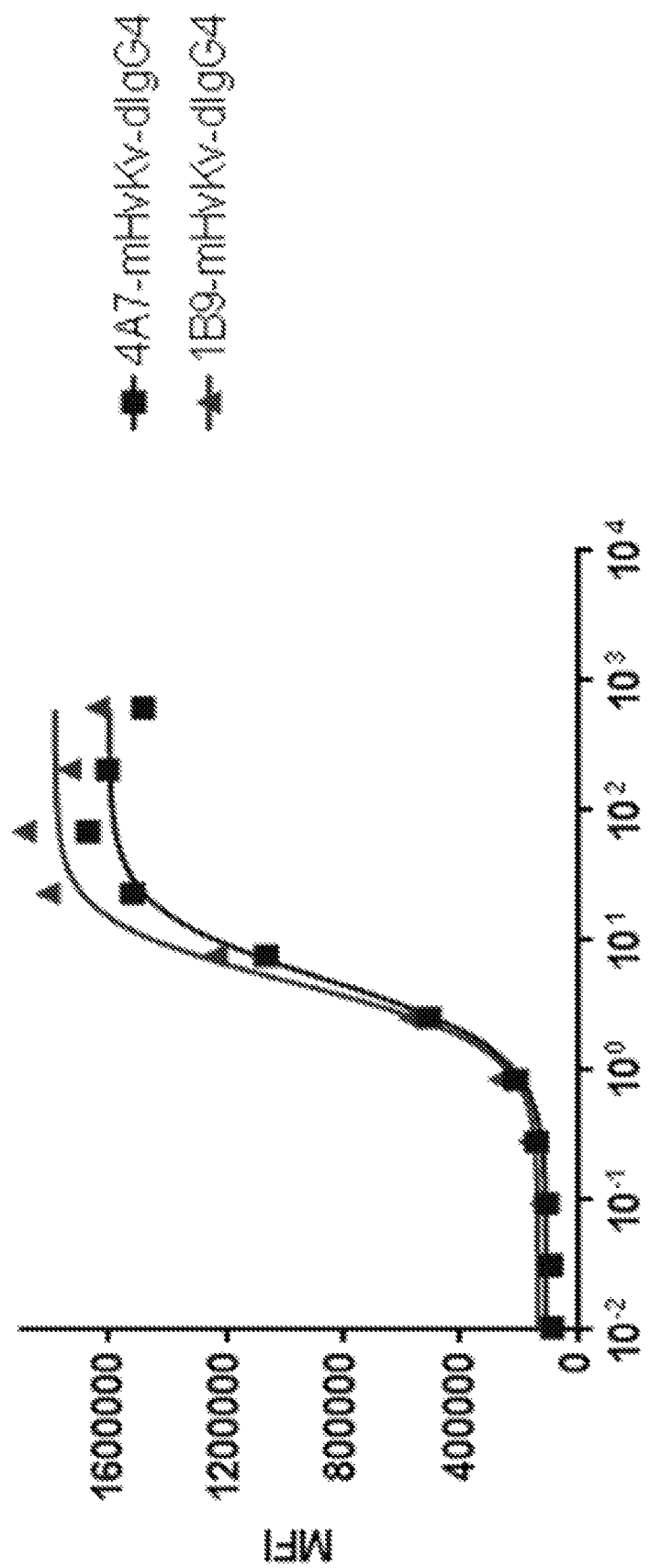
FIG. 8 shows the mean of fluorescence intensity indicating the binding activity to canine PD-1 at different concentrations of 4A7-mHvKv-dIgG4 and 1B9-mHvKv-dIgG4.

In FIG. 8, the CHO cells were transfected with canine PD-1. FIG. 8 shows the MFI at different concentrations of 4A7-mHvKv-dIgG4 and 1B9-mHvKv-dIgG4. EC50 were determined. The result shows that both antibodies have strong binding activity with canine PD-1.

TABLE 3

| Antibody | EC50 (nM) for canine PD-1 |
|---|---|
| 4A7-mHvKv-dIgG4 | 4.81 |
| 1B9-mHvKv-dIgG4 | 4.52 |

Figure 9:
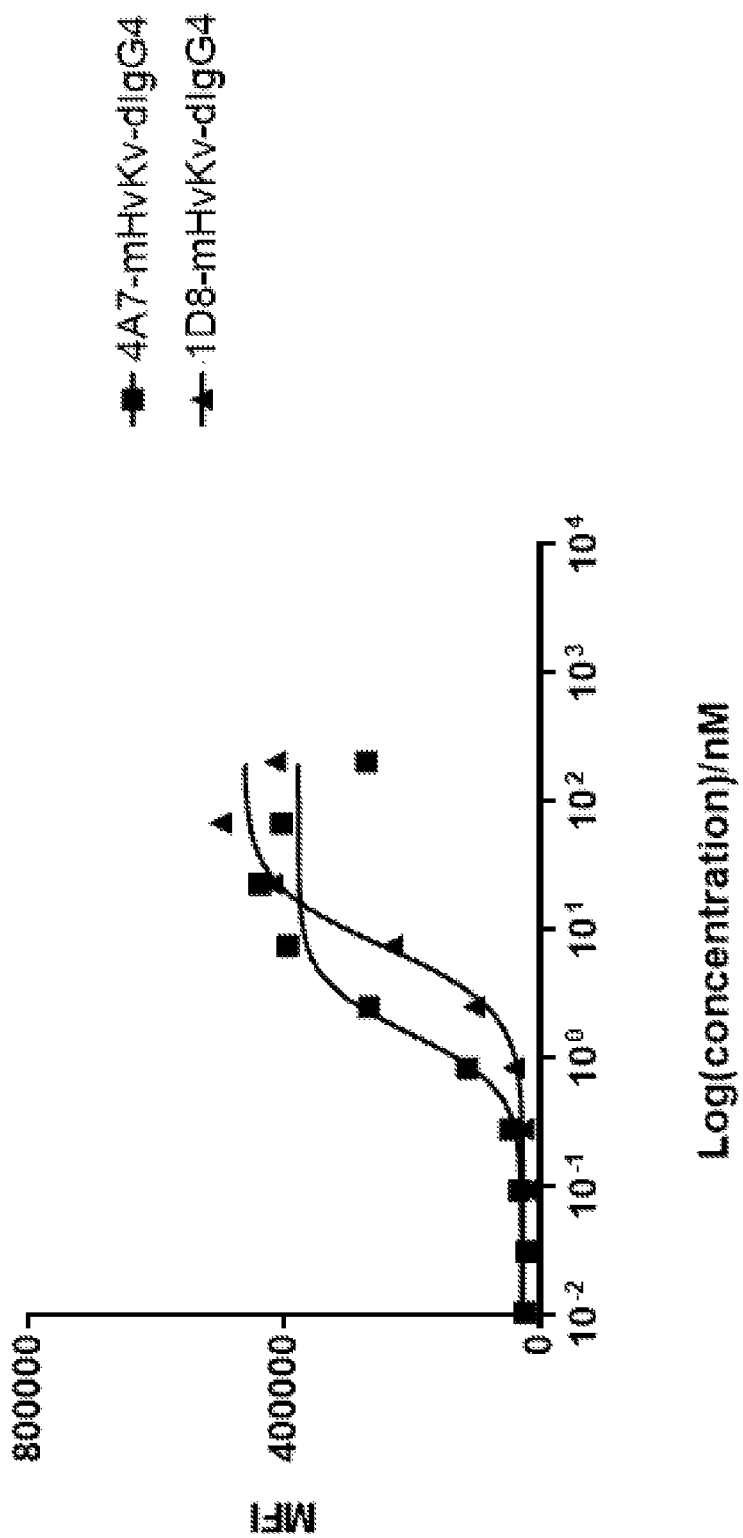
FIG. 9 shows the mean of fluorescence intensity indicating the binding activity to feline PD-1 at different concentrations of 4A7-mHvKv-dIgG4 and 1D8-mHvKv-dIgG4.
Figure 10:
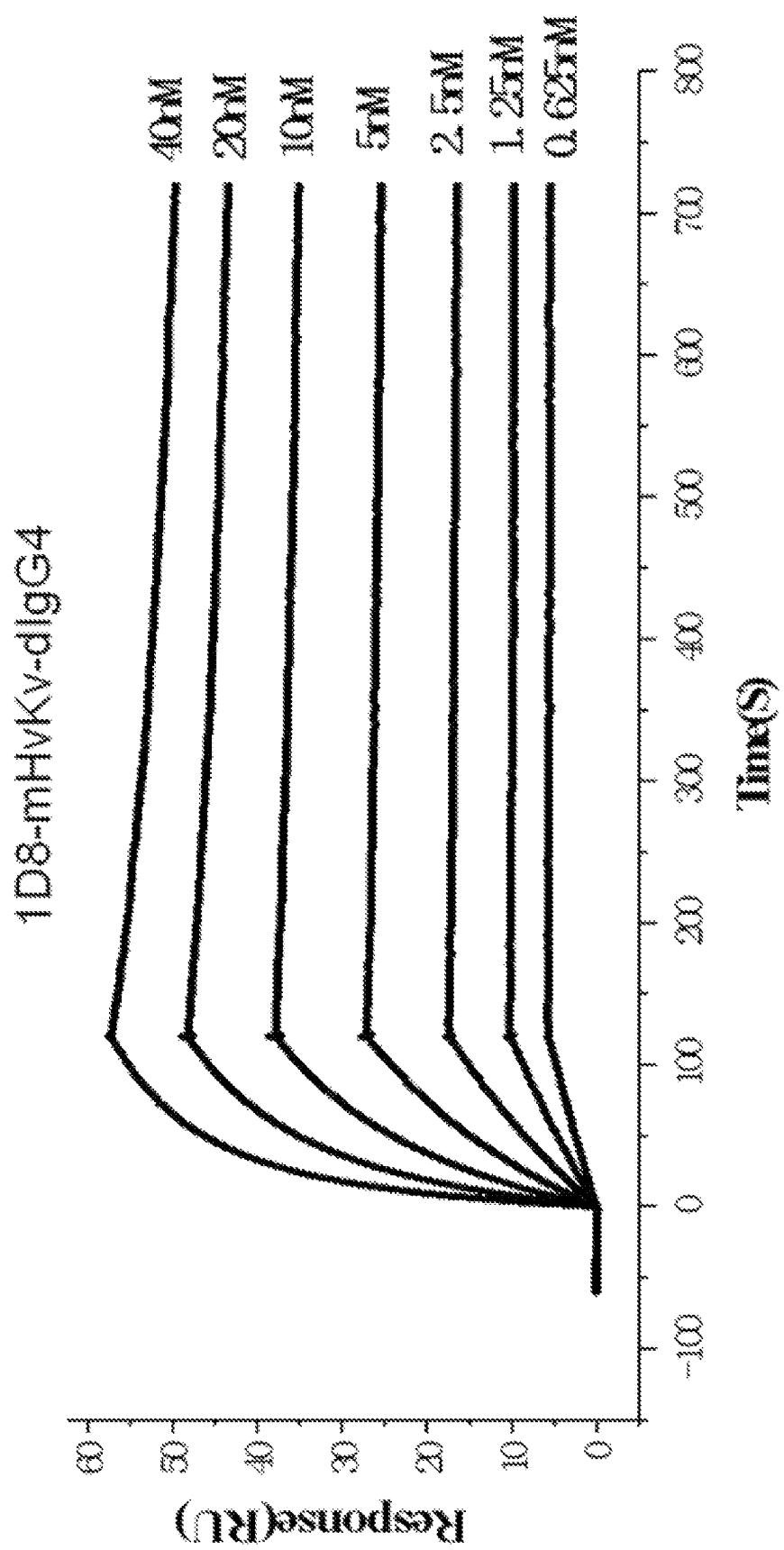
FIG. 10 is a graph showing the results of surface plasma resonance (SPR) using the chimeric anti-dPD-1 antibody 1D8-mHvKv-dIgG4 and canine PD-1.

In FIG. 9, the CHO cells were transfected with an expression vector that expresses feline PD-1 and EGFP. 25 µl purified anti-dPD-1 chimeric antibodies with different concentrations were added to each well. After being washed with PBS (1200 rmp, 5 min) twice, 50 µl of Alexa Fluor 647 labeled anti-dog IgG Fc antibody (anti-dIgG Fc-647) was added into each well at 1:500 dilution, followed by incubating at 4° C. for 30 minutes, and then PBS wash (1200 rmp, 5 min). 30 µl of PBS was then added. FIG. 9 shows the MFI at different concentrations of 4A7-mHvKv-dIgG4 and 1D8-mHvKv-dIgG4. EC50 were also determined from the data. The results show that both antibodies have strong binding activity with feline PD-1, and the EC50 for 4A7-mHvKv-dIgG4 is better than 1D8-mHvKv-dIgG4.

TABLE 4

| Antibody | EC50 (nM) for feline PD-1 |
|---|---|
| 4A7-mHvKv-dIgG4 | 1.528 |
| 1D8-mHvKv-dIgG4 | 7.291 |

Example 6. Binding Affinity of Anti-dPD-1 Antibodies

The binding affinity of the anti-dPD-1 antibodies were measured using surface plasmon resonance (SPR) using Biacore (Biacore, INC, Piscataway N.J.)

Histidine-tagged canine PD-1 proteins (dPD-1-His) were diluted to the final concentration of 3.34 µg/ml and fixed to the CM5 chip with Amine Coupling Kit (GE Healthcare; Cat #BR100050) to achieve to a desired protein density (about 90 response units (RU)).

Anti-dPD-1 antibodies at the concentration of 40, 20, 10, 5, 2.5, 1.25, or 0.625 nM were injected at 30 µL/min for 120~240 seconds. Dissociation was monitored for 600 seconds. The chip was regenerated after the last injection of each titration with Glycine (pH 1.5, 30 µL/min for 16 seconds). The result for 1D8-mHvKv-dIgG4 is shown in FIG. as an example.

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore T200 Evaluation Software 3.0. Affinities were deduced from the quotient of the kinetic rate constants (KD=koff/kon).

As a person of ordinary skill in the art would understand, the same method with appropriate adjustments for parameters (e.g., antibody concentration) was performed for each tested antibody. The results for the tested antibodies are summarized in the table below.

mice reached a volume of $150\pm50$ mm$^3$, the mice were randomly placed into different groups based on the volume of the tumor (five mice in each group).

The mice were then injected with physiological saline (PS) and anti-dPD-1 antibodies by intraperitoneal administration as indicated in the table below. The antibody was given on the second day and the fifth day of each week. Most groups had 6 administrations in total. G12 only had 2 administrations in total.

TABLE 6

| Group | No. of mice | Antibodies | Dosage (mg/kg) | Route | Frequency | Total No. of administration |
|---|---|---|---|---|---|---|
| G1 | 4 | PS (control) | — | i.p. | Day 2.5/wk | 6 |
| G2 | 4 | 1B9-H1K1-dIgG4 | 3 mg/kg | i.p. | Day 2.5/wk | 6 |
| G3 | 4 | 1B9-H1K2-dIgG4 | 3 mg/kg | i.p. | Day 2.5/wk | 6 |
| G4 | 4 | 1B9-H2K1-dIgG4 | 3 mg/kg | i.p. | Day 2.5/wk | 6 |
| G5 | 4 | 1B9-H2K2-dIgG4 | 3 mg/kg | i.p. | Day 2.5/wk | 6 |
| G6 | 4 | 1D8-H1K1-dIgG4 | 3 mg/kg | i.p. | Day 2.5/wk | 6 |
| G7 | 4 | 1D8-H1K2-dIgG4 | 3 mg/kg | i.p. | Day 2.5/wk | 6 |
| G8 | 4 | 1D8-H2K1-dIgG4 | 3 mg/kg | i.p. | Day 2.5/wk | 6 |
| G9 | 4 | 1D8-H2K2-dIgG4 | 3 mg/kg | i.p. | Day 2.5/wk | 6 |
| G10 | 4 | 1D8-mHvKv-dIgG4 | 3 mg/kg | i.p. | Day 2.5/wk | 6 |
| G11 | 4 | 1B9-mHvKv-dIgG4 | 3 mg/kg | i.p. | Day 2.5/wk | 6 |
| G12 | 4 | 4A7-mHvKv-dIgG4 | 3 mg/kg | i.p. | Day 2.5/wk | 2 |

TABLE 5

| Anti-dPD-1 antibodies | Association rate kon (1/Ms) | Dissociation rate koff (1/s) | Affinity KD(M) |
|---|---|---|---|
| 1D8-H1K1-dIgG4 | 6.75E+05 | 3.09E−03 | 4.57E−09 |
| 1D8-H1K2-dIgG4 | 5.50E+05 | 2.48E−03 | 4.50E−09 |
| 1D8-H2K1-dIgG4 | 6.50E+05 | 3.48E−03 | 5.36E−09 |
| 1D8-H2K2-dIgG4 | 6.04E+05 | 2.62E−03 | 4.34E−09 |
| 1D8-mHVKV-dIgG4 | 1.44E+06 | 1.35E−04 | 9.40E−11 |
| 1B9-H1K1-IgG4 | 4.24E+05 | 4.54E−04 | 1.07E−09 |
| 1B9-H1K2-IgG4 | 4.75E+05 | 4.90E−04 | 1.03E−09 |
| 1B9-H2K1-IgG4 | 5.91E+05 | 4.54E−04 | 7.68E−10 |
| 1B9-H2K2-IgG4 | 5.77E+05 | 4.30E−04 | 7.45E−10 |
| 1B9-mHVKV-dIgG4 | 1.010E+06 | 1.260E−04 | 1.250E−10 |
| 4A7-mHVKV-dIgG4 | 5.25E+05 | 1.52E−04 | 2.90E−10 |

Example 7. In Vivo Testing of Chimeric and Caninized Anti-dPD-1 Antibodies

In order to test the anti-dPD-1 antibodies in vivo and to predict the effects of these antibodies in dogs, a caninized PD-1 mouse model was generated. The caninized PD-1 mouse model was engineered to express a chimeric PD-1 protein (SEQ ID NO: 40) wherein a part of the extracellular region of the mouse PD-1 protein was replaced with the corresponding canine PD-1 extracellular region. The caninized mouse model provides a new tool for testing new therapeutic treatments in a clinical setting by significantly decreasing the difference between clinical outcome in dogs and in ordinary mice expressing mouse PD-1.

The anti-dPD-1 antibodies were tested for their effect on tumor growth in vivo in a model of colon carcinoma. MC-38 cancer tumor cells (colon adenocarcinoma cell) were injected subcutaneously in the mice. When the tumors in the The injected volume was calculated based on the weight of the mouse at 3 mg/kg. The length of the long axis and the short axis of the tumor were measured and the volume of the tumor was calculated as 0.5×(long axis)×(short axis). The weight of the mice was also measured before the injection, when the mice were placed into different groups (before the first antibody injection), twice a week during the treatment period, and before euthanization.

The tumor growth inhibition percentage (TGI %) was calculated using the following formula: TGI (%)=[1−(Ti−T0)/(Vi−V0)]×100. Ti is the average tumor volume in the treatment group on day i. T0 is the average tumor volume in the treatment group on day zero. Vi is the average tumor volume in the control group on day i. V0 is the average tumor volume in the control group on day zero.

T-test was performed for statistical analysis. A TGI % higher than 60% indicates strong suppression of tumor growth. $P<0.05$ is a threshold to indicate significant difference.

Figure 11:
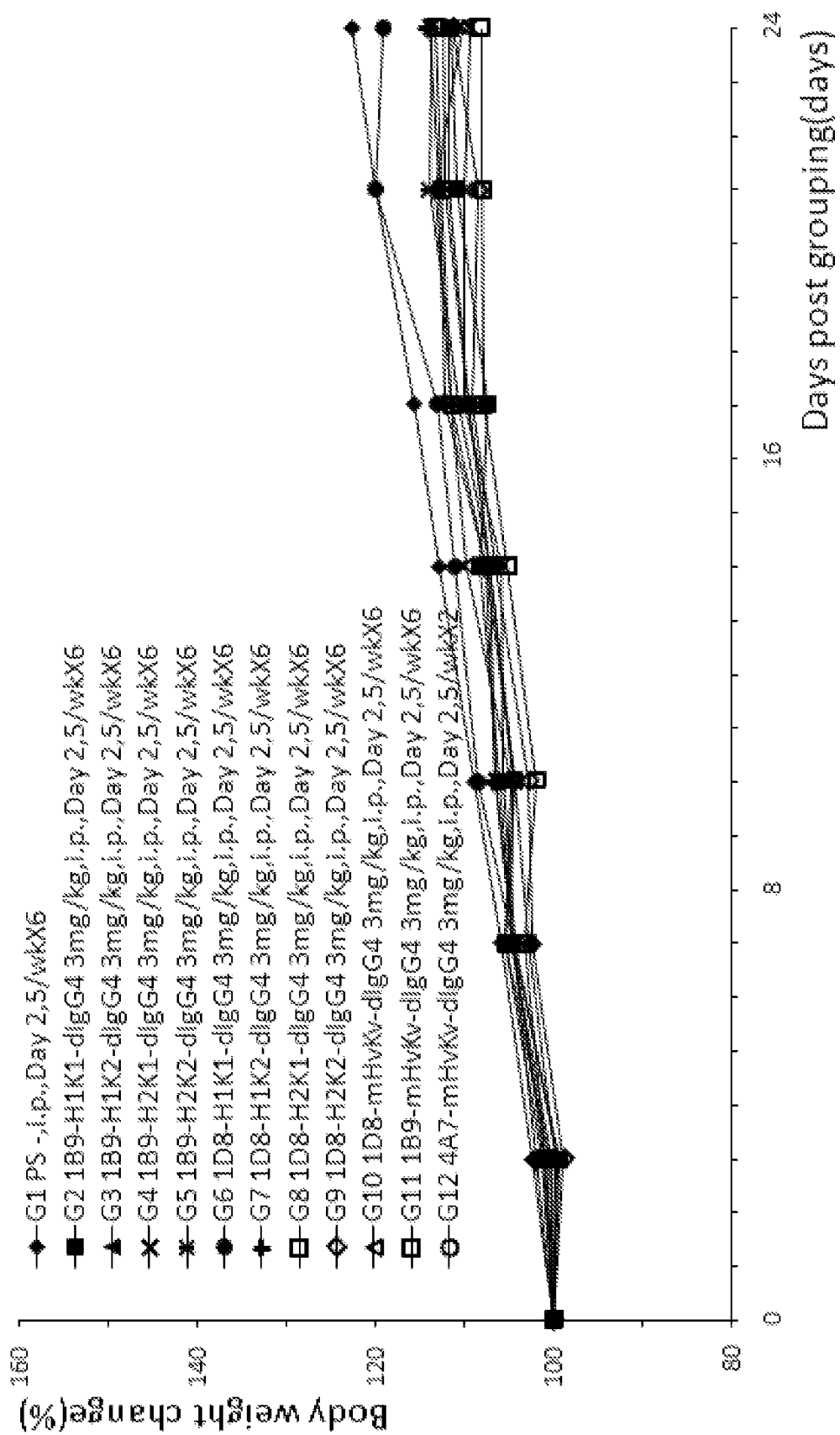
FIG. 11 is a graph showing body weight over time of caninized PD-1 mice (B-dPD-1) with MC-38 tumor cells treated with chimeric and caninized anti-dPD-1 antibodies. PS stands for physiological saline.
Figure 12:
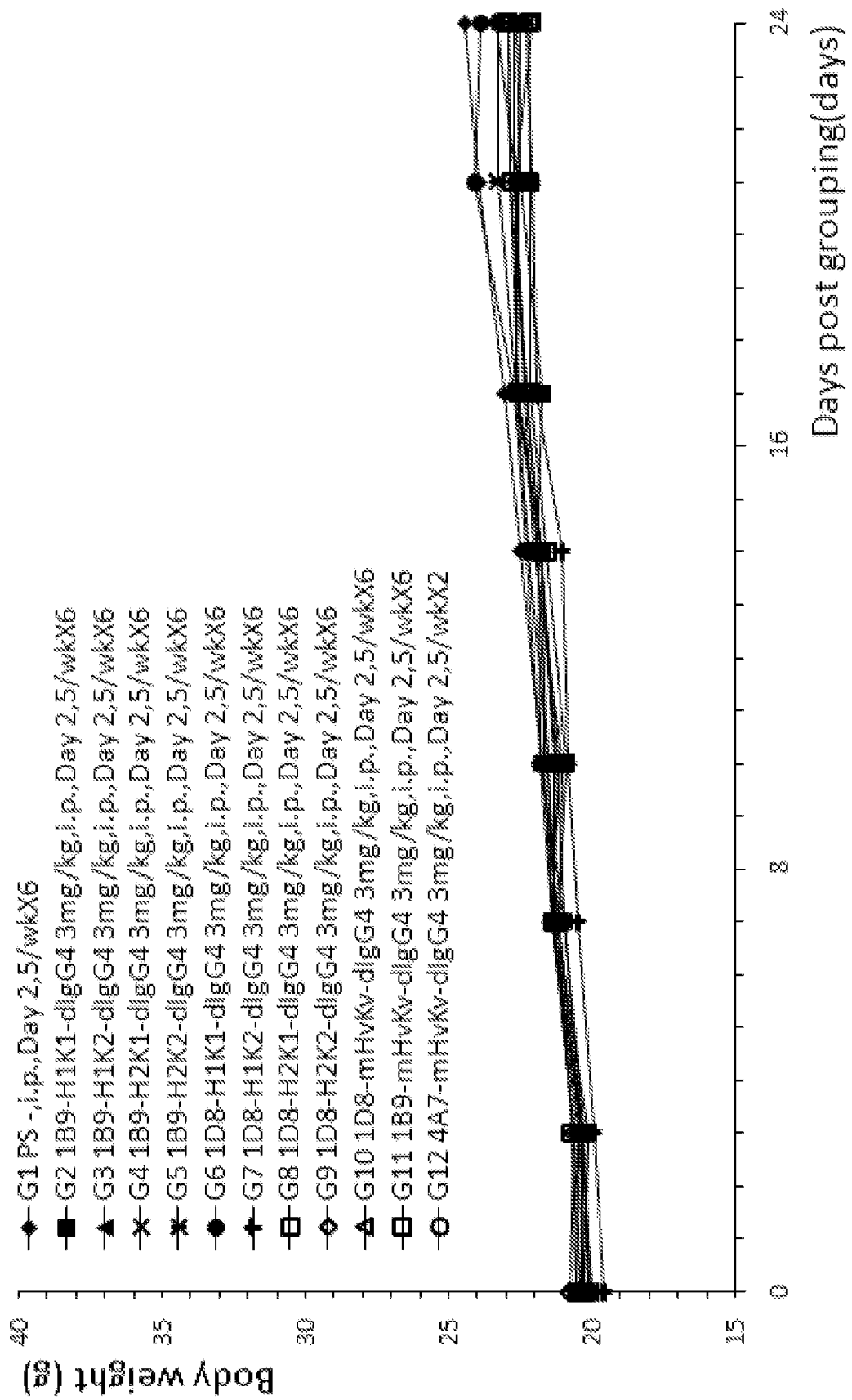
FIG. 12 is a graph showing percentage change of body weight over time of caninized PD-1 mice (B-dPD-1) with MC-38 tumor cells treated with chimeric and caninized anti-dPD-1 antibodies. PS stands for physiological saline.

The weight of the mice was monitored during the entire treatment period. The weight of mice in different groups all increased (FIG. 11, and FIG. 12). No obvious difference in weight was observed among the groups. The results showed that the tested antibodies were well tolerated and were not toxic to the mice.

Figure 13:
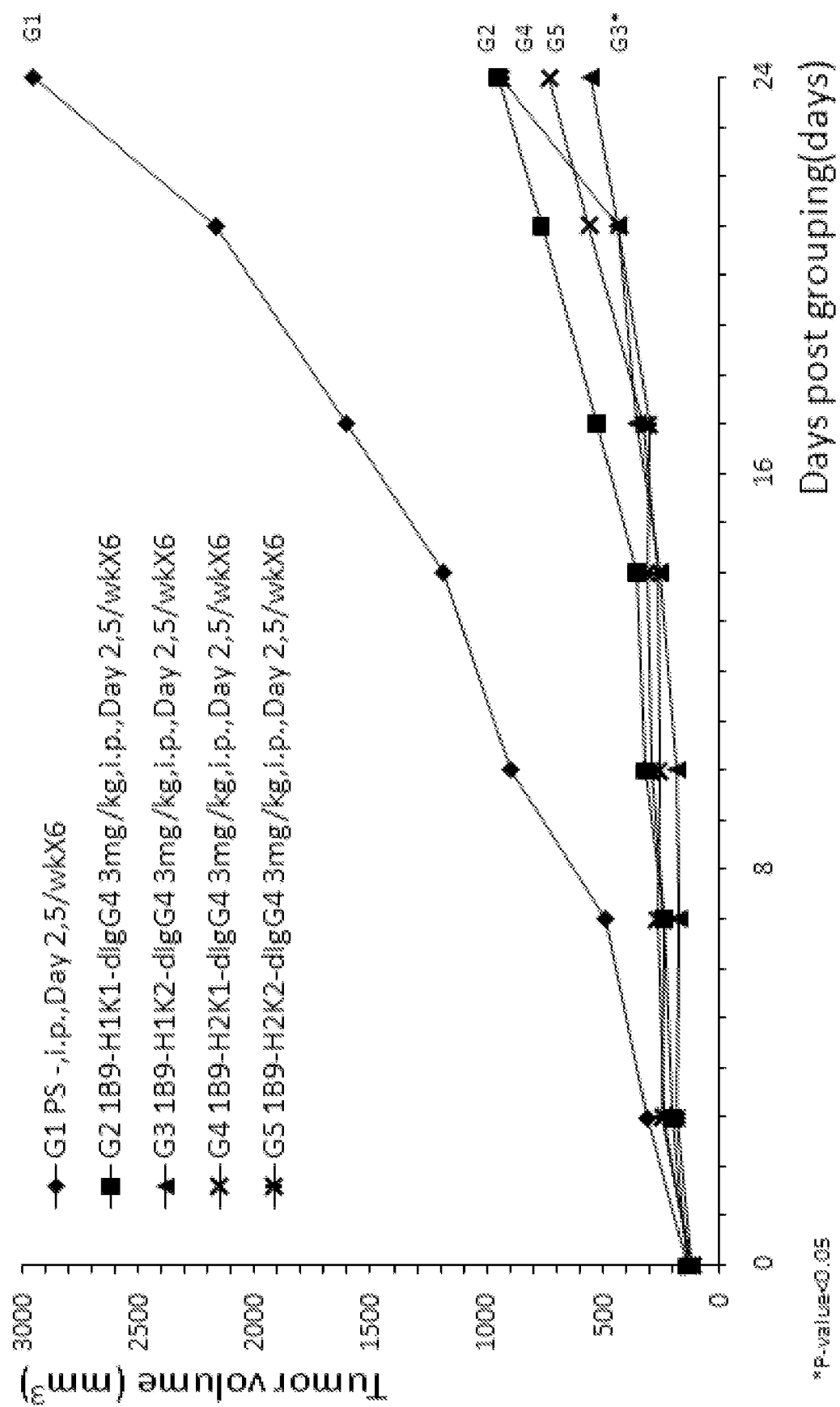
FIG. 13 is a graph showing tumor size over time in caninized PD-1 mice (B-dPD-1) with MC-38 tumor cells treated with several caninized anti-dPD-1 antibodies. PS stands for physiological saline.
Figure 14:
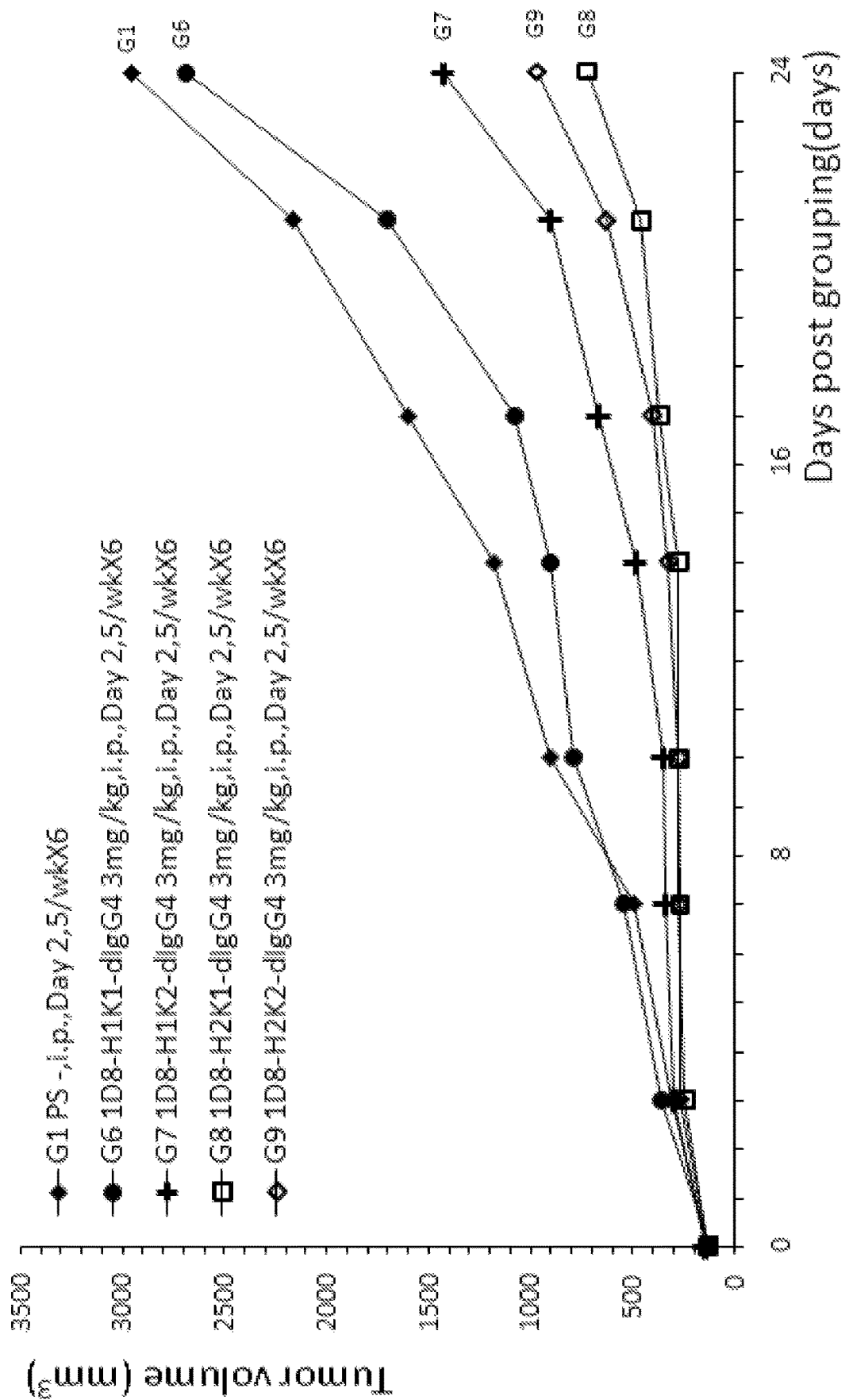
FIG. 14 is a graph showing tumor size over time in caninized PD-1 mice (B-dPD-1) with MC-38 tumor cells treated with several caninized anti-dPD-1 antibodies. PS stands for physiological saline.
Figure 15:
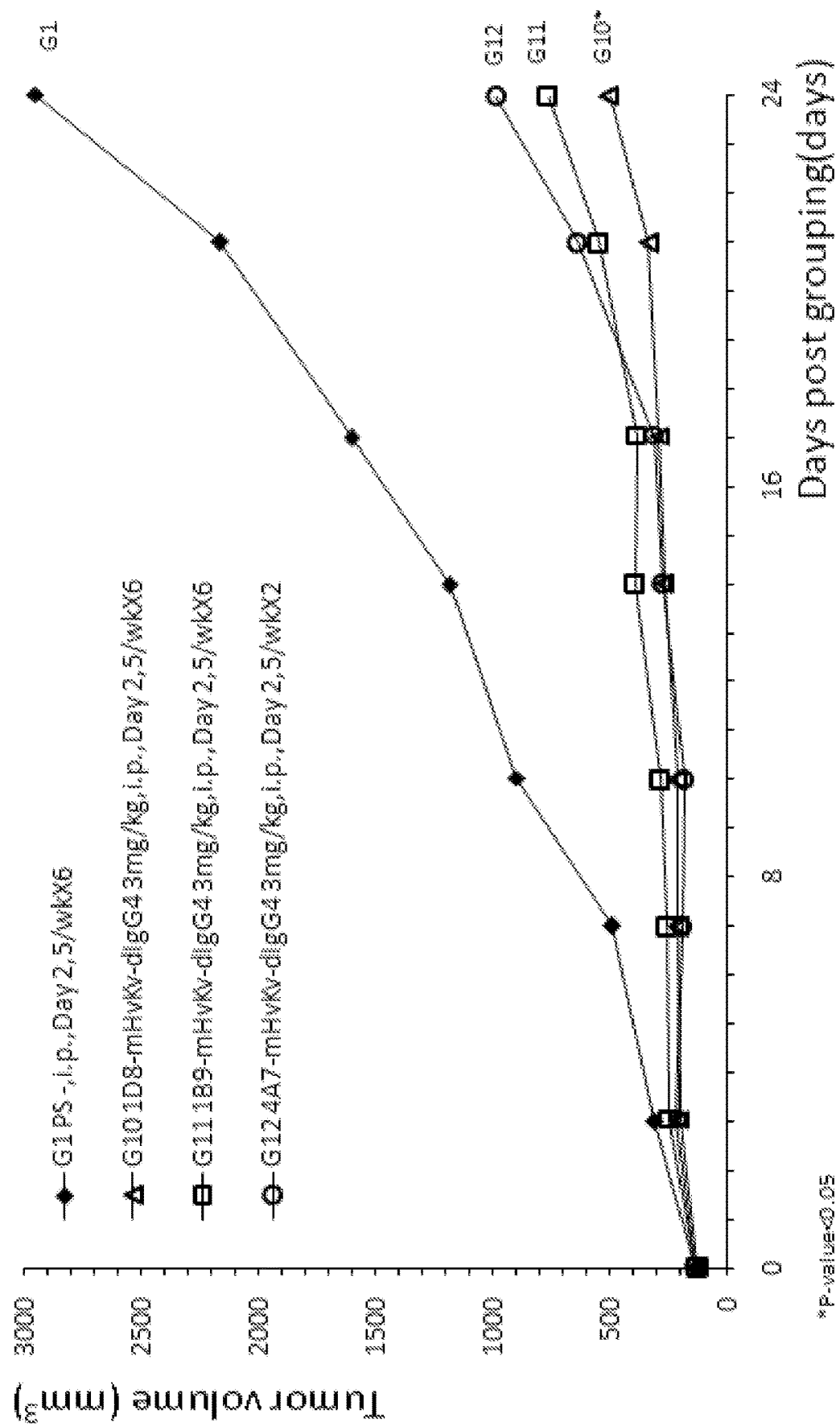
FIG. 15 is a graph showing tumor size over time in caninized PD-1 mice (B-dPD-1) with MC-38 tumor cells treated with several chimeric anti-dPD-1 antibodies. PS stands for physiological saline.

The tumor size in most groups treated with anti-dPD-1 antibodies increased to a lesser extent compared to the control group (FIGS. 13-15). The TGI % at day 24 (24 days after grouping) was also calculated as shown in the table below.

TABLE 7

| | | Tumor volume(mm3) | | | | Survival | TGI % | P value Body weight | P value Tumor Volume |
|---|---|---|---|---|---|---|---|---|---|
| | | Day 0 | Day 10 | Day 17 | Day 24 | | | | |
| Control | G1 | 137 ± 16 | 903 ± 225 | 1605 ± 537 | 2956 ± 932 | 4/4 | n.a. | n.a. | n.a. |
| | G2 | 142 ± 16 | 315 ± 79 | 527 ± 98 | 952 ± 230 | 4/4 | 71.3% | 0.170 | 0.082 |
| | G3 | 121 ± 9 | 185 ± 27 | 354 ± 69 | 558 ± 138 | 4/4 | 84.5% | 0.042 | 0.044 |
| | G4 | 130 ± 20 | 258 ± 80 | 326 ± 100 | 735 ± 284 | 4/4 | 78.6% | 0.005 | 0.063 |
| | G5 | 119 ± 14 | 296 ± 67 | 304 ± 110 | 940 ± 583 | 4/4 | 70.9% | 0.042 | 0.116 |
| | G6 | 131 ± 22 | 796 ± 111 | 1085 ± 207 | 2687 ± 663 | 4/4 | 9.3% | 0.452 | 0.822 |
| Treat | G7 | 146 ± 9 | 350 ± 172 | 667 ± 415 | 1431 ± 954 | 4/4 | 54.4% | 0.088 | 0.297 |
| | G8 | 134 ± 21 | 278 ± 62 | 371 ± 149 | 723 ± 255 | 4/4 | 79.1% | 0.004 | 0.060 |
| | G9 | 140 ± 16 | 278 ± 57 | 405 ± 138 | 970 ± 440 | 4/4 | 70.5% | 0.118 | 0.102 |
| | G10 | 124 ± 18 | 213 ± 37 | 290 ± 63 | 505 ± 146 | 4/4 | 86.5% | 0.002 | 0.041 |
| | G11 | 134 ± 20 | 284 ± 68 | 383 ± 93 | 766 ± 253 | 4/4 | 77.6% | 0.027 | 0.064 |
| | G12 | 141 ± 14 | 184 ± 6 | 314 ± 69 | 990 ± 358 | 4/4 | 69.9% | 0.012 | 0.096 |

The results above show that all anti-dPD-1 antibodies can inhibit tumor growth to some extent. Among them, G3 (1B9-H1K2-dIgG4) and G10 (1D8-mHvKv-dIgG4) had the highest tumor growth inhibition percentage (TGI %). In addition, animals in G12 only received 2 administrations of 4A7-mHvKv-dIgG4, and tumor inhibitory effects were still remarkable.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a subject, the method comprising administering to the subject a therapeutically effective amount of
   an antibody or antigen-binding fragment thereof that binds to PD-1 (Programmed Cell Death Protein 1) comprising:
   a heavy chain variable region (VH) comprising complementarity determining regions (CDRs) 1, 2, and 3; and
   a light chain variable region (VL) comprising CDRs 1, 2, and 3,
   wherein the VH CDRs 1, 2, and 3 amino acid sequences and the VL CDRs, 1, 2, and 3 amino acid sequences are one of the following:
   (1) the VH CDRs 1, 2, 3 amino acid sequences are set forth in SEQ ID NOs: 1, 2, 3, respectively, and the VL CDRs 1, 2, 3 amino acid sequences are set forth in SEQ ID NOs: 4, 5, 6, respectively; and
   (2) the VH CDRs 1, 2, 3 amino acid sequences are set forth in SEQ ID NOs: 19, 20, 21, respectively, and the VL CDRs 1, 2, 3 amino acid sequences are set forth in SEQ ID NOs: 22, 23, 24, respectively.

2. The method of claim 1, wherein the cancer is a solid tumor.

3. The method of claim 1, wherein the cancer is a carcinoma.

4. The method of claim 1, wherein the cancer is a squamous cell carcinoma, melanoma, adenocarcinoma, breast cancer, sarcoma, liver cancer, testicular cancer, non-small cell lung cancer (NSCLC), head and neck cancer, renal cell carcinoma (RCC), bladder cancer, gastric cancer, urothelial cancer, Merkel-cell carcinoma, or colorectal carcinoma.

5. The method of claim 1, wherein the VH comprises an amino acid sequence that is identical to SEQ ID NO: 49, 50, 51, or 59, and the VL comprises an amino acid sequence that is identical to SEQ ID NO: 52, 53, 54, or 60.

6. The method of claim 1, wherein the VH comprises the sequence of SEQ ID NO: 49 and the VL comprises the sequence of SEQ ID NO: 52.

7. The method of claim 1, wherein the VH comprises the sequence of SEQ ID NO: 49 and the VL comprises the sequence of SEQ ID NO: 53.

8. The method of claim 1, wherein the VH comprises the sequence of SEQ ID NO: 49 and the VL comprises the sequence of SEQ ID NO: 54.

9. The method of claim 1, wherein the VH comprises the sequence of SEQ ID NO: 49 and the VL comprises the sequence of SEQ ID NO: 60.

10. The method of claim 1, wherein the VH comprises the sequence of SEQ ID NO: 50 and the VL comprises the sequence of SEQ ID NO: 52.

11. The method of claim 1, wherein the VH comprises the sequence of SEQ ID NO: 50 and the VL comprises the sequence of SEQ ID NO: 53.

12. The method of claim 1, wherein the VH comprises the sequence of SEQ ID NO: 50 and the VL comprises the sequence of SEQ ID NO: 54.

13. The method of claim 1, wherein the VH comprises the sequence of SEQ ID NO: 50 and the VL comprises the sequence of SEQ ID NO: 60.

14. The method of claim 1, wherein the VH comprises the sequence of SEQ ID NO: 51 and the VL comprises the sequence of SEQ ID NO: 52.

15. The method of claim 1, wherein the VH comprises the sequence of SEQ ID NO: 51 and the VL comprises the sequence of SEQ ID NO: 53.

16. The method of claim 1, wherein the VH comprises the sequence of SEQ ID NO: 51 and the VL comprises the sequence of SEQ ID NO: 54.

17. The method of claim 1, wherein the VH comprises the sequence of SEQ ID NO: 51 and the VL comprises the sequence of SEQ ID NO: 60.

18. The method of claim 1, wherein the VH comprises the sequence of SEQ ID NO: 59 and the VL comprises the sequence of SEQ ID NO: 52.

19. The method of claim 1, wherein the VH comprises the sequence of SEQ ID NO: 59 and the VL comprises the sequence of SEQ ID NO: 53.

20. The method of claim 1, wherein the VH comprises the sequence of SEQ ID NO: 59 and the VL comprises the sequence of SEQ ID NO: 54.

21. The method of claim 1, wherein the VH comprises the sequence of SEQ ID NO: 59 and the VL comprises the sequence of SEQ ID NO: 60.

22. The method of claim 1, wherein the VH comprises CDRs 1, 2, 3 with the amino acid sequences set forth in SEQ ID NOs: 1, 2, and 3, respectively, and the VL comprises CDRs 1, 2, 3 with the amino acid sequences set forth in SEQ ID NOs: 4, 5, and 6, respectively, according to Kabat definition.

23. The method of claim 1, wherein the VH comprises CDRs 1, 2, 3 with the amino acid sequences set forth in SEQ ID NOs: 19, 20, and 21, respectively, and the VL comprises CDRs 1, 2, 3 with the amino acid sequences set forth in SEQ ID NOs: 22, 23, and 24, respectively, according to Chothia definition.

24. The method of claim 1, wherein the antibody or antigen-binding fragment specifically binds to canine PD-1.

25. The method of claim 1, wherein the antibody or antigen-binding fragment binds to PD-1 of *Ailuropoda melanoleuca* (giant panda).

26. The method of claim 1, wherein the antibody or antigen-binding fragment is a caninized antibody or antigen-binding fragment thereof.

27. The method of claim 1, wherein the subject is a dog.

28. The method of claim 1, wherein an additional therapeutic agent is administered to the subject, wherein the additional therapeutic agent is an anti-OX40 antibody, an anti-PD-L1 antibody, an anti-PD-L2 antibody, an anti- LAG-3 antibody, an anti-TIGIT antibody, an anti-BTLA antibody, an anti-CTLA-4 antibody, or an anti-GITR antibody.

29. A method of decreasing the rate of tumor growth, the method comprising
   contacting a tumor with an effective amount of
   an antibody or antigen-binding fragment thereof that binds to PD-1 comprising:
   a VH comprising CDRs 1, 2, and 3; and
   a VL comprising CDRs 1, 2, and 3,
   wherein the VH CDRs 1, 2, and 3 amino acid sequences and the VL CDRs, 1, 2, and 3 amino acid sequences are one of the following:
   (1) the VH CDRs 1, 2, 3 amino acid sequences are set forth in SEQ ID NOs: 1, 2, 3, respectively, and the VL CDRs 1, 2, 3 amino acid sequences are set forth in SEQ ID NOs: 4, 5, 6, respectively; and
   (2) the VH CDRs 1, 2, 3 amino acid sequences are set forth in SEQ ID NOs: 19, 20, 21, respectively, and the VL CDRs 1, 2, 3 amino acid sequences are set forth in SEQ ID NOs: 22, 23, 24, respectively.

30. A method of killing a tumor cell, the method comprising
   contacting a tumor cell with an effective amount of
   an antibody or antigen-binding fragment thereof that binds to PD-1 comprising:
   a VH comprising CDRs 1, 2, and 3; and
   a VL comprising CDRs 1, 2, and 3,
   wherein the VH CDRs 1, 2, and 3 amino acid sequences and the VL CDRs, 1, 2, and 3 amino acid sequences are one of the following:
   (1) the VH CDRs 1, 2, 3 amino acid sequences are set forth in SEQ ID NOs: 1, 2, 3, respectively, and the VL CDRs 1, 2, 3 amino acid sequences are set forth in SEQ ID NOs: 4, 5, 6, respectively; and
   (2) the VH CDRs 1, 2, 3 amino acid sequences are set forth in SEQ ID NOs: 19, 20, 21, respectively, and the VL CDRs 1, 2, 3 amino acid sequences are set forth in SEQ ID NOs: 22, 23, 24, respectively.

* * * * *